(12) United States Patent
Hartwig et al.

(10) Patent No.: US 11,518,768 B2
(45) Date of Patent: Dec. 6, 2022

(54) ARTIFICIAL METALLOENZYMES CONTAINING NOBLE METAL-PORPHYRINS

(71) Applicant: The Regents of the University of California, Oakland, CA (US)

(72) Inventors: John F. Hartwig, Berkeley, CA (US); Hanna M. Key, Berkeley, CA (US); Pawel Dydio, Kehl (DE); Douglas S. Clark, Orinda, CA (US)

(73) Assignee: The Regents of the University of California, Oakland, CA (US)

( * ) Notice: Subject to any disclaimer, the term of this patent is extended or adjusted under 35 U.S.C. 154(b) by 287 days.

(21) Appl. No.: 15/953,331

(22) Filed: Apr. 13, 2018

(65) Prior Publication Data

US 2018/0305368 A1 Oct. 25, 2018

Related U.S. Application Data

(63) Continuation-in-part of application No. PCT/US2016/057032, filed on Oct. 14, 2016.

(60) Provisional application No. 62/384,011, filed on Sep. 6, 2016, provisional application No. 62/241,487, filed on Oct. 14, 2015.

(51) Int. Cl.
| | | |
|---|---|---|
| *C12N 9/02* | (2006.01) | |
| *C12N 15/65* | (2006.01) | |
| *C12P 13/00* | (2006.01) | |
| *C07D 487/22* | (2006.01) | |
| *C07K 14/805* | (2006.01) | |
| *B01J 31/18* | (2006.01) | |
| *C07K 14/795* | (2006.01) | |
| *C07K 14/80* | (2006.01) | |
| *B01J 31/00* | (2006.01) | |
| *C12N 9/00* | (2006.01) | |

(52) U.S. Cl.
CPC .......... *C07D 487/22* (2013.01); *B01J 31/003* (2013.01); *B01J 31/18* (2013.01); *B01J 31/1815* (2013.01); *C07K 14/795* (2013.01); *C07K 14/80* (2013.01); *C07K 14/805* (2013.01); *C12N 9/0002* (2013.01); *C12N 9/0071* (2013.01); *C12Y 114/14001* (2013.01); *B01J 2231/324* (2013.01); *B01J 2531/025* (2013.01); *B01J 2531/17* (2013.01); *B01J 2531/824* (2013.01); *B01J 2531/827* (2013.01); *B01J 2531/828* (2013.01)

(58) Field of Classification Search
CPC ................ C12N 9/0042; C12N 9/0071; C12Y 106/02004; C12Y 109/03001; C12P 17/10; C12P 5/002; C12P 5/005
USPC ............... 435/69.7, 117, 120, 189, 195, 69.6
See application file for complete search history.

(56) References Cited

U.S. PATENT DOCUMENTS

| | | |
|---|---|---|
| 7,129,329 B1 | 10/2006 | Alam et al. |
| 8,993,262 B2 | 3/2015 | Coelho et al. |
| 9,322,001 B2 | 4/2016 | Farinas et al. |
| 9,399,762 B2 | 7/2016 | Farwell et al. |
| 2011/0243849 A1* | 10/2011 | Marletta .............. C07K 14/805 424/9.1 |

FOREIGN PATENT DOCUMENTS

| | | |
|---|---|---|
| WO | 2014/058729 A1 | 4/2014 |
| WO | 2016/086015 A1 | 6/2016 |
| WO | 2016/191612 A2 | 12/2016 |

OTHER PUBLICATIONS

McIntosh et al., JACS, 2015, 137, 13861-13865.*
Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
International Search Report and Written Opinion from PCT/US2016/057032, dated May 16, 2017, 14 pages.
Anding, et al., "Iridium Porphyrin Catalyzed N—H Insertion Reactions: Scope and Mechanism," Organometallics (2013), 32, 2599-2607.
Hvasanov, et al., "Optimising the Synthesis, Polymer Membrane Encapsulation and Photoreduction Performance of Ru(II)- and Ir(III)-bis(terpyridine) cytochrome c Bioconjugates," Organic & Biomolecular Chemistry 2013, 11, 4602-4612.
Uno, et al., "Inversion of Axial Coordination in Myoglobin to Create a 'Proximal' Ligand Binding Pocket," Biochemistry 2003, 42, 10191-10199.
Dydio, et al., "An Artificial Metalloenzyme with the Kinetics of Native Enzymes," Science 2016, 354:6308, 102-106.

\* cited by examiner

*Primary Examiner* — Tekchand Saidha
*Assistant Examiner* — Mohammad Y Meah
(74) *Attorney, Agent, or Firm* — Emily M. Haliday; Weaver Austin Villeneuve & Sampson LLP

(57) ABSTRACT

The present invention is drawn to artificial metalloenzymes for use in cyclopropanation reactions, amination and C—H insertion.

19 Claims, 31 Drawing Sheets

Specification includes a Sequence Listing.

Expedient Approach to Diversely Metallated [M]-PIX Proteins

| B-Me Styrene | 93H | 93C | 93D | 93E | 93M | 93S | 93A | 93G |
|---|---|---|---|---|---|---|---|---|
| Fe(Cl)-PIX | | | | | | | | |
| Co(Cl)-PIX | | | | | | | | |
| Cu-PIX | | | | | | | | |
| Mn(Cl)-PIX | | | | | | | | |
| Rh-PIX | | | | | | | | |
| Ir(Cl)-PIX | | | | | | | | |
| Ir(Me)-PIX | | | | | | | | |
| Ru(CO)-PIX | | | | | | | | |
| Ag-PIX | | | | | | | | |

| TON |
|---|
| <1 |
| 1-5 |
| 6-10 |
| 11-20 |
| >20 |

| C-H Insertion | 93H | 93C | 93D | 93E | 93M | 93S | 93A | 93G |
|---|---|---|---|---|---|---|---|---|
| Fe(Cl)-PIX | | | | | | | | |
| Co(Cl)-PIX | | | | | | | | |
| Cu-PIX | | | | | | | | |
| Mn(Cl)-PIX | | | | | | | | |
| Rh-PIX | | | | | | | | |
| Ir(Cl)-PIX | | | | | | | | |
| Ir(Me)-PIX | | | | | | | | |
| Ru(CO)-PIX | | | | | | | | |
| Ag-PIX | | | | | | | | |

| TON |
|---|
| <4 |
| 4-10 |
| 11-30 |
| 31-60 |
| >60 |

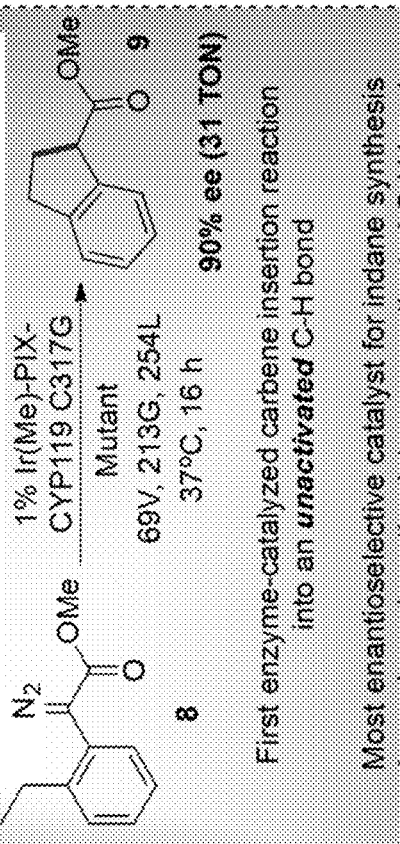

FIG. 23D Insertion into an *unactivated*, primary C-H bond

First enzyme-catalyzed carbene insertion reaction into an *unactivated* C-H bond Most enantioselective catalyst for indane synthesis by carbene insertion into an unactivated C-H bond

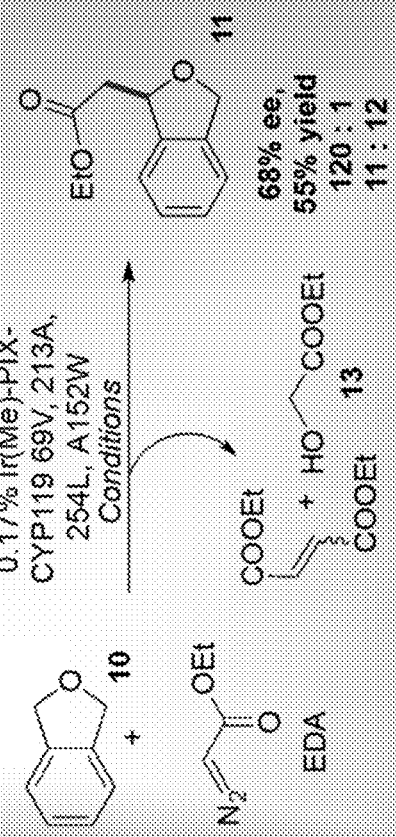

FIG. 23E *Intermolecular* insertion into a C-H bond

First enzyme-catalyzed *intermolecular* carbene insertion into a C-H bond

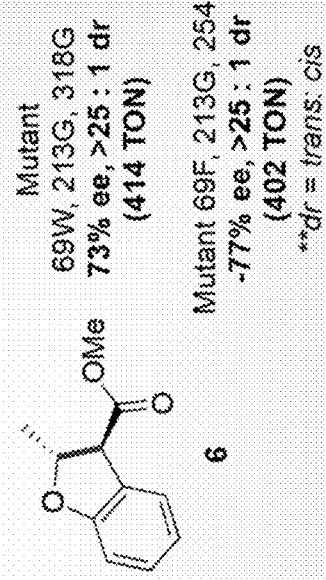

FIG. 23B Insertion into an *activated*, secondary C-H bond

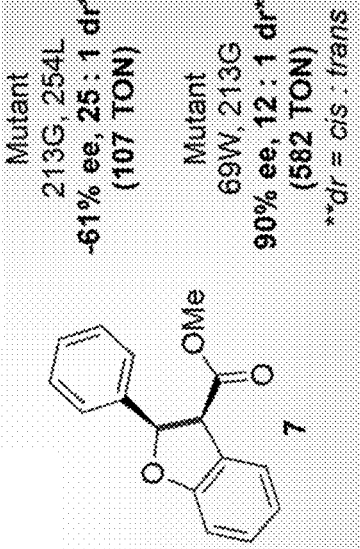

FIG. 23C Insertion into a *sterically hindered* C-H bond

First enzyme-catalyzed carbene insertion reaction into a *sterically hindered* C-H bond

FIG. 30

| Parent Mutant | Additional Mutations | ee (%) | dr* | Yield | TON |
|---|---|---|---|---|---|
| Ir(Me)-CYP119(+) | L155W | 99% | 19 : 1 | 44% | 440 |
| Ir(Me)-CYP119(-) | V254L, L155T | -99% | 7 : 1 | 68% | 1006 |
| Selectivity of Free Ir(Me)-PIX | | 0% | 1 : 4 | | |

\* cis : trans

| Parent Mutant | Additional Mutations | dr* | Yield | TON |
|---|---|---|---|---|
| Ir(Me)-CYP119(-) | F310W | 204 : 1 : 1 : 1 | 76% | 1300 |
| Selectivity of Free Ir(Me)-PIX | | 3 : 1 : 1 : 3 | | |

\* Major diastereomer 29 as shown. Minor diastereomers not determined

30

90% ee, 15 : 1 dr, 496 TON

33

14 : 1 dr, 36 TON

32

94% ee, 108 : 1 dr, 99 TON

34

80% ee, 8 : 1 dr, 45 TON

ARTIFICIAL METALLOENZYMES CONTAINING NOBLE METAL-PORPHYRINS

CROSS-REFERENCES TO RELATED APPLICATIONS

This application is a continuation-in-part of PCT application no. PCT/US2016/057032, filed Oct. 14, 2016, which claims priority to U.S. Application Nos. 62/384,011, filed Sep. 6, 2016, and 62/241,487, filed Oct. 14, 2015, each of which is incorporated in its entirety herein for all purposes.

STATEMENT AS TO RIGHTS TO INVENTIONS MADE UNDER FEDERALLY SPONSORED RESEARCH AND DEVELOPMENT

This invention was made with Government support under Grant No. DE-AC02-05CH11231, awarded by the U.S. Department of Energy, and Grant No. FA9550-11-C-0028, awarded by the U.S. Department of Defense. The government has certain rights in this invention.

SEQUENCE LISTING SUBMITTED AS ASCII TEXT FILE

This application includes a Sequence Listing as a text file named 077429-1075895_SEQ_LST" created on Apr. 13, 2018 and containing 27,840 bytes. The material contained in this text file is hereby incorporated by reference in its entirety for all purposes.

BACKGROUND OF THE INVENTION

Native enzymes undergo a range of synthetically valuable reactions with high activity and high stereo-, regio- and site-selectivities enabled by the structure of their active sites. Metalloenzymes form a distinct class of natural enzymes, which contain a metal in the active site; this metal is often contained in a cofactor embedded within this site. The catalytic activity of a metalloenzyme is determined by both the primary coordination sphere of the metal and the surrounding protein scaffold. In some cases, laboratory evolution has been used to develop variants of metalloenzymes for selective reactions of unnatural substrates. Yet, with few exceptions, the classes of reactions that such enzymes undergo are limited to those of biological transformations.

To combine the favorable qualities of enzymes with the diverse reactivity of synthetic transition-metal catalysts, abiological transition-metal centers or cofactors have been incorporated into native proteins. The resulting systems, called artificial metalloenzymes, catalyze classes of reactions for which there is no known enzyme (i.e. abiological transformations). Although envisioned to combine the selectivities of enzymes with the reactivities of transition metal complexes, artificial metalloenzymes are not merely the sum of the properties of a protein and a transition metal complex. The incorporation of an abiological metal cofactor into a protein can change significantly the properties of the protein that are essential to its function as a catalyst, including its dynamics, its thermal and kinetic stability, and the size and accessibility of its substrate binding site. Likewise, the encapsulation of the metal complex changes significantly the properties of the metal catalyst, such as its geometry, oxidation state, or primary coordination sphere, as well as the accessibility of its metal site to the substrate. Consequently, the global properties of artificial metalloenzymes, particularly the rates and stability of the resulting systems, have not reflected the cumulative properties of the isolated protein and its abiological metal components.

A major current challenge facing the creation of artificial metalloenzymes is to attain the fundamental characteristics of natural enzymes, such as high activity (turnover frequency, TOF) and high productivity (turnover number, TON). Even when the artificial enzymes contain metal catalysts that are highly active catalysts for a targeted reaction (such as Cp*Rh and Ir complexes for transfer hydrogenation), than the rates and TON of reactions catalyzed by free metal complexes in organic solvent. For example, Ward and coworkers reported a highly enantioselective artificial metalloenzyme for imine hydrogenation, prepared by bioconjugation of an Ir-cofactor to streptavidin. In this case, the reaction occurs with 96% ee, but with rate of only 0.68 $min^{-1}$. This rate is more than an order of magnitude lower than that of the same reaction catalyzed by the Ir-cofactor in the absence of the protein. In addition to the limitations in activity, artificial metalloenzymes lack many of the practical characteristics of enzymes used in synthesis, such as suitability for preparative-scale reactions and potential to be recovered and reused.

One reason that artificial metalloenzymes react more slowly than native enzymes is the absence of a defined binding site for the substrate. Natural enzymes generally bind their substrates with high affinity and in a conformation that leads to extremely fast rates and high selectivity. If the artificial metalloenzyme is generated by incorporation of full metal-ligand complexes into the substrate binding site of a natural enzyme or protein, the space remaining to bind a reactant for a catalytic process is limited, and the interactions by which the protein binds the reactant are compromised. Accordingly, there is a need for new metalloenzymes with improved reactivity to facilitate bond formation. Surprisingly, the present invention meets this and other needs.

BRIEF SUMMARY OF THE INVENTION

In one embodiment, the present invention provides a catalyst composition comprising a porphyrin, M(L), wherein the porphyrin and M(L) form a complex, M is a metal selected from the group consisting of Ir, Pd, Pt and Ag, L is absent or a ligand, and a heme apoprotein, wherein the porphyrin-M(L) complex is bound to the heme apoprotein. In some instances, the heme apoprotein has a mutation close to the active site.

In another embodiment, the present invention provides a catalyst composition comprising a porphyrin, M(L), wherein the porphyrin and M(L) form a complex, M is a metal selected from the group consisting of Ir, Pd, Pt, Ag, Mn, Ru, Co, Zn, Cu, Ni, Cr, Rh and Os, L is absent or a ligand, and a mutant heme apoprotein selected from the group consisting of a myoglobin and a P450, wherein the porphyrin-M(L) complex is bound to the heme apoprotein. In some instances, the mutant heme apoprotein has a mutation close to the active site.

In another embodiment, the present invention provides a method of forming a bond, comprising forming a reaction mixture comprising a catalyst composition of the present invention, a reactant selected from a carbene precursor or a nitrene precursor, and a substrate comprising an olefin or a C—H group, under conditions where the reactant forms a carbene or nitrene which inserts into the alkene or C—H bond of the substrate to form the bond between the reactant and the substrate.

In another embodiment, the present invention provides a heme apoprotein comprising porphyrin-Ir(L) complex, wherein L is a ligand selected from the group consisting of methyl, ethyl, F, Cl and Br, and wherein the porphyrin and Ir(L) form a complex, wherein the heme apoprotein comprises an amino acid substitution, relative to the native apoprotein amino acid sequence, at a position close to the active site.

BRIEF DESCRIPTION OF THE DRAWINGS

FIG. 23A-23E presents the most selective variants of Ir(Me)-PIX CYP119 identified to catalyze enantioselective intra- and intermolecular C—H carbene insertion reactions of activated and unactivated C—H bonds. FIG. 23A-23D: Intramolecular C—H carbene insertion reactions. Reactions were conducted at room temperature unless otherwise noted. FIG. 23E: An intermolecular C—H carbene insertion reaction. Conditions: 10 (10 umol) and EDA (100 umol); EDA was added as a 50% solution in DMF over 1 hour using a syringe pump.

FIG. 30 presents results of cyclopropanation of vinylarenes with different substitution patterns on the alkene using Ir(Me)-CYP119 mutants. The reactions were conducted on 1 mL scale under the listed conditions using 20 mM substrate (17, 18, 19, or 20) and 3 equiv. of EDA (added over 3 hours by syringe pump as a 30% (v:v) solution in DMF). c=cis, t=trans. The yields were determined by GC using dodecane as internal standard. All variants contained the mutations C317G in addition to those listed. The absolute stereochemistry of products for 17 and 18 was assigned based on prior literature (Coelho et al. (2013) *Science* 339:307; Bonaccorsi et al. (2005) *Organometallics* 24:4953). The absolute configurations of products 23 and 24 were not assigned.

DETAILED DESCRIPTION OF THE INVENTION

I. General

Figure 1A:
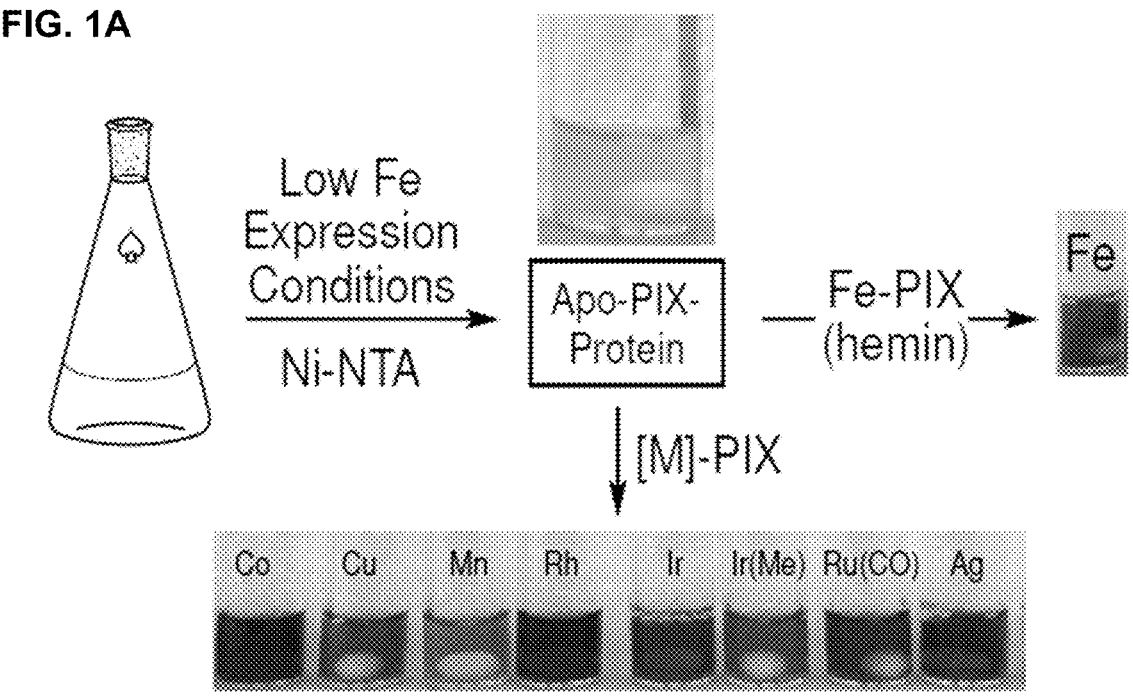
FIG. 1A illustrates the direct expression, purification, and diverse metallation of apo-PIX proteins.
Figure 1B:
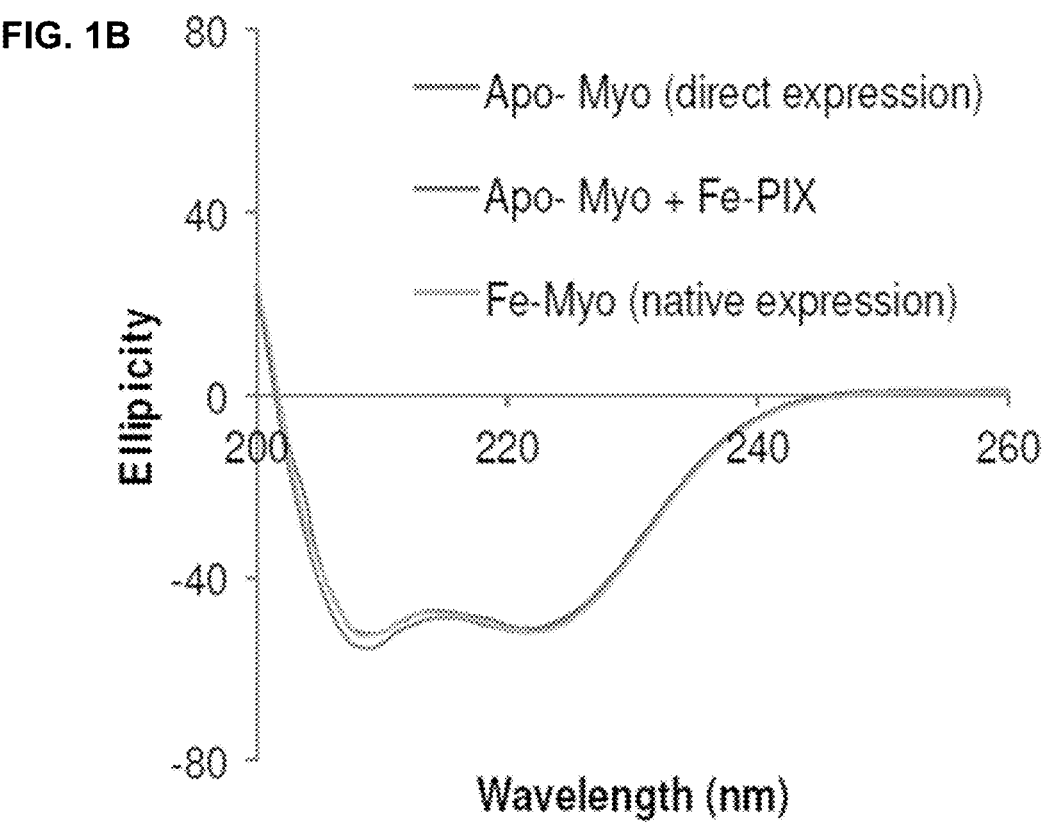
FIG. 1B illustrates a comparison of the CD spectra obtained from directly expressed apo-Myo, the same protein reconstituted with Fe-PIX (hemin), and the same mutant expressed as a native Fe-PIX protein.

The present invention provides new artificial metalloenzymes having improved reactivity and that can facilitate formation of bonds, including those to the carbon of unactivated C—H bonds. The metalloenzymes of the present invention can have a non-native heme component, such as an Iridium metal in the porphyrin, as well as a mutant enzyme. The metalloenzymes provide improved stereoselectivity and reactivity compared to metalloenzymes in the art.

II. Definitions

"Porphyrin" refers to a macrocyclic aromatic ring structure with alternating pyrrole and methyne groups forming the ring. Porphyrins can be substituted to form compounds such as pheophorbide or pyropheophorbide, among others. Porphyrins are a key component of hemoglobin and can complex a metal, such a iron, via the nitrogen atoms of the pyrrole rings.

"Metal" refers to elements of the periodic table that are metallic and that can be neutral, or negatively or positively charged as a result of having more or fewer electrons in the valence shell than is present for the neutral metallic element. Metals useful in the present invention include the alkali metals, alkali earth metals, transition metals and post-transition metals. Alkali metals include Li, Na, K, Rb and Cs. Alkaline earth metals include Be, Mg, Ca, Sr and Ba. Transition metals include Sc, Ti, V, Cr, Mn, Fe, Co, Ni, Cu, Zn, Y, Zr, Nb, Mo, Tc, Ru, Rh, Pd, Ag, Hf, Ta, W, Re, Os, Ir, Pt, Au, and Hg. Post-transition metals include Al, Ga, In, Tl, Ge, Sn, Pb, Sb, Bi, and Po. Rare earth metals include Sc, Y, La, Ce, Pr, Nd, Sm, Eu, Gd, Tb, Dy, Ho, Er, Tm, Yb and Lu. One of skill in the art will appreciate that the metals described above can each adopt several different oxidation states, all of which are useful in the present invention. In some instances, the most stable oxidation state is formed, but other oxidation states are useful in the present invention.

"Ligand" refers to a substituent on the metal of the porphyrin-metal complex. The ligand stabilizes the metal and donates electrons to the metal to complete the valence shell of electrons.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkene" or "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkyne" or "alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Halogen" refers to fluorine, chlorine, bromine and iodine.

"Haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, flouromethyl, etc. In some instances, the term "perfluoro" can be used to define a compound or radical where all the hydrogens are replaced with fluorine. For example, perfluoromethyl refers to 1,1,1-trifluoromethyl.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Heteroalkyl" refers to an alkyl group of any suitable length and having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers and alkyl-amines. The heteroatom portion of the heteroalkyl can replace a hydrogen of the alkyl group to form a hydroxy, thio or amino group. Alternatively, the heteroartom portion can be the connecting atom, or be inserted between two carbon atoms.

"Amine" or "amino" refers to an —N(R)$_2$ group where the R groups can be hydrogen, alkyl, alkenyl, alkynyl, cycloalkyl, heterocycloalkyl, aryl, or heteroaryl, among others. The R groups can be the same or different. The amino groups can be primary (each R is hydrogen), secondary (one R is hydrogen) or tertiary (each R is other than hydrogen).

"Alkyl amine" refers to an alkyl group as defined within, having one or more amino groups. The amino groups can be primary, secondary or tertiary. The alkyl amine can be further substituted with a hydroxy group to form an amino-hydroxy group. Alkyl amines useful in the present invention include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with C1-6 alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Alkenyl-aryl" or "arylalkene" refers to a radical having both an alkene component and a aryl component, as defined above. Representative arylalkene groups include styrene or vinyl-benzene. Alkenyl-aryl groups can be substituted or unsubstituted.

"Pentafluorophenyl" refers to a phenyl ring substituted with 5 fluorine groups.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

The groups defined above can optionally be substituted by any suitable number and type of subsituents. Representative substituents include, but are not limited to, halogen, haloalkyl, haloalkoxy, —OR', =O, —OC(O)R', —(O)R', —O$_2$R', —ONR'R", —OC(O)NR'R", =NR', =N—OR', —NR'R", —NR"C(O)R', —NR'—(O)NR"R''', —NR"C(O)OR', —NH—(NH$_2$)=NH, —NR'C(NH$_2$)=NH, —NH—(NH$_2$)=NR', —SR', —S(O)R', —S(O)$_2$R', —S(O)$_2$NR'R", —NR'S(O)$_2$R", —N$_3$ and —NO$_2$. R', R" and R''' each independently refer to hydrogen, unsubstituted alkyl, such as unsubstituted C$_{1-6}$ alkyl. Alternatively, R' and R", or R" and R''', when attached to the same nitrogen, are combined with the nitrogen to which they are attached to form a heterocycloalkyl or heteroaryl ring, as defined above.

In the context of this invention, the term "heme protein" refers to a protein having a prosthetic group that comprises a porphyrin ring, which in its native state, has an iron metal contained within the porphyrin ring. The prosthetic group may comprise protoporphyrin IX, which has a porphyrin ring, substituted with four methyl groups, two vinyl groups, and two propionic acid groups, and complexes with an iron atom to form heme. A "heme apoprotein" as used herein refers to a heme protein that lacks the metal/porphyrin complex. The term "heme protein" or "heme apoprotein" encompasses fragments of heme apoproteins, so long as the fragment comprises an active site, as well as variants of native heme apoproteins.

The term "active site" as used in reference to a "heme protein" refers to the porphyrin binding region of the heme protein. An amino acid change "close to the active site" refers to a position that is 25 Angstroms or less from the iron center of a native heme protein, where any part of the amino acid is 25 Angstroms or less from the iron center of the native heme protein. In some embodiments, an amino acid residue close to the active site has any part of the amino acid molecule that is 20 Angstroms or less from the iron center of the active site in the native heme protein. In some embodiments, an amino acid residue close to the active site has any part of the amino acid that is 15 Angstroms or less from the iron center of the active site in the native heme protein The terms "wild type", "native", and "naturally occurring" with respect to a heme protein are used herein to refer to a heme protein that has a sequence that occurs in nature.

In the context of this invention, the term "mutant" with respect to a mutant polypeptide or mutant polynucleotide is used interchangeably with "variant". A variant with respect to a given wildtype heme apoprotein reference sequence can include naturally occurring allelic variants. A "non-naturally" occurring heme apoprotein refers to a variant or mutant heme apoprotein polypeptide that is not present in a cell in nature and that is produced by genetic modification, e.g., using genetic engineering technology or mutagenesis techniques, of a native heme polynucleotide or polypeptide. A "variant" includes any heme protein comprising at least one amino acid mutation with respect to wild type. Mutations may include substitutions, insertions, and deletions. Variants include protein sequences that contain regions or segments of amino acid sequences obtained from more than one heme apoprotein sequence.

A polynucleotide or polypeptide is "heterologous" to an organism or a second polynucleotide or polypeptide sequence if it originates from a foreign species, or, if from the same species, is modified from its original form. For example, a "heterologous" sequence includes a native heme apoprotein having one or more mutations relative to the native heme apoprotein amino acid sequence; or a native heme apoprotein that is expressed in a host cell in which it does not naturally occur.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, y-carboxyglutamate, and O-phosphoserine Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified polypeptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acid is also meant to include—amino acids having L or D configuration at the ca-carbon.

A "non-natural amino acid" is included in the definition of an amino acid and refers to an amino acid that is not one of the 20 common naturally occurring amino acids or the rare naturally occurring amino acids e.g., selenocysteine or pyrrolysine. Other terms that may be used synonymously with the term "non-natural amino acid" is "non-naturally encoded amino acid," "unnatural amino acid," "non-naturally-occurring amino acid," and variously hyphenated and non-hyphenated versions thereof. The term "non-natural amino acid" includes, but is not limited to, amino acids which occur naturally by modification of a naturally encoded amino acid (including but not limited to, the 20 common amino acids or pyrrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine. Additionally, the term "non-natural amino acid" includes, but is not limited to, amino acids which do not occur naturally and may be obtained synthetically or may be obtained by modification of non-natural amino acids.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. Amino acid polymers may comprise entirely L-amino acids, entirely D-amino acids, or a mixture of L and D amino acids.

Heme polypeptide sequences that are substantially identical to a reference sequence include "conservatively modified variants." One of skill will recognize that individual changes in a nucleic acid sequence that alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Examples of amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R) and His (Histidine or H); an "aromatic or cyclic group" including Pro (Proline or P), Phe (Phenylalanine or F), Tyr (Tyrosine or Y) and Trp (Tryptophan or W); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T) and Cys (Cysteine or C). Within each group, subgroups can also be identified. For example, the group of charged or polar amino acids can be subdivided into sub-groups including: a "positively-charged sub-group" comprising Lys, Arg and His; a "negatively-charged sub-group" comprising Glu and Asp; and a "polar sub-group" comprising Asn and Gln. In another example, the aromatic or cyclic group can be sub-divided into subgroups including: a "nitrogen ring sub-group" comprising Pro, His and Trp; and a "phenyl sub-group" comprising Phe and Tyr. In another further example, the aliphatic group can be sub-divided into sub-groups, e.g., an "aliphatic non-polar sub-group" comprising Val, Leu, Gly, and Ala; and an "aliphatic slightly-polar sub-group" comprising Met, Ser, Thr and Cys. Examples of conservative mutations include amino acid substitutions of amino acids within the subgroups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —$NH_2$ can be maintained. In some embodiments, hydrophobic amino acids are substituted for naturally occurring hydrophobic amino acid, e.g., in the active site, to preserve hydrophobicity.

The terms "identical" or percent "identity," in the context of two or more polypeptide sequences (or two or more nucleic acids), refer to two or more sequences or subsequences that are the same or have a specified percentage of amino acid residues or nucleotides that are the same, e.g., at least 50% identity, preferably at least 60% identity, preferably at least 65%, 70%, 75%, 80%, 85%, 90%, 91%, 92%, 93%, 94%, 95%, 96%, 97%, 98%, 99% or 100% identity, over a specified region when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters are used. Alternatively, sequences may be aligned by hand to determine the percent identity.

The terms "corresponding to", "determined with reference to", or "numbered with reference to" when used in the context of the identification of a given amino acid residue in a polypeptide sequence, refers to the position of the residue of a specified reference sequence when the given amino acid sequence is maximally aligned and compared to the reference sequence. Thus, for example, a residue in a polypeptide "corresponds to" an amino acid at a position in SEQ ID NO: 1 when the residue aligns with the amino acid in SEQ ID NO: 1 when optimally aligned to SEQ ID NO: 1. The polypeptide that is aligned to the reference sequence need not be the same length as the reference sequence and may or may not contain a starting methionine.

"Forming a bond" refers to the process of forming a covalent bond such as a carbon-carbon bond, a carbon-nitrogen bond, a carbon-oxygen bond, or a covalent bond two other atoms.

"Carbene precursor" refers to a compound capable of generating a carbene, a carbon atom having only six valence shell electrons, including a lone pair of electrons, and represented by the formula: $R_2C$. For example, the carbene precursor can include a diazo group and have the formula $R_2C═N═N$ where $N_2$ is the leaving group the loss of which forms $R_2C$. Representative carbene precursors include, but are not limited to, α-diazoester, an α-diazoamide, an α-diazonitrile, an α-diazoketone, an α-diazoaldehyde, and an α-diazosilane. The carbenes are formed by coordination of the carbene precursor to the metal, generation of the metal-carbene complex, and reaction of this complex with the substrate in an inter- or intra-molecular fashion to form carbon-carbon bonds, including those in cyclopropyl groups.

"Nitrene precursor" refers to a compound capable of generating a nitrene, a nitrogen atom having only six valence shell electrons, including two lone pairs of electrons, and represented by the formula: RN. For example, the nitrene precursor can have the formula $RN═N═N$ where $N_2$ is the leaving group, the loss of which forms RN. Representative nitrene precursors include azides. The nitrenes are formed by coordination of the nitrene precursor to the metal, followed by reaction with the substrate to form amines.

"Substrate" refers to the compound that reacts with the carbene or nitrene to form the bond. Representative substrates contain an olefin or a C—H bond.

"Olefin" refers to a compound containing a vinyl group: —CR═CR—.

"C—H insertion" refers to the process of carbene insertion into a C—H bond to form a carbon-carbon bond, or nitrene insertion to form a carbon-nitrogen bond. Insertion of a nitrene into a C—H bond results in formation of an amine and can also be referred to as amination.

"Cyclopropanation" refers to the process of forming a cyclopropyl ring by carbene insertion into a double bound.

III. Catalyst Compositions

The present invention provides catalyst compositions of a metal-porphyrin complex and a heme apoprotein.

A. Porphyrin-Metal Complexes

The porphyrin-metal complex useful in the catalyst compositions of the present invention can be any suitable porphyrin and metal.

The porphyrin can be any suitable porphyrin. Representative porphyrins suitable in the present invention include, but are not limited to, pyropheophorbide-a, pheophorbide, chlorin e6, purpurin or purpurinimide. In some embodiments, the porphyrin can be pyropheophorbide-a. Representative structures are shown below:

| PORPHYRIN | STRUCTURE |
| --- | --- |
| Porphyrin | 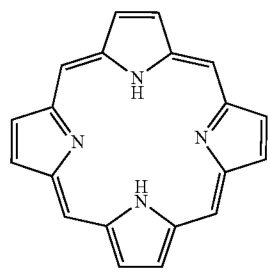 [SMILES: C1=Cc2cc3ccc(cc4nc(cc5ccc(cc1n2)[nH]5)C=C4)[nH]3] |
| Pyropheophorbide-a | 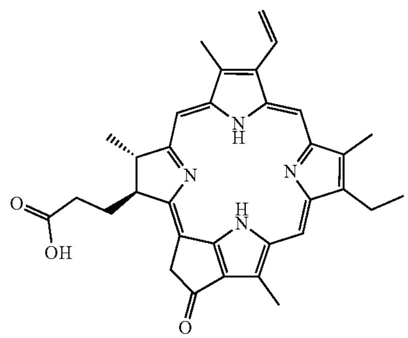 [SMILES: C=Cc1c(C)c2cc3nc(c4c5[nH]c(cc6nc(cc1[nH]2)C(C)=C6CC)c(C)c5C(=O)C4)[C@@H](CCC(=O)O)[C@@H]3C] |
| Pheophorbide | 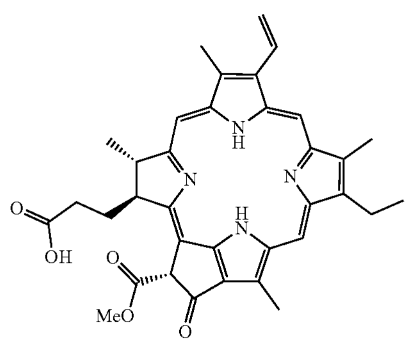 [SMILES: C=Cc1c(C)c2cc3nc(c4c5[nH]c(cc6nc(cc1[nH]2)C(C)=C6CC)c(C)c5C(=O)[C@@H]4C(=O)OC)[C@@H](CCC(=O)O)[C@@H]3C] |
| Chlorin e6 | 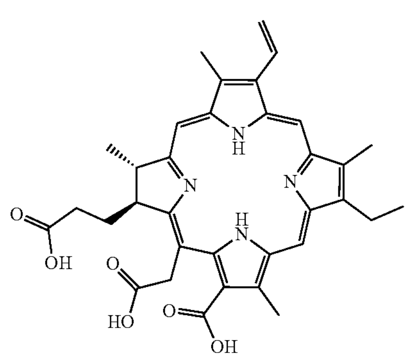 [SMILES: C=Cc1c(C)c2cc3nc(c(CC(=O)O)c4[nH]c(cc5nc(cc1[nH]2)C(C)=C5CC)c(C)c4C(=O)O)[C@@H](CCC(=O)O)[C@@H]3C] |

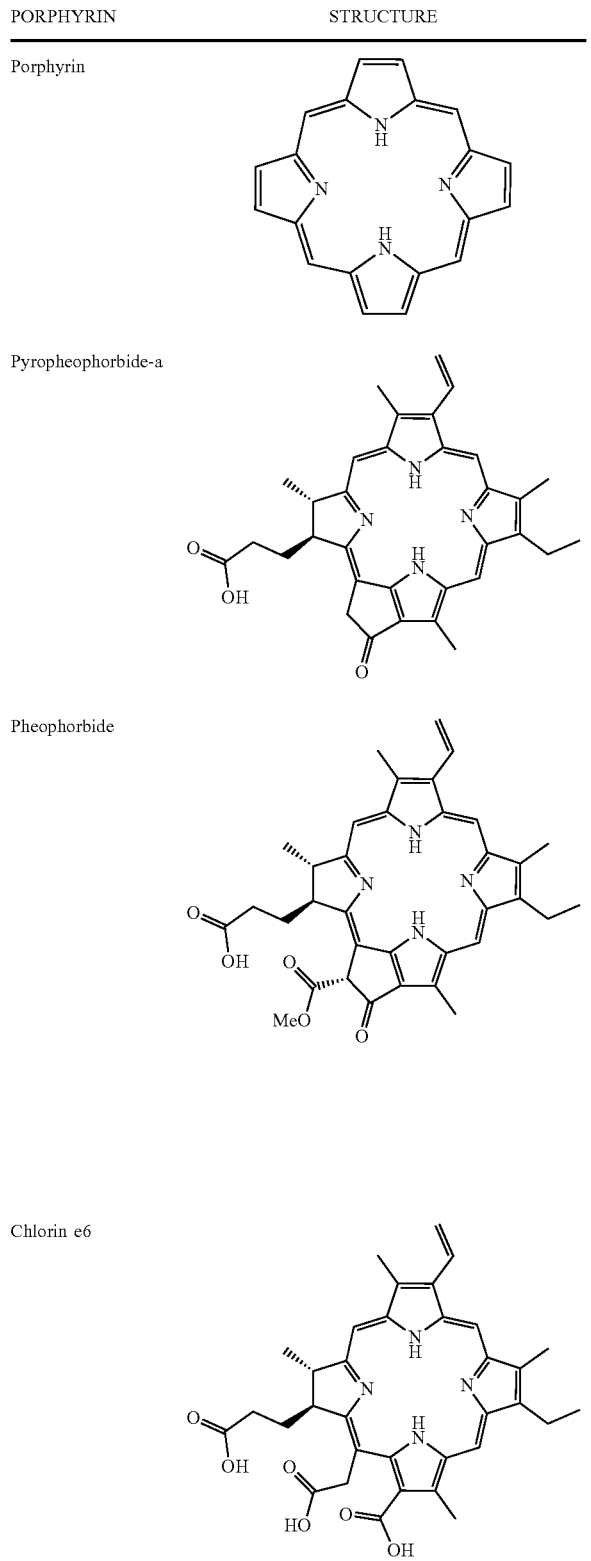

| PORPHYRIN | STRUCTURE |
| --- | --- |
| Purpurin | 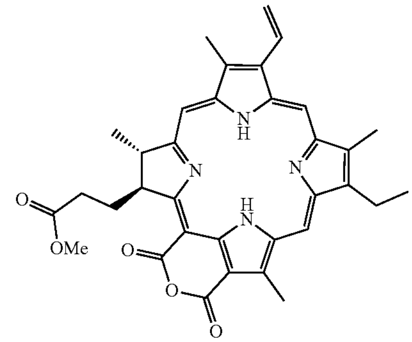 [SMILES: C=Cc1c(C)c2cc3nc(c4c5[nH]c(cc6nc(cc1[nH]2)C(C)=C6CC)c(C)c5C(=O)OC4=O)[C@@H](CCC(=O)OC)[C@@H]3C] |
| Purpurinimide | 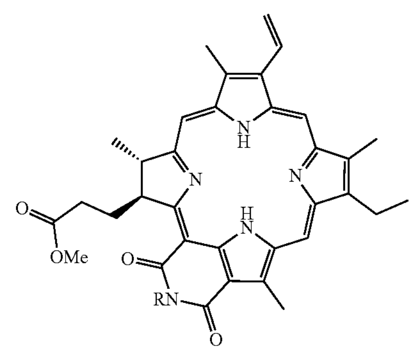 |

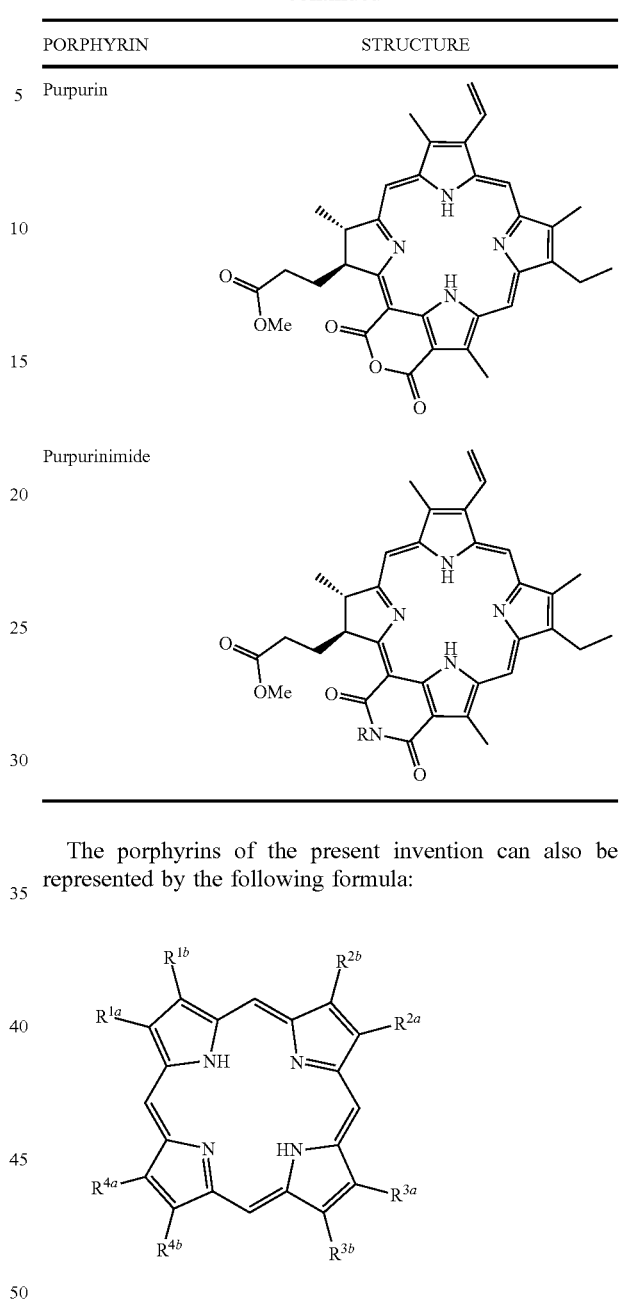

The porphyrins of the present invention can also be represented by the following formula:

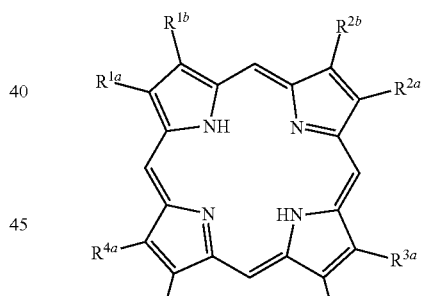

wherein $R^{1a}$, $R^{1b}$, $R^{2a}$, $R^{2b}$, $R^{3a}$, $R^{3b}$, $R^{4a}$ and $R^{4b}$ are each independently selected from the group consisting of hydrogen, $C_{1-6}$ alkyl, $C_{2-6}$ alkenyl, $C_{2-6}$ alkynyl, $C_{3-8}$ cycloalkyl and C6-10 aryl, wherein the alkyl is optionally substituted with —C(O)OR$^5$ wherein R$^5$ is hydrogen or $C_{1-6}$ alkyl. In some embodiments, $R^{1a}$, $R^{1b}$, $R^{2a}$, $R^{2b}$, $R^{3a}$ and $R^{4a}$ are each independently selected from the group consisting of hydrogen, $C_{1-6}$ alkyl and $C_{2-6}$ alkenyl, and $R^{3b}$ and $R^{4b}$ are each independently selected from the group consisting of $C_{1-6}$ alkyl, wherein the alkyl is substituted with —C(O)OR$^5$ wherein R$^5$ is hydrogen. In some embodiments, $R^{1a}$, $R^{1b}$, $R^{2a}$, $R^{2b}$, $R^{3a}$ and $R^{4a}$ are each independently selected from the group consisting of hydrogen, methyl, ethyl and ethenyl, and $R^{3b}$ and $R^{4b}$ are each —CH$_2$CH$_2$—C(O)OH. In some embodiments, the porphyrin can be selected from the group consisting of:

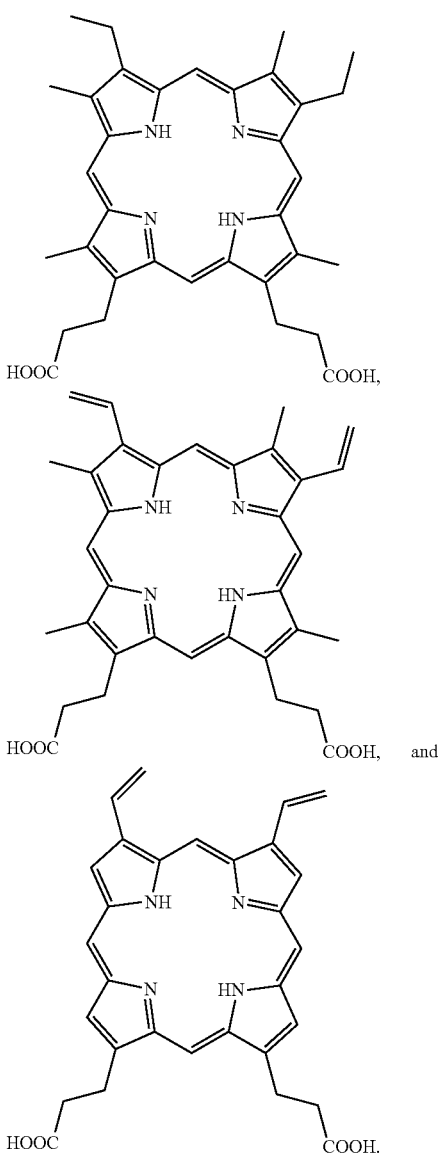

among others. Examples of ligands bound via carbon with a negative charge include, but are not limited to, alkyl, aryl, vinyl, alkynyl, and others. Examples of ligands bound through phosphorus include, but are not limited to, phosphines ($PR_3$), phosphites ($P(OR)_3$), phosphinites ($P(OR)(R)_2$), phosphonites ($P(OR)_2(R)$) and phosphoramides ($P(NR_2)_3$), where each R can independently be H, alkyl, alkenyl, alkynyl, aryl, etc. Ligands bound via phosphorous can also include mixtures of alkyl and alkoxo or amino groups. Examples of ligands bound through sulfur include, but are not limited to, thiols, thiolates and thioethers, among others.

In other examples, the ligand can be $C_{1-3}$ alkyl, —O—$C_{1-3}$ alkyl, halogen, —OH, —CN, —CO, —$NR_2$, —$PR_3$, $C_{1-3}$ haloalkyl, or pentafluorophenyl. In some embodiments, the ligand is absent. In some embodiments, the ligand is $C_{1-3}$ alkyl, —O—$C_{1-3}$ alkyl, halogen, —OH, —CN, —CO, —$NR_2$, —$PR_3$, $C_{1-3}$ haloalkyl, or pentafluorophenyl. In some embodiments, the ligand can be $C_{1-3}$ alkyl, halogen, —CO or —CN. In some embodiments, the ligand can be $C_{1-3}$ alkyl or halogen. In some embodiments, the ligand can be methyl, ethyl, n-propyl, isopropyl, F, Cl, or Br. In some embodiments, the ligand can be methyl ethyl, F, Cl, Br, CO or CN. In some embodiments, the ligand can be methyl, ethyl, F, Cl or Br. In some embodiments, the ligand can be methyl or chloro.

Any combination of metal and ligand can be used in the compositions of the present invention. In some embodiments, the M(L) can be Ir(Me), Ir(Cl), Fe(Cl), Co(Cl), Cu, Mn(Cl), Ru(CO) or Rh. In some embodiments, M(L) can be Ir(Me) or Ir(Cl). In some embodiments, M(L) can be Ir(Me).

The porphyrin and M(L) group can also form a complex, such as in the following structure:

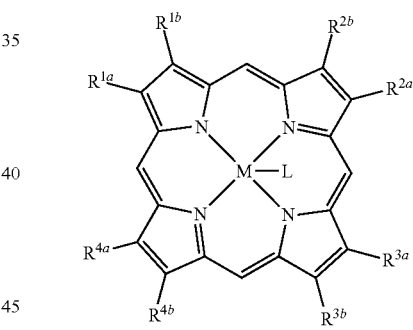

wherein $R^{1a}$, $R^{1b}$, $R^{2a}$, $R^{2b}$, $R^{3a}$, $R^{3b}$, $R^{4a}$ and $R^{4b}$ are as defined above. In some embodiments, the porphyrin-M(L) complex has the formula:

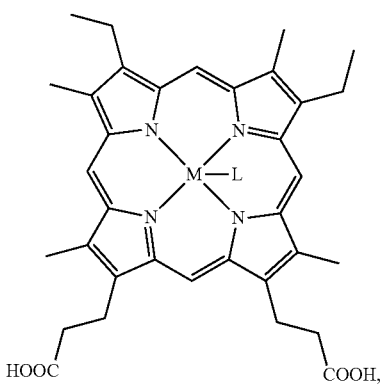

The metal M of the M(L) group can be any suitable metal, such as a transition metal. Representative metals include, but are not limited to, Ir, Pd, Pt, Ag, Fe, Mn, Ru, Co, Zn, Cu, Ni, Cr, Rh and Os. In some embodiments, the metal M can be Ir, Pd, Pt, Ag, Mn, Ru, Co, Zn, Cu, Ni, Cr, Rh and Os. In some embodiments, the metal M can be Ir, Co, Cu, Mn, Ru, or Rh. In some embodiments, the metal M can be Ir, Pd, Pt or Ag. In some embodiments, the metal M can be Ir. In some embodiments, the metal is other than Fe.

The ligand L can be absent or any suitable ligand. Examples of ligands bound via an oxygen with a formal negative charge include, but are not limited to, hydroxo, alkoxo, phenoxo, carboxylate, carbamate, sulfonate, and phosphate. Examples of ligands bound via an oxygen with a neutral charge include, but are not limited to, water, ethers, alcohols, phosphine oxide, and sulfoxides. Neutral examples of ligands bound via a nitrogen include, but are not limited to, amines, basic heterocycles, such as pyridine or imidazole. Examples of ligands bound via nitrogen with formal negative charges include, but are not limited to, amides like acetamide or trifluoroacetamide, heteroarenes like pyrrolide, -continued
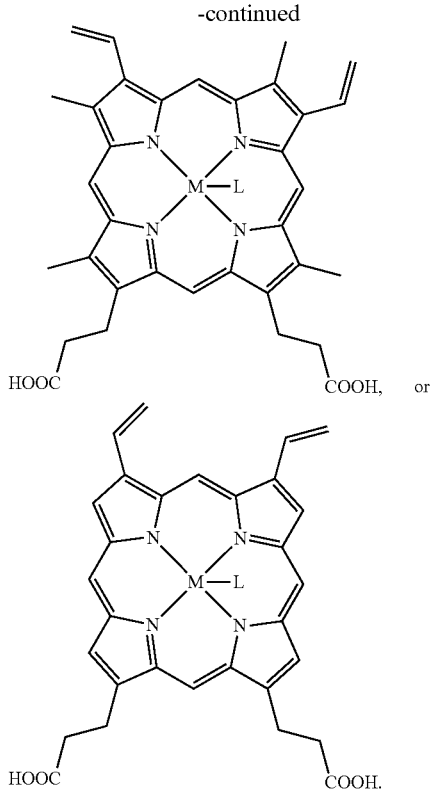
HOOC   COOH, or
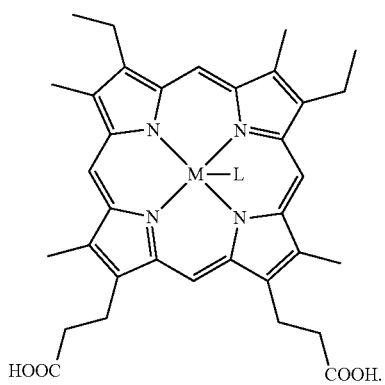
HOOC   COOH.
In some embodiments, the porphyrin-M(L) complex has the formula:
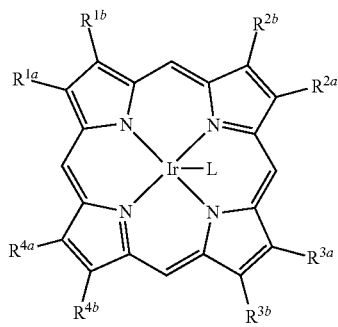
HOOC   COOH.
In some embodiments, the porphyrin-M(L) complex has the formula:
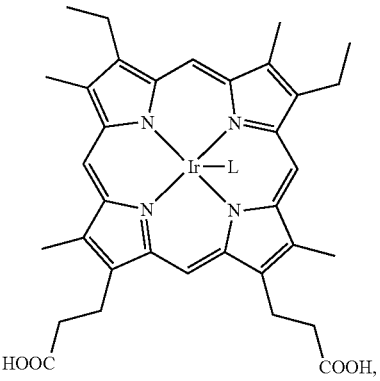
wherein $R^{1a}$, $R^{1b}$, $R^{2a}$, $R^{2b}$, $R^{3a}$, $R^{3b}$, $R^{4a}$ and $R^{4b}$ are as defined above.
In some embodiments, the porphyrin-Ir(L) complex has the formula:
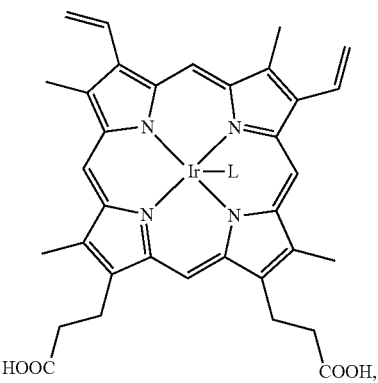
HOOC   COOH,
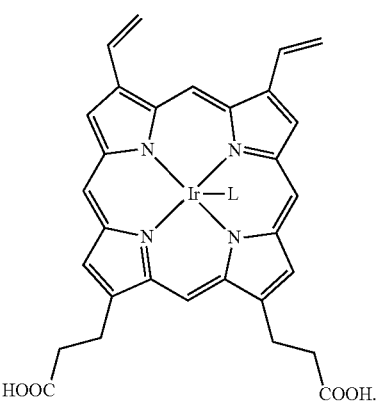
HOOC   COOH, or
HOOC   COOH.

In some embodiments, the porphyrin-Ir(L) complex has the formula:

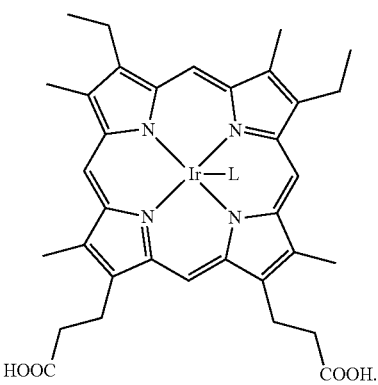

In some embodiments, the porphyrin-Ir(L) complex can have the formula:

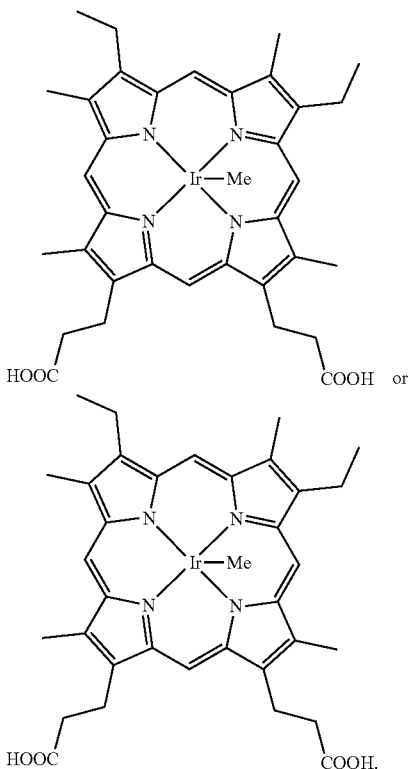

B. Heme Apoproteins

Heme proteins have diverse biological functions including oxygen transport, catalysis, active membrane transport, electron transport, and others. Various classes of heme proteins include, without limitation, globins (e.g., hemoglobin, myoglobin, neuroglobin, cytoglobin, leghemoglobin), cytochromes (e.g., a-, b-, and c-types, cd1-nitrite reductase, cytochrome oxidase), transferrins (e.g., lactotransferrin, serotransferrin, melanotransferrin), bacterioferririns, hydroxylamine oxidoreductase, nitrophorins, peroxidases (e.g., lignin peroxidase), cyclooxygenases (e.g., COX-1, COX-2, COX-3, prostaglandin H synthase), catalases, cytochrome P-450s, chloroperoxidases, PAS-domain heme sensors, H-NOX heme sensors (e.g., soluble guanylate cyclase, FixL, DOS, HemAT, and CooA), heme-oxygenases, and nitric oxide synthases. Data on heme protein structure and function has been aggregated into The Heme Protein Database. Any heme apoprotein can be bound to a porphyrin-M(L) of the present invention, wherein M is a metal other than iron. In some embodiments, the metal is Pd, Pt, or Ag. In some embodiments, the metal is Ir. In some embodiments, the metal is Mn, Ru, Co, Zn, Cu, Ni, Cr, Rh or Os. In some embodiments, the heme apoprotein is a cytochrome P450. In some embodiments, the heme apoprotein is myoglobin.

In some embodiments, a heme apoprotein suitable for use in the invention has a mutation near the active site of the heme apoprotein. The active sites of many heme proteins are known. Accordingly, heme protein active sites can be determined by sequence analysis, structural modeling based on known sequences, or a combination of such techniques. In some embodiments, a mutation near the active site is an amino acid substitution. In some embodiments, a mutation may be a deletion or insertion of amino acids, e.g., an insertion of 1, 2, 3, 4, or 5, or more, amino acids, or a deletion of 1, 2, 3, 4, or 5, or more, amino acids.

In some embodiments, a mutant heme apoprotein that is complexed with a porphyrin-M(L) of the invention, e.g., a Pd, Pt, or Ag-containing porphyrin-M(L) complex; or an Ir-containing porphyrin-M(L) complex, comprises one or more substitutions near the active site. In some embodiments, at least one or all of the amino acids substituted for the native amino acid(s) are hydrophobic amino acids, e.g., uncharged hydrophobic amino acids. In some embodiments, the substitution is D, E, F, G, H, I, L, M, S, T, V, W, or Y. In some embodiments, the porphyrin-M(L) complex comprises a metal selected from Mn, Ru, Co, Zn, Cu, Ni, Cr, Rh and Os.

In some embodiments, a mutation near the active site of heme apoprotein is at a position corresponding to an axial ligand position of a naturally occurring heme aproprotein. As used herein, the axial ligand position is the position of an amino acid residue, for example, a C residue in a P450, in the heme apoprotein that binds to the iron in the native heme protein. The axial ligand position for a heme protein can be determined by sequence alignment of active sites, structural alignments of a sequence to a known structure, e.g., a known crystallographic structure, and/or a combination of sequence analysis with protein modeling. In some embodiments, the mutation is a substitution, e.g., substitution of a hydrophobic amino acid for a native Cys residue of cytochrome P450 polypeptides. In some embodiments, the amino acid substituted for the native amino acid may be a small hydrophobic amino acid, such as Ala or Gly.

In some embodiments, the amino acid residue that coordinates the metal atom at the axial position of the heme apoprotein-metalloporphyrin is a naturally occurring amino acid selected from the group consisting of serine, threonine, cysteine, tyrosine, histidine, aspartic acid, glutamic acid, and selenocysteine. In other embodiments, the amino acid residue is a non-naturally occurring α-amino acid comprising a —SH, —NH2, —OH, =N—, —NC group, imidazolyl, or pyridyl group within its side chain. In some instances, a non-naturally occurring α-amino acid amino is para-aminophenylalanine, meta-amino-phenylalanine, para-mercaptomethyl-phenylalanine, meta-mercaptomethyl-phenylalanine, para-(isocyanomethyl)-phenylalanine, meta-(isocyanomethyl)-phenylalanine, 3-pyridyl-alanine, or 3-methyl-histidine.

Cytochrome P450 Heme Apoproteins

In some embodiments, the heme apoprotein employed in the invention is a cytochrome P450 enzyme. Cytochrome P450 enzymes are a superfamily of proteins that have been identified across bacterial, fungal, archaea, Protista, plant and animal kingdoms. In some embodiments, a cytochrome P450 enzyme apoprotein suitable for use in the invention is from a thermophile. Thousands of cytochrome p450 protein sequences are known and publicly available in P450 databases (e.g., Nelson, *Hum. Genomics* 4:59, 2009; Sirim et al., *BMC Biochem* 10:27, 2009; and Preissner et al., *Nucleic Acids Res.* 38:D237, 2010). The iron of the heme prosthetic group in a native P450 is linked to the P450 apoprotein via a cysteine thiolate ligand. This cysteine and several flanking residues are highly conserved in known cytochrome P450 proteins and have the formal PROSITE signature consensus pattern: [FW]-[SGNH]-x-[GD]-{F}-[RKHPT]-{P}-C-[LIVMFAP]-[GAD]. In some embodiments, a cytochrome P450 apoprotein employed in the invention is from a microbial source. P450 apoproteins in accordance with the present invention typically comprise at least one mutation near the active site. An active site can be determined based on structural information, e.g., crystallographic structure; sequence information; and/or modeling of sequences based on known structures. In some instances, a native amino acid residue close to the active site, e.g., an axial ligand position of a native P450 enzyme, is substituted with an amino acid, e.g., a hydrophobic amino acid. In some embodiments, a native amino acid close to the active site is substituted with a D, E, F, G, H, I, L, M, S, T, V, W, or Y. In some embodiments, the heme aprotein is any P450 enzyme having a mutation close to the active site with the proviso that the P450 enzyme is not a *Bacillus megaterium* P450; or variant of a *Bacillus megaterium* P450 that has a mutation near the active site.

In some embodiments, a P450 apoprotein, e.g., a CYP119 P450, or a variant thereof that is substantially identical to CYP119 region of sEQ ID NO:3, e.g. as described herein, is bound to a porphyrin-M(L) of the present invention, wherein M is a metal other than iron. In some embodiments, the metal is Pd, Pt, or Ag. In some instance, the metal, is Ir. In some embodiments, the metal is Mn, Ru, Co, Zn, Cu, Ni, Cr, Rh or Os.

In some embodiments, a cytochrome P450 apoprotein is CYP119 from *Sufolobus sofataricus* or a variant thereof. In some embodiments, the CYP119 apoprotein comprises the amino acid sequence of SEQ ID NO: 1, or comprises a variant of SEQ ID NO: 1, e.g., that has at least: 50%, 55%, 60%, 65%, 70%, 75%, 80%, 85%, 90%, 91%, 92%, 93%, 94%, 95%, 96%, 97%, 98%, or 99% identity to SEQ ID NO: 1. In some embodiments, an apoprotein suitable for use in the invention comprises at least 80%, at least 85%, at least 90%, or at least 95% identity to a 100 or 200 amino acid segment of SEQ ID NO: 1 that comprises the active site; or at least 70%, at least 80%, at least 85%, at least 90%, or at least 95% identity to a 300 amino acid segment of SEQ ID NO: 1 that comprises the active site.

In some embodiments, a cytochrome P450 apoprotein of the invention is a variant of SEQ ID NO: 1 that has a substitution at a position C317 as determined with reference to SEQ ID NO: 1. In some embodiments, the variant comprises a hydrophobic amino acid, other than C, at position 317. In some embodiments, the variant comprises A or G at position 317.

In some embodiments, a cytochrome P450 apoprotein variant comprises at least one or more substitutions at positions V254, L69, T213, A152, F310, L318, L155, or A209 as determined with reference to SEQ ID NO: 1. In some embodiments, the P450 apoprotein variant comprises at least one substitution T213G/V/A; L69V/Y/W/F, V254L/A/V/G; A209G, A152F/W/Y/L/V, L155 T/W/F/V/L, F310G/A/L, or L318G/A/F.

In some embodiments, the cytochrome p450 apoprotein variant comprises a substitution at C317 and at least one or more substitutions at positions V254, L69, T213, A152, F310, L318, L155, or A209 as determined with reference to SEQ ID NO:1. In some embodiments, a variant comprises at least one substitution C317/G/A; and at least one substitution T213G/V/A; L69V/Y/W/F, V254L/A/V/G; A209G, C317G/A, A152F/W/Y/L/V, L155T/W/F/V/L, F310G/A/L, or L318G/A/F.

In some embodiments, a variant comprises a substitution at C317 and at least two, at least three, or four substitutions at positions V254, L69, T213, A152, F310, L318, L155, or A209 as determined with reference to SEQ ID NO: 1. In some embodiments, a variant comprises at least one substitution C317/G/A; and two, three, or four substitutions selected from T213G/V/A; L69V/Y/W/F, V254L/A/V/G; A209G, C317G/A, A152F/W/Y/L/V, L155T/W/F/V/L, F310G/A/L, and L318G/A/F. In some embodiments, the variant is employed in a cyclopropanation reaction or a C—H insertion reaction.

In some embodiments, a variant comprises a substitution at C317 and five, six, seven, or all eight substitutions at positions V254, L69, T213, A152, F310, L318, L155, or A209 as determined with reference to SEQ ID NO: 1. In some embodiments, a variant comprises one substitution C317/G/A; and five, six, seven, or all eight substitutions T213G/V/A; L69V/Y/W/F, V254L/A/V/G; A209G, C317G/A, A152F/W/Y/L/V, L155T/W/F/V/L, F310G/A/L, or L318G/A/F. In some embodiments, the variant is employed in a cyclopropanation reaction or a C—H insertion reaction.

In some embodiments, a variant comprises substitutions at C317 and V254 as determined with reference to SEQ ID NO: 1. In some instances, the variant comprises the substitutions C317G and V254A.

In some embodiments, a variant comprises substitutions at C317, L69, and T213 as determined with reference to SEQ ID NO: 1. In some instances, the variant comprises the substitutions C317G, L69F, and T213V. In some instances, the variant comprises the substitutions C317G, L69W, and T213G.

In some embodiments, a variant comprises substitutions at C317, T213, and V254 as determined with reference to SEQ ID NO: 1. In some instances, the variant comprises the substitutions C317G, T213A, and V254L. In some instances, the variant comprises the substitutions C317G, T213G, and V254L.

In some embodiments, a variant comprises substitutions at C317 and T213 as determined with reference to SEQ ID NO: 1. In some instances, the variant comprises the substitutions C317G and T213A.

In some embodiments, a variant comprises a substitution at position C317, L69, T213, and V254 as determined with reference to SEQ ID NO: 1. In some embodiments, the variant comprises substitutions C317G, L69V, T213G and V254L. In some instances, the variant comprises substitutions C317G, L69F, T213G, and V254L. In some instances, the variant comprises substitutions C317G, L69F, T213V, and V254L.

In some embodiments, a variant comprises a substitution at positions C317, L69, T213, and F310 as determined with reference to SEQ ID NO:1. In some instances, the variant comprises substitutions C317G, L69W, T213G, and F310G.

In some embodiments, a variant comprises a substitution at positions C317, L69, T213, and A152 as determined with reference to SEQ ID NO:1. In some instances, the variant comprises substitutions C317G, L69Y, T213G, and A152W. In some instances, the variant comprises substitutions C317G, L69V, T213A, and A152W.

In some embodiments, a variant comprises a substitution at positions C317, L69, T213, and L318 as determined with reference to SEQ ID NO: 1. In some instances, the variant comprises substitutions C317G, L69W, T213G, and L318G.

In some embodiments, a variant comprises substitutions at C317, L155, and V254 as determined with reference to SEQ ID NO: 1. In some instances, the variant comprises substitutions C317G, L155W, and V254A.

In some embodiments, a variant comprises a substitution at position C317, L69, T213, and A152 as determined with reference to SEQ ID NO: 1. In some instances, the variant comprises C317G, L69F, T213V, and A152/L/V.

In some embodiments, a variant comprises a substitution at position C317, L69, T213, and L155 as determined with reference to SEQ ID NO:1. In some instances, the variant comprises C317G, L69F, T213V, and L155T. In some instances, the variant comprises C317G, L69F, T213V, and L155W.

In some embodiments, a variant comprises a substitution at position C317, T213, V254 and A152 as determined with reference to SEQ ID NO: 1. In some instances, the variant comprises C317G, T213G, V254L, and A152Y.

In some embodiments, a variant comprises a substitution at position C317, L69, T213, V254, and L155 as determined with reference to SEQ ID NO:1. In some instances, the variant comprises C317, L69F, T213V, V254L, and L155T In some embodiments, a variant comprises a substitution at position C317 and A209 as determined with reference to SEQ ID NO:1. In some instances, the variant comprises C317G and A209G.

In some embodiments, a variant comprises substitutions at C317, A254, F69, L318, and L155 as determined with reference to SEQ ID NO: 1. In some instances, the variant comprises C317G, V254A, F69L, L318F, and L155W.

In some embodiments, a variant comprises substitutions at C317, A254, F69, and L155 as determined with reference to SEQ ID NO: 1. In some instances, the variant comprises C317G, V254A, F69L, and L155W.

As explained above, a P450 apoprotein as described herein, e.g., a variant P450 apoprotein, can comprise one or more non-naturally occurring amino acids.

In some embodiments, a P450 apoprotein as set forth in each of the preceding paragraphs detailing P450 variants with reference to SEQ ID NO: 1 can be employed in a catalyst composition of the present invention in which the P450 apoprotein is bound to a porphyrin-M(L) complex in which the metal is Pd, Pt, or Ag. In some embodiments, a P450 apoprotein as set forth in each of the preceding paragraphs with reference to SEQ ID NO: 1 can be employed in a catalyst composition of the present invention in which the P450 apoprotein is bound to a porphyrin-M(L) complex in which the metal is Ir. In some embodiments, the metal is Mn, Ru, Co, Zn, Cu, Ni, Cr, Rh or Os.

In some embodiments, a catalyst composition of the present invention comprises a P450 apoprotein variant as described in each of the preceding paragraphs bound to a metal-porphyrin complex in which the metal is Ir. In some instances, the catalyst composition is used in a C—H insertion reaction. In some embodiments, the P450 apoprotein variant is substantially identical to the P450 region of SEQ ID NO:3, e.g., has at least: 50%, 60%, 70%, 80%, 85%, 90%, 95%, or greater, identity to the P450 region of SEQ ID NO:3; and comprises substitutions C317G, L69V, T213G, and V254L; substitutions C317G, T213G, and F310G; substitutions C317G, L69Y, T213G, and A152; substitutions C317G, T213A, and V254L; substitutions C317G, L69F, T213G, and V254L; substitutions C317G and T213A; substitutions C317G, L69Y, T213G, and A152W; substitutions C317G, L69W, T213G, and L318G; substitutions C317G, T213G, and V254L; substitutions C317G, L69V, T213G, and V254L; substitutions C317G, T213G, and V254L; substitutions C317G, L69W, and T213G; or substitutions C317G, L69V, T213A, V254L, and A152W; where the residues are numbered with reference to SEQ ID NO: 1. In some embodiments, such variants have at least 80% identity to the P450 region of SEQ ID NO:3. In some embodiments, such variants have at least 90% identity, or at least 95% identity, to the P450 region of SEQ ID NO:3.

In some embodiments, a catalyst composition of the present invention comprises a P450 apoprotein variant as described in each of the preceding paragraphs bound to a metal-porphyrin complex in which the metal is Ir. In some instances, the catalyst composition is used in a cyclopropanation reaction. In some embodiments, the P450 apoprotein variant is substantially identical to the P450 region of SEQ ID NO:3, e.g., has at least: 50%, 60%, 70%, 80%, 85%, 90%, 95%, or greater, identity to the P450 region of SEQ ID NO:3; and comprises substitutions C317G and V254A; C317G, L69F, and T213V; C317G, V254A, and L155w; C317G, L69F, T213V, and V254L; T213G and V254L; C317G, L69F, T213V, and L155T; C317G, V254A, and A152L; C317G, L69F, T213V, and V254L; C317G, V254A, and A152V; C317G, T213G, V254L, and A152Y; C317G, V254A, and L155W; C317G, L69F, T213V, V254L, and L155t; C317G, L69F, T213V, and L155W; C317G and A209G; C317G, L69F, T213V, and V254L; C317G, V254A, F69L, L318F, and L155W; C317G, L69F, T213V, and L155W; where the residues are numbered with reference to SEQ ID NO: 1. In some embodiments, such variants have at least 80% identity to the P450 region of SEQ ID NO:3. In some embodiments, such variants have at least 90% identity, or at least 95% identity, to the P450 region of SEQ ID NO:3.

Myoglobin Heme Apoproteins

In some embodiments, a heme apoprotein employed in the invention is a myoglobin. Myoglobin is an oxygen-binding hemoprotein found in the muscle tissue of vertebrates. The physiological role of myoglobin is to bind molecular oxygen with high affinity, providing a reservoir and source of oxygen to support the aerobic metabolism of muscle tissue. Native myoglobin contains a heme group (iron-protoporphyrin IX) which is coordinated at the proximal site via the imidazolyl group of a conserved histidine residue (e.g., His93 in sperm whale myoglobin). A distal histidine residue (e.g., His64 in sperm whale myoglobin) is present on the distal face of the heme ring, playing a role in favoring binding of $O_2$ to the heme iron center.

Myoglobin belongs to the globin superfamily of proteins and consists of multiple (typically eight) alpha helical segments connected by loops. In biological systems, myoglobin does not exert any catalytic function. Myoglobins have been well-studied structurally and many vertebrate myoglobin sequences are known in the art. An active site of a myoglobin can be determined based on structural information, e.g., crystallographic structure; sequence information; and/or modeling of sequences against known structures.

In some embodiments, the amino acid residue that coordinates the metal atom at the axial position of the myoglgbin apoprotein-metalloporphyrin is a naturally occurring amino acid selected from the group consisting of serine, threonine, cysteine, tyrosine, histidine, aspartic acid, glutamic acid, and selenocysteine. In other embodiments, the amino acid residue is a non-naturally occurring α-amino acid comprising a —SH, —NH2, —OH, =N—, —NC group, imidazolyl, or pyridyl group within its side chain. In specific embodiments, a non-naturally occurring α-amino acid amino is para-amino-phenylalanine, meta-amino-phenylalanine, para-mercaptomethyl-phenylalanine, meta-mercaptomethyl-phenylalanine, para-(isocyanomethyl)-phenylalanine, meta-(isocyanomethyl)-phenylalanine, 3-pyridylalanine, or 3-methyl-histidine.

In typical embodiments, a myoglobin apoprotein in accordance with the present invention comprises at least one mutation near the active site, e.g., a position that corresponds to an axial ligand position in a native myoglobin protein. In some embodiments, a native amino acid close to the active site is substituted with a hydrophobic amino acid. In some embodiments, a native amino acid is substituted with a D, E, F, G, H, I, L, M, S, T, V, W, or Y.

In some embodiments, a myoglobin e.g., a sperm whale myoglobin, or a mutant thereof, e.g. as described herein, is bound to a porphyrin-M(L) of the present invention, wherein M is a metal other than iron. In some embodiments, the metal is Pd, Pt, or Ag. In some instance, the metal, is Ir. In some embodiments, the metal is Mn, Ru, Co, Zn, Cu, Ni, Cr, Rh or Os.

In some embodiments, the myoglobin is a Physeter *microcephalus* (sperm whale) myoglobin, or a variant thereof. In some embodiments, a myoglobin apoprotein of the invention comprises the amino acid sequence of SEQ ID NO:2, or comprises a variant of SEQ ID NO:2, that is substantially identical to SEQ ID NO:2, i.e., it has at least: 50%, 55%, 60%, 65%, 70%, 75%, 80%, 85%, 90%, 91%, 92%, 93%, 94%, 95%, 96%, 97%, 98%, or 99% identity to SEQ ID NO:2. In some embodiments, an apoprotein suitable for use in the invention comprises at least 80%, at least 85%, at least 90%, or at least 95% identity to a 100 amino acid segment of SEQ ID NO:2 that comprises the active site; or at least 70%, at least 80%, at least 85%, at least 90%, or at least 95% identity to a 120 or 125 amino acid segment of SEQ ID NO:2 that comprises the active site.

In some embodiments, a myoglobin apoprotein of the invention is a variant that has a substitution, compared to the native myoglobin sequence, near the active site. In some embodiments, a myoglobin apoprotein of the present invention has a substitution at at least one of positions 93, 64, 43, 32, 33, 68, 97, 99, 103, and 108 as determined with reference to SEQ ID NO:2. In some embodiments, a variant comprises a hydrophobic amino acid at substitution at one, two, three, four, five, six, seven, eight, nine, or all 10 of the positions.

In some embodiments, a myoglobin variant of the present invention is substantially identical to SEQ ID NO:2 and comprises one or more substitutions at positions H93, H64, F43, F33, L32, V68, H97, I99, Y103, and S108 as determined with reference to SEQ ID NO:2. In some embodiments, the myoglobin apoprotein variant comprises at least one substitution H93A/G, H64L/V/A, F43L/Y/W/H/I, L32F, F33V/I, V68A/S/G/T, H97W/Y, I99F/V, Y103C, and S108C.

In some embodiments, a myoglobin variant comprises substitutions at position H93, H64, F43, and F33 as determined with reference to SEQ ID NO:2. In some instances, the variant comprises substitutions H93A, H64L, F43L, and F33V.

In some embodiments, a myoglobin variant comprises a substitution at each of positions H93, H64, F43, V68, and H97 as determined with reference to SEQ ID NO:2. In some instances, the variant comprises substitutions H93A, H64V, F43Y, V68A, and H97W. In some instances, the variant comprises substitutions H93A, H64L, F43W, V68A, and H97Y.

In some embodiments, a myoglobin variant comprises substitutions at positions H93, H64, F43, and I99 as determined with reference to SEQ ID NO:2. In some instances, the variant comprises substitutions H93G, H64L, F43L, and I99F.

In some embodiments, a myoglobin variant comprises substitutions at position H93, H64, V68, 103, and 108 as determined with reference to SEQ ID NO:2. In some instances, the variant comprises substitutions H93A, H64V, V68A, Y103C, and S108C.

In some embodiments, a myoglobin variant comprises substitutions at positions H93, H64, F43, V68, and F33 as determined with reference to SEQ ID NO:2. In some instances, the variant comprises substitutions H93A, H64L, F43W, V68A, and F33I.

In some embodiments, a myoglobin variant comprises substitutions at positions H93, H64, F43, V68, as determined with reference to SEQ ID NO:2. In some instances, the variant comprises substitutions H93A, H64V, F43H, and V68S. In some instances, the variant comprises substitutions H93A, H64A, F43W, and V68G. In some instances, the variant comprises substitutions H93A, H64A, F43W, and V68T. In some instances, the variant comprises substitutions H93A, H64A, F43I, and V68T.

In some embodiments, a myoglobin variant comprises substitutions at position H93, H64, V68, F33, and I99 as determined with reference to SEQ ID NO:2. In some instances, the variant comprises substitutions H93G, H64L, V68A, and I99V. In some instances, the variant comprises substitutions H93A, H64L, V68A, and I99V.

In some embodiments, a myoglobin variant comprises substitutions at position H93, H64, V68, F33, and H97 as determined with reference to SEQ ID NO:2. In some instances, the variant comprises substitutions H93A, H64V, V68A, F33V and H97Y.

In some embodiments, a myoglobin variant comprises substitutions at position H93, H64, V68, L32, and H97 as determined with reference to SEQ ID NO:2. In some instances, the variant comprises substitutions H93G, H64L, V68A, L32F, and H97Y.

As explained above, a myoglobin apoprotein variant as described herein can comprise one or more non-naturally occurring amino acids.

In some embodiments, a myoglobin apoprotein as specifically set forth in each of the preceding paragraphs detailing myoglobin variants can be employed in a catalyst composition of the present invention in which myoglobin apoprotein is bound to a porphyrin-M(L) complex in which the metal is Pd, Pt, or Ag. In some embodiments, a myoglobin apoprotein as specifically set forth in each of the preceding paragraphs can be employed in a catalyst composition of the present invention in which myoglobin apoprotein is bound to a porphyrin-M(L) complex in which the metal is Ir. In some embodiments, the metal is Pd, Pt, or Ag. In some embodiments, the metal is Mn, Ru, Co, Zn, Cu, Ni, Cr, Rh or Os.

In some embodiments, a catalyst composition of the present invention comprises a myoglobin apoprotein variant as described in each of the preceding paragraphs bound to a phorphyrin-M(L) complex in which the metal is Ir. In some embodiments, the catalyst composition is used in a C—H insertion reaction. In some embodiments, the myoglobin apoprotein variant is substantially identical to the myoglobin region of SEQ ID NO:6, e.g., has at least: 50%, 60%, 70%, 80%, 85%, 90%, 95%, or greater, identity to the myoglobin region of SEQ ID NO:6; and comprises substitutions H93A, H64L, F43L, and F33V; substitutions H93A, H64V, F43Y, V68A, and H97W; substitutions H93A, H64L, F43W, V68A, and H97Y; substitutions H93G, H64L, F43L, and I99F; substitutions H93A, H64V, V68A, Y103C, and S108C; substitutions H93A, H64L, F43W, V68A, and F33I; substitutions H93A, H64V, F43H, and V68S; substitutions H93A, H64A, F43W, and V68G; substitutions H93A, H64A, F43W, and V68T; substitutions H93A, H64A, F43I, and V68T; substitutions H93G, H64L, V68A, and I99V substitutions H93A, H64L, V68A, and I99V; substitutions H93A, H64V, V68A, F33V and H97Y; or substitutions H93G, H64L, V68A, L32F, and H97Y; where the residues are numbered with reference to SEQ ID NO:2. In some embodiments, such variants have at least 80% identity to the myoglobin region of SEQ ID NO:6. In some embodiments, such variants have at least 90% identity, or at least 95% identity, to the myoglobin region of SEQ ID NO:6.

As explained above, a myoglobin apoprotein variant as described herein can comprise one or more non-naturally occurring amino acids.

C. Catalyst Compositions

Suitable combinations of porphyrin-metal complexes described above and heme apoproteins described above are useful in the catalyst compositions of the present invention.

In some embodiments, the present invention provides a catalyst composition comprising a porphyrin, M(L), wherein the porphyrin and M(L) form a complex, M is a metal selected from the group consisting of Ir, Pd, Pt and Ag, L is absent or a ligand, and a heme apoprotein, wherein the porphyrin-M(L) complex is bound to the heme apoprotein. In some embodiments, the present invention provides a catalyst composition comprising a porphyrin, M(L), wherein the porphyrin and M(L) form a complex, M is a metal selected from the group consisting of Ir, Pd, Pt and Ag, L is absent or a ligand selected from the group consisting of $C_{1-3}$ alkyl, —O—$C_{1-3}$ alkyl, halogen, —OH, —CN, —CO, —$NR_2$, —$PR_3$, $C_{1-3}$ haloalkyl, and pentafluorophenyl, each R is independently selected from the group consisting of H and $C_{1-3}$ alkyl, and a heme apoprotein, wherein the porphyrin-M(L) complex is bound to the heme apoprotein.

In some embodiments, the present invention provides a catalyst composition comprising a porphyrin, M(L), wherein the porphyrin and M(L) form a complex, M is a metal selected from the group consisting of Ir, Pd, Pt, Ag, Mn, Ru, Co, Zn, Cu, Ni, Cr, Rh and Os, L is absent or a ligand, and a mutant heme apoprotein having a mutation close to the active site, e.g., a myoglobin or P450 having a mutation close to the active site, wherein the porphyrin-M(L) complex is bound to the heme apoprotein. In some embodiments, the present invention provides a catalyst composition comprising a porphyrin, M(L), wherein the porphyrin and M(L) form a complex, M is a metal selected from the group consisting of Ir, Pd, Pt, Ag, Mn, Ru, Co, Zn, Cu, Ni, Cr, Rh and Os, L is absent or a ligand selected from the group consisting of $C_{1-3}$ alkyl, —O—$C_{1-3}$ alkyl, halogen, —OH, —CN, —CO, —$NR_2$, —$PR_3$, $C_{1-3}$ haloalkyl, and pentafluorophenyl, each R is independently selected from the group consisting of H and $C_{1-3}$ alkyl, and a mutant heme apoprotein having a mutation close to the active site, e.g., a myoglobin or 450, wherein the porphyrin-M(L) complex is bound to the heme apoprotein.

In some embodiments, the porphyrin-M(L) complex has the formula:

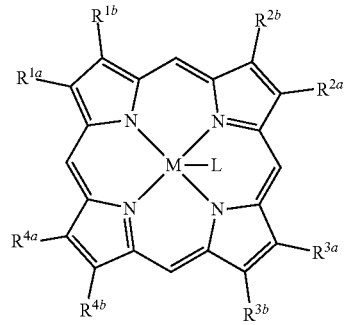

wherein M can be Ir, Pd, Pt, Ag, Mn, Ru, Co, Zn, Cu, Ni, Cr, Rh and Os, L can be absent or a ligand, and $R^{1a}$, $R^{1b}$, $R^{2a}$, $R^{2b}$, $R^{3a}$, $R^{3b}$, $R^{4a}$ and $R^{4b}$ can each independently be hydrogen, $C_{1-6}$ alkyl, $C_{2-6}$ alkenyl, $C_{2-6}$ alkynyl, $C_{3-8}$ cycloalkyl or $C_{6-10}$ aryl, wherein the alkyl can optionally be substituted with —C(O)$OR^5$ wherein $R^5$ is hydrogen or $C_{1-6}$ alkyl. In some embodiments, M can be Ir, Co, Cu, Mn, Ru, or Rh, L can be absent or a ligand that can be methyl ethyl, F, Cl, Br, CO or CN, and $R^{1a}$, $R^{1b}$, $R^{2a}$, $R^{2b}$, $R^{3a}$, $R^{3b}$, $R^{4a}$ and $R^{4b}$ can each independently be hydrogen, $C_{1-6}$ alkyl, $C_{2-6}$ alkenyl, $C_{2-6}$ alkynyl, $C_{3-8}$ cycloalkyl or $C_{6-10}$ aryl, wherein the alkyl can optionally be substituted with —C(O)$OR^5$ wherein $R^5$ is hydrogen or $C_{1-6}$ alkyl.

In some embodiments, the catalyst composition includes the porphyrin-Ir(L) complex having the structure:

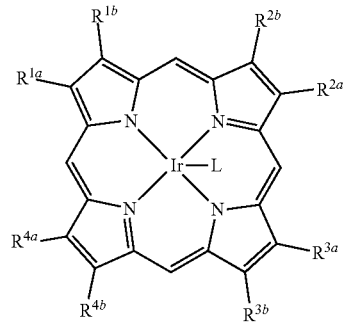

wherein L, $R^{1a}$, $R^{1b}$, $R^{2a}$, $R^{2b}$, $R^{3a}$, $R^{3b}$, $R^{4a}$ and $R^{4b}$ are as defined above.

In some embodiments, the catalyst composition includes the porphyrin-Ir(L) complex having the structure:

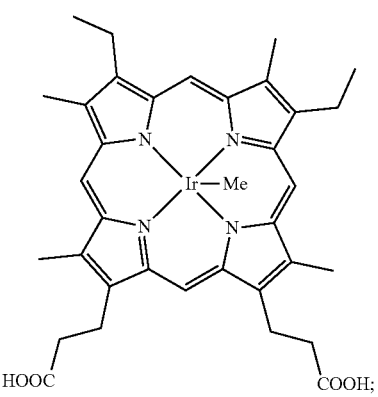

the heme apoprotein is myoglobin.

In some embodiments, the catalyst composition includes the porphyrin-Ir(L) complex having the structure:

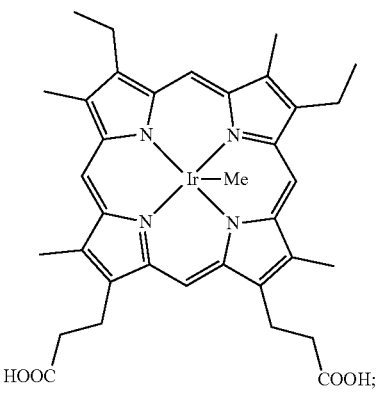

the heme apoprotein is P450.

1. Preparation of Heme Apoprotein-M(L) Complex

Heme apoprotein-ML-complexes can be prepared according to any method, for example, removal of the heme cofactor from the heme polypeptide followed by refolding of the apoprotein in the presence of the metalloporphyrin (Yonetani and Asakura 1969; Yonetani, Yamamoto et al. 1974; Hayashi, Dejima et al. 2002; Hayashi, Matsuo et al. 2002; Heinecke, Yi et al. 2012). Alternatively, heme apoprotein-ML-complexes can be obtained via recombinant expression of the heme polypeptide in bacterial strains that are capable of uptaking the metalloporphyrin from the culture medium (Woodward, Martin et al. 2007; Bordeaux, Singh et al. 2014).

In some embodiments, the heme apoprotein-metal complex is produced by expressing the heme apoprotein in an expression system, e.g., an $E. coli$ expression system, in which the cells are grown in minimal media lacking added Fe to inhibit the biosynthesis of hemin; and are grown at low temperature to mitigate the stability of the apoprotein form. The expressed aproteins are then purified and reconstituted quantitatively by addition of stoichiometric amounts of the desired metallo porphyrin complex. In some embodiments, the heme apoprotein may be fused to a sequence to increase stability of the expressed protein, e.g., an mOCR stability tag. In some embodiments, the heme apoprotein is expressed with a tag, e.g., a His tag, for purification. In some embodiments, the tag is joined to the apoprotein by a cleavable linker. In one aspect, the invention provides a heme apoprotein produced by expressing the heme apoprotein in cells that are grown in minimal media lacking added Fe at a low temperature, e.g., in a range of from about 15° C. to about 30° C., e.g., from about 20° C. to about 25° C.; purifying the heme apoprotein; and reconstituting the heme apoprotein with a metallo porphyrin complex that contains a metal selected from the group consisting of Ir, Pd, Pt, Ag, Mn, Ru, Co, Zn, Cu, Ni, Cr, Rh and Os. In some embodiments, the heme apoprotein is reconstituted with a metal selected from the group consisting of Ir, Pd, Pt, or Ag. In some embodiments, the heme apoprotein is reconstituted with Ir.

Heme apoproteins can be expressed using any number of expression vectors. Examples of suitable recombinant expression vectors include but are not limited to, chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses and many others. A person skilled in the art will be able to select suitable expression vectors for a particular application, e.g., the type of expression host (e.g., in vitro systems, prokaryotic cells or eukaryotic cells, including bacterial cells, cyanobacteria, algae and microalgae; archaea, yeast, insect, mammalian, fungal, or plant cells) and the expression conditions selected.

In some embodiments, a host cell for expression of a heme aprotein is a microorganism, such as a bacterial or yeast host cell. In some embodiments of the invention, the host cell is a proteobacteria. In some embodiments of the invention, the host cell is a bacterial host cell from a species of the genus $Planctomyces$, $Bradyrhizobium$, $Rhodobacter$, $Rhizobium$, $Myxococcus$, $Klebsiella$, $Azotobacter$, $Escherichia$, $Salmonella$, $Pseudomonas$, $Caulobacter$, $Chlamydia$, $Acinetobacter$, $Acetobacter$, $Enterobacter$, $Sinorhizobium$, $Vibrio$, or $Zymomonas$. In some embodiments, the host cell is $E. coli$. In some embodiments, the host cells include species assigned to the $Azotobacter$, $Erwinia$, $Bacillus$, $Clostridium$, $Enterococcus$, $Lactobacillus$, $Lactococcus$, $Oceanobacillus$, $Proteus$, $Serratia$, $Shigella$, $StaphLococcus$, $Streptococcus$, $Streptomyces$, $Vitreoscilla$, $Synechococcus$, $Synechocystis$, and $Paracoccus$ taxonomical classes. In some embodiments, the host cell is a yeast. Examples of yeast host cells include, without limitation, $Candida$, $Hansenula$, $Kluyveromyces$, $Pichia$, $Saccharomyces$, $Schizosaccharomyces$, or $Yarrowia$ host cells.

In one aspect, the invention further provides host cells that are engineered to express a heme apoprotein, e.g., a variant P450 or variant myoglobin of the present invention; and/or lysates or extracts of such host cells.

Variants of heme apoprotein can be generated via mutagenesis of a polyncucletoide that encodes the heme apoportin of interest. Suitable mutagenesis techniques include, but are not limited to, site-directed mutagenesis, site-saturation mutagenesis, random mutagenesis, cassette-mutagenesis, DNA shuffling, homologous recombination, non-homologous recombination, site-directed recombination, and the like. Detailed description of art-known mutagenesis methods can be found, among other sources, in U.S. Pat. Nos. 5,605,793; 5,830,721; 5,834,252; WO 95/22625; WO 96/33207; WO 97/20078; WO 97/35966; WO 98/27230; WO 98/42832; WO 99/29902; WO 98/41653; WO 98/41622; WO 98/42727; WO 00/18906; WO 00/04190; WO 00/42561; WO 00/42560; WO 01/23401; WO 01/64864.

Heme apoproteins expressed in a host expression system, such as, for example, in a host cell, can be isolated and purified using any one or more of the well-known techniques for protein purification, including, among others, cell lysis via sonication or chemical treatment, filtration, salting-out, and chromatography (e.g., ion-exchange chromatography, gel-filtration chromatography, etc.).

Variants can be assessed for activity using any suitable assay that assesses the desired catalytic activity, e.g., assays as described herein.

In one aspect, the invention further provide kits comprising heme apoprotein-metalloporphyrin complexes of the present invention, e.g., Ir-containing metalloporphyrin complexes, or metalloporphyrin complexes containing Pt, Pd, or Ag. Such kits can include a single catalyst composition or multiple catalyst compositions. In some embodiments, the catalyst compositions is linked to a solid support. In some embodiments, the kit further comprises reagents for conducting the desired reactions, substrates for assessing activity, and the like.

In some embodiments, a heme apoprotein-metalloporphyrin complex of the present invention can be covalently or non-covalently linked to a solid support. Examples of solid supports include but are not limited to supports such as polystyrene, polyacrylamide, polyethylene, polypropylene, polyethylene, glass, silica, controlled pore glass, metals and the like. The configuration of the solid support can be in the form of beads, spheres, particles, gel, a membrane, or a surface.

IV. Bond Formation

The catalyst compositions of the present invention can be used to prepare a variety of new bonds, including carbon-carbon and carbon-nitrogen bonds. The new bond can be formed by insertion of a carbene into a C—H bond or addition to an olefin group to form a carbon-carbon bond. Insertion into a C—H bond can be intermolecular or intramolecular insertion of the carbene. Addition to an olefin provides a cyclopropyl group. The new bond can also be formed by insertion of a nitrene into a C—H bond to form a carbon-nitrogen bond, i.e., an amine.

In some embodiments, the present invention provides a method of forming a bond, comprising forming a reaction mixture comprising a catalyst composition of the present invention, a reactant selected from a carbene precursor or a nitrene precursor, and a substrate comprising an olefin or a C—H group, under conditions where the reactant forms a carbene or nitrene which inserts into the alkene or C—H bond of the substrate to form the bond between the reactant and the substrate.

The reactant can be any suitable carbene or nitrene precursor. A carbene precursor can be any group capable of generating a carbene. Representative carbene precursors include the diazo

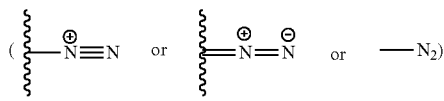

group. When the carbene precursor is a diazo group, the carbene precursor can have the formula:

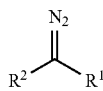

wherein
R$^1$ is independently selected from the group consisting of halo, cyano, —C(O)OR$^{1a}$, —C(O)N(R$^7$)$_2$, —C(O)R$^8$, —C(O)C(O)OR$^8$, and —Si(R$^8$)$_3$;
R$^2$ is independently selected from the group consisting of H, C$_{1-18}$ alkyl, C$_{1-18}$ substituted alkyl, C$_{6-10}$ aryl, C$_{6-10}$ substituted aryl, C$_{5-10}$ heteroaryl, C$_{5-10}$ substituted heteroaryl, halo, cyano, —C(O)OR$^{2a}$, —C(O)N(R$^7$)$_2$, —C(O)R$^8$, —C(O)C(O)OR$^8$, —Si(R$^8$)$_3$, and —SO$_2$(R$^8$);
R$^{1a}$ and R$^{2a}$ are each independently selected from the group consisting of H and C$_{1-18}$ alkyl; and R$^7$ and R$^8$ are each independently selected from the group consisting of H, C$_{1-12}$ alkyl, C$_{2-12}$ alkenyl, C$_{3-10}$ cycloalkyl, C$_{3-10}$ substituted cycloalkyl, C$_{3-12}$ heterocycloalkyl, C$_{3-12}$ substituted heterocycloalkyl, C$_{6-10}$ aryl, C$_{6-10}$ substituted aryl, C$_{5-10}$ heteroaryl and C$_{5-10}$ substituted heteroaryl.

The carbene precursor can be an α-diazoester, an α-diazoamide, an α-diazonitrile, an α-diazoketone, an α-diazoaldehyde, or an α-diazosilane, which can also be represented by the formulas below:

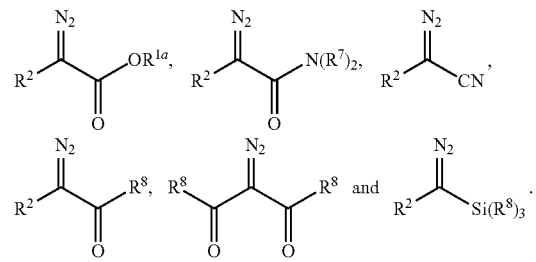

In some embodiments, R$^2$ can be hydrogen. In some embodiments, R$^2$ can be C$_{1-18}$ alkyl, C$_{1-18}$ substituted alkyl, C$_{6-10}$ aryl, C$_{6-10}$ substituted aryl, C$_{5-10}$ heteroaryl, C$_{5-10}$ substituted heteroaryl, halo, cyano, —C(O)OR$^{2a}$, —C(O)N(R$^7$)$_2$, —C(O)R$^8$, —C(O)C(O)OR$^8$, or —Si(R$^8$)$_3$. In some embodiments R$^2$ can be C$_{6-10}$ substituted aryl or C$_{5-10}$ substituted heteroaryl, wherein the aryl and heteroaryl groups are substituted with 1 to 5 R$^{2b}$ groups each independently selected from the group consisting of C$_{1-6}$ alkyl, C$_{1-6}$ alkoxy, C$_{1-6}$ alkyl-C$_{6-10}$ aryl and C$_{1-6}$ alkoxy-C$_{6-10}$ aryl.

In some embodiments, the carbene precursor has the formula:

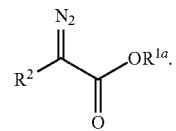

In some embodiments, R$^2$ can be C$_{6-10}$ substituted aryl or C$_{5-10}$ substituted heteroaryl, wherein the aryl and heteroaryl groups are substituted with 1 to 5 R$^{2b}$ groups each independently selected from the group consisting of C$_{1-6}$ alkyl, C$_{1-6}$ alkoxy, and C$_{1-6}$ alkyl-C$_{6-10}$ aryl. In some embodiments, R$^2$ can be phenyl, substituted with 1 to 5 R$^{2b}$ groups each independently selected from the group consisting of C$_{1-6}$ alkyl, C$_{1-6}$ alkoxy, and C$_{1-6}$ alkyl-C$_{6-10}$ aryl. In some embodiments, R$^2$ can be phenyl substituted with ethyl, propyl, methoxy, ethoxy, or benzyloxy.

In some embodiments, the carbene precursor has the formula:

When the reactant is a nitrene precursor, the nitrene can be formed from any suitable compound. Representative nitrene precursors can be azides, sulphonamides, tosylprotected sulphonamides, and phosphoramidates. When the nitrene precursor is an azide, the azide can have the following formula:

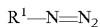

wherein $R^1$ is independently selected from the group consisting of $C_{1-18}$ alkyl, $C_{6-10}$ aryl, $C_{5-10}$ heteroaryl, halo, cyano, —C(O)OR$^{1a}$, —C(O)N(R$^7$)$_2$, —C(O)R$^8$, —C(O)C(O)OR$^8$, —Si(R$^8$)$_3$, SO$_2$R$^8$ and —P(O)(OR$^8$)$_2$ and $R^{1a}$ is selected from the group consisting of H and $C_{1-18}$ alkyl; and $R^7$ and $R^8$ are each independently selected from the group consisting of H, $C_{1-12}$ alkyl, $C_{2-12}$ alkenyl, $C_{3-10}$ cycloalkyl, $C_{3-10}$ substituted cycloalkyl, $C_{3-12}$ heterocycloalkyl, $C_{3-12}$ substituted heterocycloalkyl, $C_{6-10}$ aryl, $C_{6-10}$ substituted aryl, $C_{5-10}$ heteroaryl and $C_{5-10}$ substituted heteroaryl.

In some embodiments, the nitrene precursor can be a sulfonyl azide, a sulfinyl azide, keto azide, ester azide, phosphono azide and phosphino azide. In some embodiments, the nitrene precursor can be sulfonyl azide. In some embodiments, the nitrene precursor can have the structure:

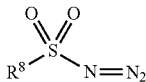

wherein $R^8$ is selected from the group consisting of H, $C_{1-12}$ alkyl, $C_{2-12}$ alkenyl, $C_{3-10}$ cycloalkyl, $C_{3-10}$ substituted cycloalkyl, $C_{3-12}$ heterocycloalkyl, $C_{3-12}$ substituted heterocycloalkyl, $C_{6-10}$ aryl, $C_{6-10}$ substituted aryl, $C_{5-10}$ heteroaryl and $C_{5-10}$ substituted heteroaryl.

The substrate can be any suitable group capable of reacting with the carbene or nitrene to form a new bond. For example, the substrate can include an activated C—H bond, an olefin, an activated N—H bond, an activated S—H bond or an activated Si—H bond. The substrate can be independent of the reactant such that the bond formation is an intermolecular bond formation between the reactant and the substrate. Alternatively, the substrate can be a part of the reactant such that the bond formation is an intramolecular bond formation.

A. C—H Insertion and Amination

Activated C—H bonds include, but are not limited to, benzylic C—H bonds, those adjacent to heteroatoms such as O, N or S, as well as alkyl C—H bonds. Other C—H bonds are also useful in the methods of the present invention. Substrates including an activated C—H bond can have the following formula:

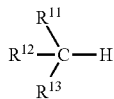

wherein $R^{11}$, $R^{12}$ and $R^{13}$ are each independently selected from the group consisting of H, $C_{1-6}$ alkyl, $C_{2-6}$ alkenyl, $C_{2-6}$ alkynyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —NR$^{11a}$R$^{11b}$, —C(O)R$^{11a}$, —C(O)OR$^{11a}$, —C(O)NR$^{11a}$R$^{11b}$, —SR$^{11a}$, —S(O)R$^{11a}$, —S(O)$_2$R$^{11a}$, $C_{3-8}$ cycloalkyl, $C_{3-8}$ heterocycloalkyl, $C_{6-10}$ aryl, and $C_{5-10}$ heteroaryl, optionally substituted with 1 to 5 R$^{11c}$ groups each independently selected from the group consisting of halogen, haloalkyl, haloalkoxy, —OR', =O, —OC(O)R', —(O)R', —O$_2$R', —ONR'R", —OC(O)NR'R", =NR', =N—OR', —NR'R", —NR"C(O)R', —NR'—(O)NR"R'", —NR"C(O)OR', —NH—(NH$_2$)=NH, —NR'C(NH$_2$)=NH, —NH—(NH$_2$)=NR', —SR', —S(O)R', —S(O)$_2$R', —S(O)$_2$NR'R", —NR'S(O)$_2$R", —N$_3$ and —NO$_2$. R', R" and R'" each independently refer to hydrogen, unsubstituted alkyl, such as unsubstituted $C_{1-6}$ alkyl. Alternatively, R' and R", or R" and R'", when attached to the same nitrogen, are combined with the nitrogen to which they are attached to form a heterocycloalkyl or heteroaryl ring, as defined above.

The carbon of the C—H bond can be a primary carbon, secondary carbon or tertiary carbon. In some embodiments, the carbon of the C—H bond can be a primary carbon, wherein R" is selected from the group consisting of $C_{1-6}$ alkyl, $C_{2-6}$ alkenyl, $C_{2-6}$ alkynyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —NR$^{11a}$R$^{11b}$, —C(O)R$^{11a}$, —C(O)OR$^{11a}$, —C(O)NR$^{11a}$R$^{11b}$, —SR$^{11a}$, —S(O)R$^{11a}$, —S(O)$_2$R$^{11a}$, $C_{3-8}$ cycloalkyl, $C_{3-8}$ heterocycloalkyl, $C_{6-10}$ aryl, and $C_{5-10}$ heteroaryl, optionally substituted with 1 to 5 R$^{11c}$ groups each independently selected from the group consisting of halogen, haloalkyl, haloalkoxy, —OR', =O, —OC(O)R', —(O)R', —O$_2$R', —ONR'R", —OC(O)NR'R", =NR', =N—OR', —NR'R", —NR"C(O)R', —NR'—(O)NR"R'", —NR"C(O)OR', —NH—(NH$_2$)=NH, —NR'C(NH$_2$)=NH, —NH—(NH$_2$)=NR', —SR', —S(O)R', —S(O)$_2$R', —S(O)$_2$NR'R", —NR'S(O)$_2$R", —N$_3$ and —NO$_2$. R', R" and R'" each independently refer to hydrogen, unsubstituted alkyl, such as unsubstituted $C_{1-6}$ alkyl, and $R^{12}$ and $R^{13}$ are both H. In some embodiments, the carbon of the C—H bond can be a secondary carbon, wherein $R^{11}$ and $R^{12}$ are each independently selected from the group consisting of $C_{1-6}$ alkyl, $C_{2-6}$ alkenyl, $C_{2-6}$ alkynyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —NR$^{11a}$R$^{11b}$, —C(O)R$^{11a}$, —C(O)OR$^{11a}$, —C(O)NR$^{11a}$R$^{11b}$, —SR$^{11a}$, —S(O)R$^{11a}$, —S(O)$_2$R$^{11a}$, $C_{3-8}$ cycloalkyl, $C_{3-8}$ heterocycloalkyl, $C_{6-10}$ aryl, and $C_{5-10}$ heteroaryl, optionally substituted with 1 to 5 R$^{11c}$ groups each independently selected from the group consisting of halogen, haloalkyl, haloalkoxy, —OR', =O, —OC(O)R', —(O)R', —O$_2$R', —ONR'R", —OC(O)NR'R", =NR', =N—OR', —NR'R", —NR"C(O)R', —NR'—(O)NR"R'", —NR"C(O)OR', —NH—(NH$_2$)=NH, —NR'C(NH$_2$)=NH, —NH—(NH$_2$)=NR', —SR', —S(O)R', —S(O)$_2$R', —S(O)$_2$NR'R", —NR'S(O)$_2$R", —N$_3$ and —NO$_2$. R', R" and R'" each independently refer to hydrogen, unsubstituted alkyl, such as unsubstituted $C_{1-6}$ alkyl, and $R^{13}$ is H. In some embodiments, the carbon of the C—H bond can be a tertiary carbon, wherein $R^{11}$, $R^{12}$ and $R^{13}$ are each independently selected from the group consisting of $C_{1-6}$ alkyl, $C_{2-6}$ alkenyl, $C_{2-6}$ alkynyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —NR$^{11a}$R$^{11b}$, —C(O)R$^{11a}$, —C(O)OR$^{11a}$, —C(O)NR$^{11a}$R$^{11b}$, —SR$^{11a}$, —S(O)R$^{11a}$, —S(O)$_2$R$^{11a}$, $C_{3-8}$ cycloalkyl, $C_{3-8}$ heterocycloalkyl, $C_{6-10}$ aryl, and $C_{5-10}$ heteroaryl, optionally substituted with 1 to 5 R$^{11c}$ groups each independently selected from the group consisting of halogen, haloalkyl, haloalkoxy, —OR', =O, —OC(O)R', —(O)R', —O$_2$R', —ONR'R", —OC(O)NR'R", =NR', =N—OR', —NR'R", —NR"C(O)R', —NR'—(O)NR"R'", —NR"C(O)OR', —NH—(NH$_2$)=NH, —NR'C(NH$_2$)=NH, —NH—(NH$_2$)=NR', —SR', —S(O)R', —S(O)$_2$R', —S(O)$_2$NR'R", —NR'S(O)$_2$R", —N$_3$ and —NO$_2$. R', R" and R'" each independently refer to hydrogen, unsubstituted alkyl, such as unsubstituted $C_{1-6}$ alkyl.

The product of the bond formation between the carbene precursor and the substrate can be represented by the following formula:

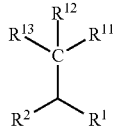

wherein $R^1$, $R^2$, $R^{11}$, $R^{12}$ and $R^{13}$ are each as defined above, and wherein $R^2$ can combine with one or more of $R^{11}$, $R^{12}$ and $R^{13}$ such that the bond formation is an intramolecular bond formation.

The product of the bond formation between the carbene precursor and the substrate can also have a preferred stereochemistry as represented by the following formula:

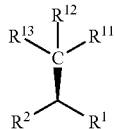

or the following formula:

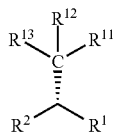

wherein $R^1$, $R^2$, $R^{11}$, $R^{12}$ and $R^{13}$ are each as defined above.

The product of the bond formation between the carbene precursor and the substrate can be represented by the following formula:

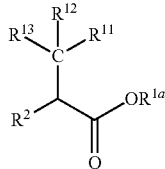

wherein $R^{1a}$, $R^2$, $R^{11}$, $R^{12}$ and $R^{13}$ are each as defined above, and wherein $R^2$ can combine with one or more of $R^{11}$, $R^{12}$ and $R^{13}$ such that the bond formation is an intramolecular bond formation.

When $R^2$ combines with one or more of $R^{11}$, $R^{12}$ and $R^{13}$, the substrate and the reactant are the same compound such that the substrate comprises a C—H group, and such that the bond formed between the reactant and the substrate results in formation of a $C_{5-6}$ cycloalkyl or $C_{5-6}$ heterocycloalkyl.

The product of the bond formation between the carbene precursor and the substrate can also have a preferred stereochemistry as represented by the following formula:

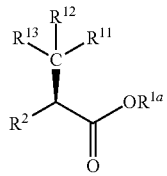

or the following formula:

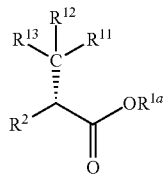

wherein $R^{1a}$, $R^2$, $R^{11}$, $R^{12}$ and $R^{13}$ are each as defined above.

The product of the bond formation between the nitrene precursor and the substrate can be represented by the following formula:

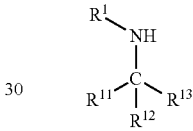

wherein $R^1$, $R^{11}$, $R^{12}$ and $R^{13}$ are each as defined above, and wherein $R^1$ can combine with one or more of $R^{11}$, $R^{12}$ and $R^{13}$ such that the bond formation is an intramolecular bond formation.

The product of the bond formation between the nitrene precursor and the substrate can be represented by the following formula:

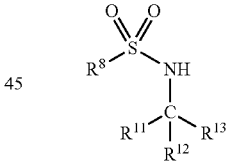

wherein $R^8$, $R^{11}$, $R^{12}$ and $R^{13}$ are each as defined above, and wherein $R^8$ can combine with one or more of $R^{11}$, $R^{12}$ and $R^{13}$ such that the bond formation is an intramolecular bond formation.

In some embodiments, the substrate and the reactant are the same compound such that the substrate comprises a C—H group and a sulfonyl azide, such that the bond formed between the reactant and the substrate results in formation of an amine bond.

The catalyst compositions of the present invention can be used to prepare new bonds with a variety of stereochemistries, as represented by the % enantiomeric excess (% ee), the excess percent of one enantiomer formed in a reaction over the other enantiomer. The enantiomeric excess represents the selectivity of a reaction to form one of a pair of enantiomers (R v. S). For example, the catalyst composition can provide a product with an enantiomeric excess of at least about 10% ee, or about 15, 20, 25, 30, 35, 40, 45, 50, 55, 60, 65, 70, 75, 80, 85, 90, or about 95% ee. The catalyst composition can provide a product with an enantiomeric excess of at least about −10% ee, or about −15, −20, −25, −30, −35, −40, −45, −50, −55, −60, −65, −70, −75, −80, −85, −90, or about −95% ee. Any of these values can represent the % ee for the R or the S enantiomer.

The catalyst compositions of the present invention can also have suitable turnover numbers (TON), which refers to the number of moles of substrate that a mole of catalyst can convert before becoming inactivatved. Representative turnover numbers can be at least about 100, 200, 300, 400, 500, 1000, 2000, 3000, 4000, 5000, 10000, or more.

B. Cyclopropanation

When the substrate includes an olefin, the resulting product is a substituted cyclopropyl group. Substrates including an olefin can have the following formula:

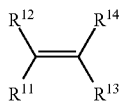

wherein $R^{11}$, $R^{12}$, $R^{13}$ and $R^{14}$ are each independently selected from the group consisting of H, $C_{1-6}$ alkyl, $C_{2-6}$ alkenyl, $C_{2-6}$ alkynyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —NR$^{11a}$R$^{11b}$, —C(O)R$^{11a}$, —C(O)OR$^{11a}$, —C(O)NR$^{11a}$R$^{11b}$, —SR$^{11a}$, —S(O)R$^{11a}$, —S(O)$_2$R$^{11a}$, $C_{3-8}$ cycloalkyl, $C_{3-8}$ heterocycloalkyl, $C_{6-10}$ aryl, and $C_{5-10}$ heteroaryl, optionally substituted with 1 to 5 $R^{11c}$ groups each independently selected from the group consisting of halogen, haloalkyl, haloalkoxy, —OR', =O, —OC(O)R', —(O)R', —O$_2$R', —ONR'R'', —OC(O)NR'R'', =NR', =N—OR', —NR'R'', —NR''C(O)R', —NR'—(O)NR''R''', —NR''C(O)OR', —NH—(NH$_2$)=NH, —NR'C(NH$_2$)=NH, —NH—(NH$_2$)=NR', —SR', —S(O)R', —S(O)$_2$R', —S(O)$_2$NR'R'', —NR'S(O)$_2$R'', —N$_3$ and —NO$_2$. R', R'' and R''' each independently refer to hydrogen, unsubstituted alkyl, such as unsubstituted $C_{1-6}$ alkyl. Alternatively, R' and R'', or R'' and R''', when attached to the same nitrogen, are combined with the nitrogen to which they are attached to form a heterocycloalkyl or heteroaryl ring, as defined above.

When the substrate includes an olefin, the olefin can be an alkene, cycloalkene, arylalkene such as styrene and styrene derivatives (alpha-methyl styrene, beta-methyl styrene (cis and trans)), vinyl ethers, as well as chiral alkenes. In some embodiments, the olefin can be an alkene, cycloalkene or an arylalkene. In some embodiments, the substrate comprises an olefin such that the bond formed between the reactant and the substrate results in formation of a cyclopropane.

The product of the bond formation between the carbene precursor and the substrate can then be represented by the following formula:

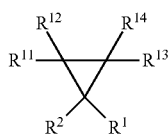

wherein $R^1$, $R^2$, $R^{11}$, $R^{12}$, $R^{13}$ and $R^{14}$ are each as defined above, and wherein $R^2$ can combine with one or more of $R^{11}$, $R^{12}$, $R^{13}$ and $R^{14}$ such that the bond formation is an intramolecular bond formation.

The product of the bond formation between the carbene precursor and the substrate can then be represented by the following formula:

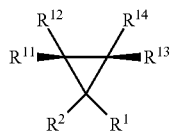

or the following formula:

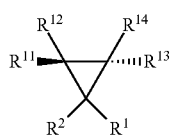

wherein $R^1$, $R^2$, $R^{11}$, $R^{12}$, $R^{13}$ and $R^{14}$ are each as defined above.

The product of the bond formation between the carbene precursor and the substrate can then be represented by the following formula:

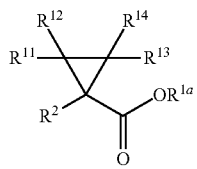

wherein $R^{1a}$, $R^2$, $R^{11}$, $R^{12}$, $R^{13}$ and $R^{14}$ are each as defined above, and wherein $R^2$ can combine with one or more of $R^{11}$, $R^{12}$, $R^{13}$ and $R^{14}$ such that the bond formation is an intramolecular bond formation.

The product of the bond formation between the carbene precursor and the substrate can then be represented by the following formula:

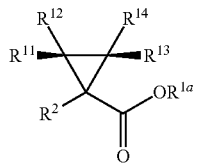

or the following formula:

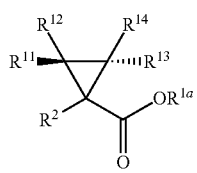

wherein $R^{1a}$, $R^2$, $R^{11}$, $R^{12}$, $R^{13}$ and $R^{14}$ are each as defined above.

One of skill in the art will appreciate that stereochemical configuration of the products will be determined in part by the orientation of the diazo reagent with respect to the position of an olefinic substrate such as styrene during the cyclopropanation step. For example, any substituent originating from the substrate can be positioned on the same side of the cyclopropyl ring as a substituent originating from the diazo reagent. Cyclopropanation products having this arrangement are called "cis" compounds or "Z" compounds. Any substituent originating from the olefinic substrate and any substituent originating from the diazo reagent can also be on opposite sides of the cyclopropyl ring. Cyclopropanation products having this arrangement are called "trans" compounds or "E" compounds.

Cyclopropanation product mixtures can have cis:trans ratios ranging from about 1:99 to about 99:1. The cis:trans ratio can be, for example, from about 1:99 to about 1:75, or from about 1:75 to about 1:50, or from about 1:50 to about 1:25, or from about 99:1 to about 75:1, or from about 75:1 to about 50:1, or from about 50:1 to about 25:1. The cis:trans ratio can be from about 1:80 to about 1:20, or from about 1:60 to about 1:40, or from about 80:1 to about 20:1 or from about 60:1 to about 40:1. The cis:trans ratio can be about 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, or about 1:95. The cis:trans ratio can be about 5:1, 10:1, 15:1, 20:1, 25:1, 30:1, 35:1, 40:1, 45:1, 50:1, 55:1, 60:1, 65:1, 70:1, 75:1, 80:1, 85:1, 90:1, or about 95:1.

For the cyclopropanation reaction, the % diastereomeric excess (% de) refers to the excess percent of one diastereomer formed in a reaction over an alternate diastereomer that can also form in the reaction. For example, the catalyst composition can provide a product with an diastereomeric excess of from about 1% to about 99% de, or from about −1% to about −99% de. Representative % de values include at least about 10% de, or about 15, 20, 25, 30, 35, 40, 45, 50, 55, 60, 65, 70, 75, 80, 85, 90, or about 95% de. Representative % ee values also include at least about −10% de, or about −15, −20, −25, −30, −35, −40, −45, −50, −55, −60, −65, −70, −75, −80, −85, −90, or about −95% de. The preference for one diastereomer over another can also be represented by the diastereomeric ratio (dr), which is a ratio of one diastereomer to another. Representative dr values for the reactions of the present invention can be 5:1, 10:1, 15:1 20:1, 25:1, 30:1, 35:1, 40:1, 50:1, 60:1, 70:1, 75:1, 80:1, 90:1, 100:1, 125:1, 150:175:1 and 200:1, or greater. The dr values can represent a cis/trans relationship of the primary substituents at each carbon relative to one another. The enantiomeric excess of individual stereocenters in the cyclopropanation reaction are also useful.

C. Reaction Conditions

The methods of the invention include forming reaction mixtures that contain the heme enzymes described herein. The heme enzymes can be, for example, purified prior to addition to a reaction mixture or secreted by a cell present in the reaction mixture. The reaction mixture can contain a cell lysate including the enzyme, as well as other proteins and other cellular materials. Alternatively, a heme enzyme can catalyze the reaction within a cell expressing the heme enzyme. Any suitable amount of heme enzyme can be used in the methods of the invention. In general, reaction mixtures contain from about 0.01 mol % to about 10 mol % heme enzyme with respect to the reactant and/or substrate. The reaction mixtures can contain, for example, from about 0.01 mol % to about 0.1 mol % heme enzyme, or from about 0.1 mol % to about 1 mol % heme enzyme, or from about 1 mol % to about 10 mol % heme enzyme. The reaction mixtures can contain from about 0.05 mol % to about 5 mol % heme enzyme, or from about 0.05 mol % to about 0.5 mol % heme enzyme. The reaction mixtures can contain about 0.1, 0.2, 0.3, 0.4, 0.5, 0.6, 0.7, 0.8, 0.9, or about 1 mol % heme enzyme.

The concentration of substrate and reactant are typically in the range of from about 100 μM to about 1 M. The concentration can be, for example, from about 100 μM to about 1 mM, or about from 1 mM to about 100 mM, or from about 100 mM to about 500 mM, or from about 500 mM to 1 M. The concentration can be from about 500 μM to about 500 mM, 500 μM to about 50 mM, or from about 1 mM to about 50 mM, or from about 15 mM to about 45 mM, or from about 15 mM to about 30 mM. The concentration of olefinic substrate or diazo reagent can be, for example, about 100, 200, 300, 400, 500, 600, 700, 800, or 900 μM. The concentration of olefinic substrate or diazo reagent can be about 1, 5, 10, 15, 20, 25, 30, 35, 40, 45, 50, 55, 60, 65, 70, 75, 80, 85, 90, 95, 100, 150, 200, 250, 300, 350, 400, 450, or 500 mM.

Reaction mixtures can contain additional reagents. As non-limiting examples, the reaction mixtures can contain buffers (e.g., 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, isopropanol, glycerol, tetrahydrofuran, acetone, acetonitrile, and acetic acid), salts (e.g., NaCl, KCl, CaCl.sub.2, and salts of Mn.sup.2+ and Mg.sup.2+), denaturants (e.g., urea and guandinium hydrochloride), detergents (e.g., sodium dodecylsulfate and Triton-X 100), chelators (e.g., ethylene glycol-bi s(2-aminoethylether)-N,N,N', N'-tetraacetic acid (EGTA), 2-({2-[Bis(carboxymethyl) amino)ethyl}) (carboxymethyl)amino)acetic acid (EDTA), and 1,2-bis(o-aminophenoxy)ethane-N,N,N,N-tetraacetic acid (BAPTA)), sugars (e.g., glucose, sucrose, and the like), and reducing agents (e.g., sodium dithionite, NADPH, dithiothreitol (DTT), .beta.-mercaptoethanol (BME), and tris(2-carboxyethyl)phosphine (TCEP)). Buffers, cosolvents, salts, denaturants, detergents, chelators, sugars, and reducing agents can be used at any suitable concentration, which can be readily determined by one of skill in the art. In general, buffers, cosolvents, salts, denaturants, detergents, chelators, sugars, and reducing agents, if present, are included in reaction mixtures at concentrations ranging from about 1 μM to about 1 M. For example, a buffer, a cosolvent, a salt, a denaturant, a detergent, a chelator, a sugar, or a reducing agent can be included in a reaction mixture at a concentration of about 1 or about 10 μM, or about 100 μM, or about 1 mM, or about 10 mM, or about 25 mM, or about 50 mM, or about 100 mM, or about 250 mM, or about 500 mM, or about 1 M. In some embodiments, a reducing agent is used in a sub-stoichiometric amount with respect to the olefin substrate and the diazo reagent. Cosolvents, in particular, can be included in the reaction mixtures in amounts ranging from about 1% v/v to about 75% v/v, or higher. A cosolvent can be included in the reaction mixture, for example, in an amount of about 5, 10, 20, 30, 40, or 50% (v/v).

Reactions are conducted under conditions sufficient to catalyze the formation of a cyclopropanation product. The reactions can be conducted at any suitable temperature. In general, the reactions are conducted at a temperature of from about 4.degree. C. to about 40.degree. C. The reactions can be conducted, for example, at about 25.degree. C. or about 37.degree. C. The reactions can be conducted at any suitable pH. In general, the reactions are conducted at a pH of from about 6 to about 10. The reactions can be conducted, for example, at a pH of from about 6.5 to about 9. The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. Reactions can be conducted under aerobic conditions or anaerobic conditions. Reactions can be conducted under an inert atmosphere, such as a nitrogen atmosphere or argon atmosphere. In some embodiments, a solvent is added to the reaction mixture. In some embodiments, the solvent forms a second phase, and the cyclopropanation occurs in the aqueous phase. In some embodiments, the heme enzyme is located in the aqueous layer, whereas the substrates and/or products occur in an organic layer. Other reaction conditions may be employed in the methods of the invention, depending on the identity of a particular heme enzyme, olefinic substrate, or diazo reagent.

Reactions can be conducted in vivo with intact cells expressing a heme enzyme of the invention. The in vivo reactions can be conducted with any of the host cells used for expression of the heme enzymes, as described herein. A suspension of cells can be formed in a suitable medium supplemented with nutrients (such as mineral micronutrients, glucose and other fuel sources, and the like). Cyclopropanation yields from reactions in vivo can be controlled, in part, by controlling the cell density in the reaction mixtures. Cellular suspensions exhibiting optical densities ranging from about 0.1 to about 50 at 600 nm can be used for cyclopropanation reactions. Other densities can be useful, depending on the cell type, specific heme enzymes, or other factors.

The methods of the invention can be assessed in terms of the diastereoselectivity and/or enantioselectivity of cyclopropanation reaction—that is, the extent to which the reaction produces a particular isomer, whether a diastereomer or enantiomer. A perfectly selective reaction produces a single isomer, such that the isomer constitutes 100% of the product. As another non-limiting example, a reaction producing a particular enantiomer constituting 90% of the total product can be said to be 90% enantioselective. A reaction producing a particular diastereomer constituting 30% of the total product, meanwhile, can be said to be 30% diastereoselective.

V. Examples

Unless stated otherwise, all reactions and manipulations were conducted on the laboratory bench in air with reagent grade solvents. Reactions under inert gas atmosphere were carried out in the oven dried glassware in a nitrogen-filled glovebox or by standard Schlenk techniques under nitrogen. NMR spectra were acquired on 400 MHz, 500 MHz, 600 MHz, or 900 MHz Bruker instruments at the University of California, Berkeley. NMR spectra were processed with MestReNova 9.0 (Mestrelab Research SL). Chemical shifts are reported in ppm and referenced to residual solvent peaks (Fulmer et al. (2010) *Organometallics* 29:2176). Coupling constants are reported in hertz. GC analyses were obtained on an Agilent 6890 GC equipped with either an HP-5 column (25 m×0.20 mm ID×0.33 m film) for achiral analysis or Cyclosil-B column (30m×0.25 mm×0.25 um film) for chiral analysis, and an FID detector. GC yields were calculated using dodecane as the internal standard and not corrected for response factors of minor isomers. High-resolution mass spectra and elemental analysis were obtained via the Micro-Mass/Analytical Facility operated by the College of Chemistry, University of California, Berkeley.

Unless noted otherwise, all reagents and solvents were purchased from commercial suppliers and used without further purification. If required, dichloromethane (DCM) and tetrahydrofuran (THF) were degassed by purging with argon for 15 minutes and dried with a solvent purification system containing a one-meter column of activated alumina; dried and degassed acetonitrile, 1,2-xylene, toluene, N,N-dimethylformamide (DMF), ethanol and methanol were purchased form commercial suppliers and used as received.

Example structures below are named according to standard IUPAC nomenclature using the CambridgeSoft ChemDraw naming package.

Example 1. Methyl Phenyldiazoacetate

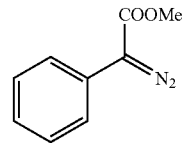

To a stirred solution of methyl phenylacetate (6.0 ml, 40 mmol) and 4-acetamidobenzenesulfonyl azide (p-ABSA, 14.4 g, 60 mmol) in acetonitrile (80 ml) at 0° C., 1,8-diazabicycloundec-7-ene (DBU, 9.6 ml, 64 mmol) was added dropwise. The cooling bath was removed, and the reaction was allowed to continue stirring overnight. The reaction mixture was diluted with dichloromethane (~60 ml), washed with water (2×~50 ml), dried over MgSO$_4$ and evaporated. The crude product was purified by column chromatography on silica gel, with a mixture of hexane and ethyl acetate (100:0 to 95:5 gradient) as the eluent. Fractions of the pure product were combined, and the solvent evaporated, yielding 5.5 g (78%) of product. The NMR data match those of the reported molecule (Nakamura et al. (2000) *J. Am. Chem. Soc.* 122:11340).

Example 2. Methyl (2-methoxyphenyl)diazoacetate

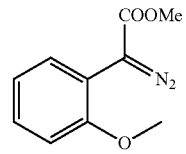

To a stirred solution of methyl (2-methoxyphenyl)acetate (3.2 ml, 20 mmol) and 4-acetamidobenzenesulfonyl azide (p-ABSA, 7.2 g, 30 mmol) in acetonitrile (40 ml) at 0° C., 1,8-diazabicycloundec-7-ene (DBU, 4.8 ml, 32 mmol) was added dropwise. The cooling bath was removed, and the reaction was allowed to continue stirring overnight. The reaction mixture was diluted with dichloromethane (~60 ml), washed with water (2×~50 ml), dried over MgSO$_4$. After filtration, the volatile material from the filtrate was evaporated under reduced pressure. The crude product was purified by column chromatography on silica gel, with a mixture of hexanes and ethyl acetate (100:0 to 95:5 gradient)

Example 3. Ethyl (2-methoxyphenyl)diazoacetate

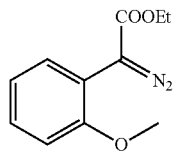

In a closed vial, a solution of (2-methoxyphenyl)acetic acid (3.3 g, 20 mmol) in ethanol (20 ml), containing several drops of sulfuric acid, was stirred overnight at 80° C. The volatile materials were evaporated under vacuum. The residue was dissolved in ethyl acetate (~40 ml), washed with NaHCO₃ sat. (40 ml) and water (40 ml), and dried over MgSO₄. After filtration, the volatile material from the filtrate was evaporated under reduced pressure. The resulting crude product was used in the next step without further purification.

To a stirred solution of ethyl (2-methoxyphenyl)acetate and 4-acetamidobenzenesulfonyl azide (p-ABSA, 7.2 g, 30 mmol) in acetonitrile (40 ml) at 0° C., 1,8-diazabicycloundec-7-ene (DBU, 4.8 ml, 32 mmol) was added dropwise. The cooling bath was removed, and the reaction was allowed to continue stirring overnight. The reaction mixture was diluted with dichloromethane (~60 ml), washed with water (2×~50 ml), and dried over MgSO₄. After filtration, the volatile material from the filtrate was evaporated under reduced pressure. The crude product was purified by column chromatography on silica gel, with a mixture of hexanes and ethyl acetate (100:0 to 95:5 gradient) as the eluent. Fractions of the pure product were combined, and the solvent evaporated, yielding 2.15 g (49%) of product. The NMR data match those of the reported molecule (Nicolle and Moody (2014) *Chemistry—A European Journal* 18:11063).

Example 4. Methyl (2-ethoxyphenyl)diazoacetate

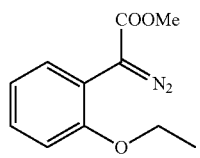

To a solution of (2-ethoxyphenyl)diazoacetate acid (3.8 g, 20 mmol) in toluene (40 ml) and methanol (20 ml), a solution of trimethysilyldiazomethane in diethyl ether (15 ml, 2 M, 30 mmol) was added dropwise while stirring, and stirring was continued for 2 hours. Upon evaporation of the volatile materials under vacuum, the product was obtained in quantitative yield without the need for further purification.

To a stirred solution of methyl (2-ethoxyphenyl)acetate (20 mmol) and 4-acetamidobenzenesulfonyl azide (p-ABSA, 7.2 g, 30 mmol) in acetonitrile (40 ml) at 0° C., 1,8-diazabicycloundec-7-ene (DBU, 4.8 ml, 32 mmol) was added dropwise. The cooling bath was removed, and the reaction was allowed to continue stirring overnight. The reaction mixture was diluted with dichloromethane (~60 ml), washed with water (2×~50 ml), dried over MgSO₄ and evaporated. The crude product was purified by column chromatography on silica gel, with a mixture of hexanes and ethyl acetate (100:0 to 95:5 gradient) as the eluent. Fractions of the pure product were combined, and the solvent evaporated, yielding 2.6 g (59%) of product. The NMR data match those of the reported molecule (Nicolle and Moody (2014) *Chemistry—A European Journal* 18:11063).

Example 5. Methyl (2,5-dimethoxyphenyl)diazoacetate

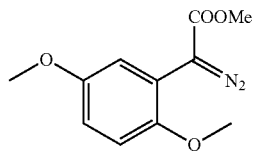

In a closed vial, a solution of (2,5-dimethoxyphenyl)acetic acid (3.8 g, 20 mmol) in methanol (20 ml) containing several drops of sulfuric acid, was stirred overnight at 80° C. The volatile materials were evaporated under vacuum. The residue was dissolved in ethyl acetate (~40 ml), washed with NaHCO₃ sat. (40 ml) and water (40 ml), dried over MgSO₄ and evaporated. The crude product was used in the next step without further purification.

To a stirred solution of methyl (2,5-dimethoxyphenyl)acetate and 4-acetamidobenzenesulfonyl azide (p-ABSA, 7.2 g, 30 mmol) in acetonitrile (40 ml) at 0° C., 1,8-diazabicycloundec-7-ene (DBU, 4.8 ml, 32 mmol) was added dropwise. The cooling bath was removed, and the reaction was allowed to continue stirring for 48 h (the reaction progress was followed by thin layer chromatography (TLC)). The reaction mixture was diluted with dichloromethane (~60 ml), washed with water (2×~50 ml), and dried over MgSO₄. After filtration, the volatile material from the filtrate was evaporated under reduced pressure. The crude product was purified by column chromatography on silica gel, with a mixture of hexanes and ethyl acetate (100:0 to 95:5 gradient) as the eluent. Fractions of the pure product were combined, and the solvent evaporated, yielding 4.1 g (87%) of product.

¹H NMR (900 MHz, CDCl₃): δ=7.14 (d, J=3.0 Hz, 1H), 6.78 (d, J=8.9 Hz, 1H), 6.75 (dd, J=8.9 Hz, J=3.0 Hz, 1H), 3.80 (s, 3H), 3.76 (s, 3H), 3.74 (s, 3H); ¹³C NMR (225 MHz, CDCl₃): d=166.7, 154.1, 149.8, 115.2, 114.7, 114.0, 112.3, 56.4, 56.0, 52.2 (C=N₂ signal missing, as observed before for related molecules (Huw et al. (2001))); HR MS (EI): calcd. for C₁₁H₁₂N₂O₄[M]⁺: 236.0797, found: 236.0801.

Example 6. Ethyl (2,5-dimethoxyphenyl)diazoacetate

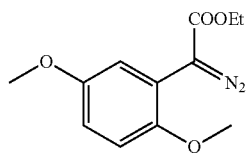

To a stirred solution of ethyl (2,5-dimethoxyphenyl)acetate (4.3 g, 19.2 mmol) and 4-acetamidobenzenesulfonyl azide (p-ABSA, 7.2 g, 30 mmol) in acetonitrile (40 ml) at 0° C., 1,8-diazabicycloundec-7-ene (DBU, 4.8 ml, 32 mmol) was added dropwise. The cooling bath was removed, and the reaction was allowed to continue stirring for 48 h (the reaction progress was followed by TLC). The reaction mixture was diluted with dichloromethane (~60 ml), washed with water (2×~50 ml), and dried over $MgSO_4$. After filtration, the volatile material from the filtrate was evaporated under reduced pressure. The crude product was purified by column chromatography on silica gel, with a mixture of hexanes and ethyl acetate (100:0 to 95:5 gradient) as the eluent. Fractions of the pure product were combined, and the solvent evaporated, yielding 3.9 g (81%) of product.

$^1$H NMR (900 MHz, $CDCl_3$): δ=7.16 (d, J=3.0 Hz, 1H), 6.78 (d, J=9.0 Hz, 1H), 6.74 (dd, J=9.0 Hz, J=3.0 Hz, 1H), 4.27 (q, J=7.2 Hz, 2H, $OCH_2$), 3.77 (s, 3H), 3.74 (s, 3H), 1.28 (t, J=7.2 Hz, 3H, $CH_2C\underline{H}_3$); $^{13}$C NMR (225 MHz, $CDCl_3$): d=166.3, 154.1, 149.8, 115.0, 114.9, 114.0, 112.3, 61.1, 56.4, 56.0, 14.8 (C=$N_2$ signal missing, as observed before for related molecules (Huw et al. (2001))); HR MS (EI): calcd. for $C_{12}H_{14}N_2O_4$ [M]$^+$: 250.0954, found: 250.0957.

Example 7. Benzyl (2,5-dimethoxyphenyl)diazoacetate

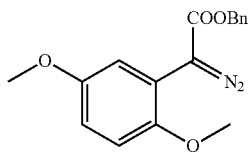

To a solution of (2,5-dimethoxyphenyl)acetic acid (0.95 g, 5 mmol) in dichloromethane (20 ml) thionyl chloride (2 ml) was added dropwise and the reaction mixture was stirred under reflux for 1 hour. The volatile materials were evaporated under vacuum. The residue was dissolved in dichloromethane (40 ml), benzyl alcohol (1 ml) was added, followed by slow addition of trimethylamine (1 ml), and the reaction mixture was stirred for 48 hours (the reaction progress was followed by TLC). The reaction mixture was washed with HCl (0.5 M, 40 ml) and water (40 ml), dried over $MgSO_4$ and evaporated. The crude product was purified by column chromatography on silica gel, with a mixture of hexanes and ethyl acetate (100:0 to 95:5 gradient) as the eluent. Fractions of the product were combined, and the solvent evaporated, yielding 1.43 g (quantitative) of benzyl (2,5-dimethoxyphenyl)acetate.

To a stirred solution of benzyl (2,5-dimethoxyphenyl) acetate (1.43 g, 5 mmol) and 4-acetamidobenzenesulfonyl azide (p-ABSA, 1.8 g, 7.5 mmol) in acetonitrile (20 ml) at 0° C., 1,8-diazabicycloundec-7-ene (DBU, 1.2 ml, 8 mmol) was added dropwise. The cooling bath was removed, and the reaction was allowed to continue stirring overnight. The reaction mixture was diluted with dichloromethane (~50 ml), washed with water (2×~50 ml), dried over $MgSO_4$ and evaporated. The crude product was purified by column chromatography on silica gel, with a mixture of hexanes and ethyl acetate (100:0 to 80:20 gradient) as the eluent. Fractions of the pure product were combined, and the solvent evaporated, yielding 0.94 g (60%) of product.

$^1$H NMR (900 MHz, $CDCl_3$): δ=7.37-7.32 (m, 4H), 7.31-7.28 (m, 1H), 7.16 (bs, 1H), 6.78 (d, J=9.0 Hz, 1H), 6.75 (dd, J=9.0 Hz, J=3.0 Hz, 1H), 5.26 (s, 2H), 3.76 (s, 3H), 3.71 (s, 3H); $^{13}$C NMR (225 MHz, $CDCl_3$): d=166.1, 154.1, 149.8, 136.3, 128.8, 128.4, 115.0, 114.6, 114.2, 112.3, 66.6, 56.4, 56.0 (C=$N_2$ signal missing, as observed before for related molecules (Huw et al. (2001))); HR MS (EI): calcd. for $C_{17}H_{16}N_2O_4$ [M]$^+$: 312.1110, found: 312.1111.

Example 8. Methyl (2,3-dimethoxyphenyl)diazoacetate

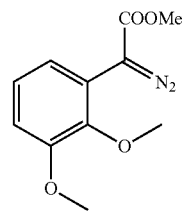

In a closed vial, a solution of (2,3-dimethoxyphenyl) acetic acid (1.5 g, 7.9 mmol) in methanol (20 ml) containing several drops of sulfuric acid, was stirred overnight at 80° C. The volatile materials were evaporated under vacuum. The residue was dissolved in ethyl acetate (~40 ml), washed with $NaHCO_3$ sat. (40 ml) and water (40 ml), dried over $MgSO_4$ and evaporated. The crude product was used in the next step without further purification.

To a stirred solution of methyl (2,3-dimethoxyphenyl) acetate and 4-acetamidobenzenesulfonyl azide (p-ABSA, 2.9 g, 12 mmol) in acetonitrile (30 ml) at 0° C., 1,8-diazabicycloundec-7-ene (DBU, 1.9 ml, 13 mmol) was added dropwise. The cooling bath was removed, and the reaction was allowed to continue stirring for 48 h (the reaction progress was followed by TLC). The reaction mixture was diluted with dichloromethane (~50 ml), washed with water (2×~50 ml), and dried over $MgSO_4$. After filtration, the volatile material from the filtrate was evaporated under reduced pressure. The crude product was purified by column chromatography on silica gel, with a mixture of hexanes and ethyl acetate (100:0→80:20 gradient) as the eluent. Fractions of the pure product were combined, and the solvent evaporated, yielding 1.55 g (83%) of product.

$^1$H NMR (900 MHz, $CDCl_3$): δ=7.19 (d, J=7.9 Hz, 1H), 7.05 (dd, J=8.1 Hz, J=8.1 Hz, 1H), 6.79 (d, J=8.2 Hz, 1H), 3.83 (s, 3H), 3.81 (s, 3H), 3.79 (s, 3H); 13C NMR (225 MHz, $CDCl_3$): d=166.6, 152.9, 145.3, 124.5, 121.3, 120.0, 111.4, 60.8, 56.0, 52.2 (C=$N_2$ signal missing, as observed before for related molecules (Huw et al. (2001))); HR MS (EI): calcd. for $C_{11}H_{12}N_2O_4$ [M]$^+$: 236.0797, found: 236.0800.

Example 9. General Procedure for Synthesis of Dihydrobenzofurans

To a solution of a derivative of methyl (2-methoxyphenyl) diazoacetate (~50 mM) in toluene a solution of Ir(Me)-PIX (8 mM, 0.2-2 mol %) in DMF was added, and the reaction mixture was vigorously stirred. The reaction progress was monitored by TLC. Upon completion, the volatile materials were removed, and the residue was purified by column chromatography on silica gel, with a mixture of hexanes and ethyl acetate (100:0 to 80:20 gradient) as eluent. Fractions of the pure product were combined, and the solvent evaporated, yielding 20-90% of desired product.

Example 10. Trans-methyl 2-methyl-2,3-dihydrobenzofuran-3-carboxylate

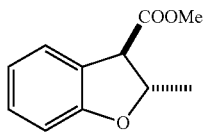

$^1$H NMR (900 MHz, CDCl$_3$): δ=7.29 (d, J=7.7 Hz, 1H), 7.15 (dd, J=7.8 Hz, J=7.6 Hz, 1H), 6.84 (dd, J=7.6 Hz, J=7.6 Hz, 1H), 6.76 (d, J=7.9 Hz, 1H), 5.13 (dq, J=7.9 Hz, J=6.5 Hz, 1H), 3.75 (s, 3H), 1.48 (d, J=6.5 Hz, 3H); $^{13}$C NMR (225 MHz, CDCl$_3$): d=171.7, 159.4, 129.7, 125.6, 124.4, 120.7, 110.1, 81.5, 54.5, 52.7, 21.4; HR MS (EI): calcd. for C$_{11}$H$_{12}$O$_3$ [M]$^+$: 192.0786, found: 192.0784.

Example 11. Ethyl 2,3-dihydrobenzofuran-3-carboxylate

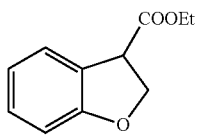 [SMILES: CCOC(=O)C1COc2ccccc21]

$^1$H NMR (900 MHz, CDCl$_3$): δ=7.34 (d, J=7.5 Hz, 1H), 7.14 (dd, J=7.9 Hz, J=7.9 Hz, 1H), 6.85 (dd, J=7.5 Hz, J=7.5 Hz, 1H), 6.78 (d, J=8.0 Hz, 1H), 4.90 (dd, J=9.0 Hz, J=6.8 Hz, 1H), 4.63 (dd, J=9.4 Hz, J=9.4 Hz, 1H), 4.29 (dd, J=9.7 Hz, J=6.8 Hz, 1H), 4.19 (dq, J=13.3 Hz, J=7.1 Hz, 2H), 1.27 (t, J=7.1 Hz, 3H); 13C NMR (225 MHz, CDCl$_3$): d=173.9, 162.6, 132.2, 128.1, 127.1, 123.4, 112.7, 75.2, 64.3, 49.9, 17.0; HR MS (EI): calcd. for C$_{11}$H$_{12}$O$_3$ [M]$^+$: 192.0786, found: 192.0782.

Example 12. Methyl 5-methoxy-2,3-dihydrobenzofuran-3-carboxylate

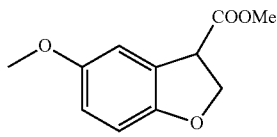

$^1$H NMR (900 MHz, CDCl$_3$): δ=6.91 (s, 1H), 6.71-6.68 (m, 2H), 4.86 (dd, J=9.1 Hz, J=6.7 Hz, 1H), 4.61 (dd, J=9.5 Hz, J=9.3 Hz, 1H), 4.27 (dd, J=9.5 Hz, J=6.7 Hz, 1H), 3.74 (s, 3H), 3.73 (s, 3H); $^{13}$C NMR (225 MHz, CDCl$_3$): d=171.7, 154.4, 154.1, 125.2, 114.9, 111.5, 110.1, 72.9, 56.3, 52.8, 47.8; HR MS (EI): calcd. for C$_{11}$H$_{12}$O$_4$ [M]$^+$: 208.0736, found: 208.0740.

Example 13. Ethyl 5-methoxy-2,3-dihydrobenzofuran-3-carboxylate

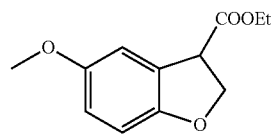 [SMILES: CCOC(=O)C1COc2ccc(OC)cc21]

$^1$H NMR (900 MHz, CDCl$_3$): δ=6.92 (s, 1H), 6.70-6.68 (m, 2H), 4.86 (dd, J=9.0 Hz, J=6.9 Hz, 1H), 4.61 (dd, J=9.6 Hz, J=9.1 Hz, 1H), 4.26 (dd, J=9.5 Hz, J=7.0 Hz, 1H), 4.19 (dq, J=19.2 Hz, J=7.1 Hz, 2H), 3.72 (s, 3H), 1.27 (t, J=7.1 Hz, 3H); $^{13}$C NMR (225 MHz, CDCl$_3$): d=171.2, 154.3, 154.2, 125.3, 114.9, 111.4, 110.1, 61.7, 56.3, 47.8, 14.5; HR MS (EI): calcd. for C$_{12}$H$_{14}$O$_4$ [M]$^\square$: 222.0892, found: 222.0893.

Example 14. Benzyl 5-methoxy-2,3-dihydrobenzofuran-3-carboxylate

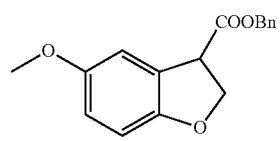

$^1$H NMR (900 MHz, CDCl$_3$): δ=7.35-7.29 (m, 5H), 6.86 (s, 1H), 6.70-6.68 (m, 2H), 5.17 (dd, J=43.3 Hz, J=12.2 Hz, 2H), 4.88 (dd, J=9.1 Hz, J=6.8 Hz, 1H), 4.62 (dd, J=9.5 Hz, J=9.2 Hz, 1H), 4.31 (dd, J=9.6 Hz, J=7.0 Hz, 1H), 3.66 (s, 3H); 13C NMR (225 MHz, CDCl$_3$): d=171.0, 154.3, 154.1, 135.7, 128.9, 128.7, 128.6, 125.0, 115.4, 111.1, 110.2, 72.9, 67.5, 56.2, 47.8; HR MS (EI): calcd. for C$_{17}$H$_{16}$O$_4$[M]$^+$: 284.1049, found: 284.1053.

Example 15. Methyl 7-methoxy-2,3-dihydrobenzofuran-3-carboxylate

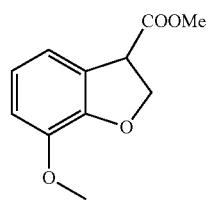

$^1$H NMR (900 MHz, CDCl$_3$): δ=6.95 (d, J=7.7 Hz, 1H), 6.81 (dd, J=7.9 Hz, J=7.7 Hz, 1H), 6.76 (d, J=8.2 Hz, 1H), 4.95 (dd, J=9.2 Hz, J=6.8 Hz, 1H), 4.69 (dd, J=9.7 Hz, J=9.3 Hz, 1H), 4.33 (dd, J=9.7 Hz, J=6.9 Hz, 1H), 3.83 (s, 3H), 3.73 (s, 3H); $^{13}$C NMR (225 MHz, CDCl$_3$): d=171.7, 148.6, 145.1, 125.2, 121.5, 117.6, 112.6, 73.4, 56.2, 52.8, 47.9; HR MS (EI): calcd. for C$_{11}$H$_{12}$O$_4$ [M]$^+$: 208.0738, found: 208.0740.

Example 16. General Procedure for Synthesis of Cyclopropanes

To a solution of an alkene (~0.1-0.5 M, 5-10 equiv.) in toluene, a solution of Ir(Me)-PIX (8 mM, 0.2 mol %) in DMF was added, followed by slow addition of a solution of ethyl diazoacetate (1 eq.) in toluene, while the reaction mixture was vigorously stirred. Upon completion, the volatile materials were removed and the residue was purified by column chromatography on silica gel, with a mixture of hexanes and ethyl acetate (100:0 to 95:5 gradient) as the eluent. Fractions of the pure product(s) were combined, and the solvent evaporated, yielding desired products.

Example 17. Methyl 2-phenyl-2-(phenylthio)acetate

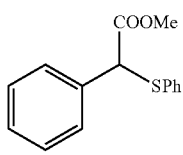

A solution of thiophenol (0.2 ml), methyl phenyldiazoacetate (0.1 ml) and Ir(Me)-PIX (1 mol %) in toluene (4 ml) was stirred vigorously overnight. The reaction progress was monitored by TLC. Upon completion, the volatile materials were removed and the residue was purified by column chromatography on silica gel, with a mixture of hexanes and ethyl acetate (100:0 to 90:10 gradient) as the eluent. Fractions of the pure product were combined, and the solvent evaporated, yielding the product from insertion of the carbene into the S—H bond. The NMR data of the product match those of the reported molecule (Kamata et al. (2010) *Chem. Lett.* 39:702).

Example 18. Ir(CO)Cl-Mesoporphyrin IX Dimethyl Ester

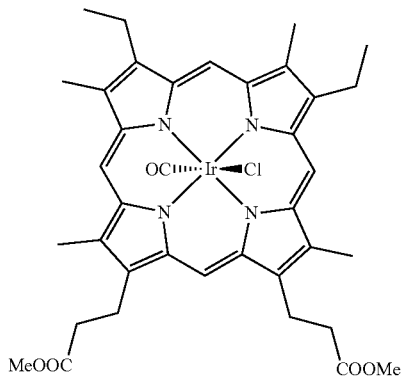

Under a nitrogen atmosphere, a suspension of mesoporphyrin IX dimethyl ester (250 mg, 0.42 mmol) and [Ir(COD)Cl]$_2$ (400 mg, 0.6 mmol) in dry and degassed 1,2-xylene (20 ml) was stirred at 150° C. for 7 days. The crude reaction mixture was loaded onto a plug of silica gel (SiO$_2$). The organic material was first eluted with a mixture of hexanes and ethyl acetate (100:0 to 75:25 gradient) to remove the remaining starting material and a side product. Then it was eluted with a mixture of hexanes and ethyl acetate (75:25 to 55:55 gradient) to collect the product. Fractions containing the pure product were combined, and the solvent evaporated, yielding 85 mg (24%) of a deep red solid.

$^1$H NMR (500 MHz, CDCl$_3$): δ=10.33-10.28 (m, 4H), 4.53-4.41 (m, 4H), 4.20-4.01 (m, 4H), 3.75-3.71 (m, 6H), 3.71-3.67 (m, 9H), 3.64 (s, 3HH), 3.38 (t, J=7.8 Hz, 4H), 1.95 (t, J=7.6 HZ, 6H); $^{13}$C NMR (225 MHz, CDCl$_3$): d=173.83, 173.82, 143.2, 143.1, 140.0, 139.8, 139.4, 139.23, 139.20, 139.19, 138.9, 138.5, 138.45, 138.4, 137.38, 137.35, 136.4, 136.3, 135.0, 99.2, 99.1, 99.0, 98.9, 51.99, 51.96, 37.05, 37.04, 22.07, 22.01, 20.10, 20.09, 17.85, 17.83, 12.02, 11.98, 11.85, 11.81; HR MS (ESI): calcd. for C$_{36}$H$_{40}$IrN$_4$O$_4$[M-Cl—CO]$^+$: 785.2673, found: 785.2715; IR (neat): 2031, 1735 cm$^{-1}$; UV/Vis (DMF, C=5·10$^{-6}$ M): λ$_{max}$ (log ε) 327 (4.23), 393 (5.29), 510 (4.02), 540 nm (4.27).

Example 19. Ir(Cl)-Mesoporphyrin IX

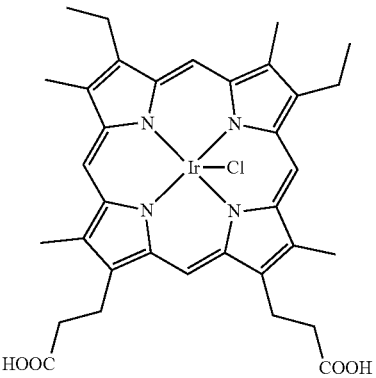

A solution of Ir(CO)Cl-mesoporphyrin IX dimethyl ester (25 mg, 0.03 mmol) and LiOH (100 mg) in THF (3 ml), methanol (1 ml) and water (1 ml) was stirred at room temperature for 2 hours. The reaction mixture was concentrated (~1 ml) under vacuum, diluted with sodium phosphate buffer (4 ml, 0.1 M, pH=5) and slowly acidified with HCl (0.5 M) to ~pH=5. The red precipitate was separated from the liquid by centrifugation (2000 rpm, 15 min, 4° C.) and subsequent decanting of the liquid. The red solid residue was suspended in water (15 ml), the mixture was centrifuged, and the liquid was decanted. The resulting solid was dried for overnight under high vacuum at room temperature, yielding 21 mg (88%) of dark red powder.

$^1$H NMR (600 MHz, D$_2$O+0.5% NaOD): d=10.22 (bs, 1H), 9.98 (bs, 3H), 4.35 (bs, 4H), 4.08 (bs, 4H), 3.67 (bs, 12H), 3.12 (bs, 4H), 1.84 (bs, 6H); $^{13}$C NMR (225 MHz, D$_2$O+0.5% NaOD): δ=185.7, 145.8, 145.6, 145.16, 145.10, 145.07, 145.0, 144.09, 144.08, 144.05, 143.9, 142.53, 142.51, 139.74, 139.71, 138.7, 138.5, 102.37, 102.14, 101.99, 101.96, 43.7, 25.4, 21.5, 19.95, 19.94, 13.12, 13.10, 12.88; HR MS (ESI): calcd. for C$_{34}$H$_{36}$IrN$_4$O$_4$[M-Cl]$^+$: 757.2360, found: 757.2393; IR (neat): 1706 cm$^{-1}$; UV/Vis (DMF, C=5·10$^{-6}$ M): λ$_{max}$ (log ε) 326 (4.40), 393 (5.26), 510 (4.15), 540 nm (4.37).

Example 20. Ir(Me)-Mesoporphyrin IX

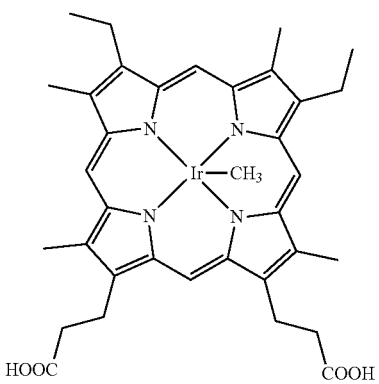

Under a nitrogen atmosphere, to a suspension of Ir(CO)Cl-mesoporphyrin IX dimethyl ester (110 mg, 0.13 mmol) in degassed ethanol (10 ml), a degassed solution of NaBH$_4$ (25 mg) and NaOH (1 M) in water (3 ml) was added. The reaction mixture was stirred at 50° C. for 1 hour in the dark, cooled to room temperature, and followed by addition of methyl iodide (10 ml). The reaction mixture was stirred overnight at room temperature. The reaction mixture was concentrated (~3 ml) under vacuum, followed by addition of LiOH (200 mg). The reaction mixture was stirred at room temperature for 1 hour, diluted with sodium phosphate buffer (8 ml, 0.1 M, pH=5) and slowly acidified with HCl (0.5 M) to ~pH=5. The red precipitate was separated from the liquid by centrifugation (2000 rpm, 15 min, 4° C.) and subsequent decanting of the liquid. The red solid residue was suspended in water (15 ml), the mixture was centrifuged, and the liquid was decanted. The resulting solid was dried for overnight under high vacuum at room temperature, yielding product quantitatively; dark red powder.

$^1$H NMR (900 MHz, DMF-d$_7$): d=12.56 (bs, 2H), 9.93 (s, 1H), 9.78 (s, 3H), 4.38-4.33 (m, 2H), 4.29-4.24 (m, 2H), 4.03-3.98 (m, 4H), 3.61 (s, 6H), 3.58 (s, 3H), 3.57 (s, 3H), 3.28 (q, J=7.5 Hz, 6H), 1.83 (t, J=7.5 Hz, 6H), −7.61 (s, 3H); $^{13}$C NMR (225 MHz, DMF-d$_7$): d=175.40, 175.39, 143.5, 143.2, 143.0, 142.91, 142.88, 142.79, 142.4, 142.0, 141.83, 141.82, 139.82, 139.76, 136.95, 136.90, 135.9, 135.7, 101.0, 100.9, 100.7, 100.5, 38.34, 38.32, 22.50, 22.49, 20.09, 20.06, 18.59, 18.55, 11.63, 11.61, 11.48, 11.44; HR MS (ESI): calcd. for $C_{35}H_{40}IrN_4O_4[M+H]^+$: 773.2673, found: 773.2708; IR (neat): 1706 cm$^{-1}$; UV/Vis (DMF, C=5·10$^{-6}$ M): $\lambda_{max}$ (log ε) 341 (4.39), 392 (5.07), 530 (4.24).

Example 21. 2-Propylbenzenesulfonyl azide

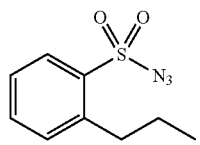

To a stirred solution of 1-bromo-2-propylbenzene (Ruano et al. (2005) *Tetrahedron* 61:10099, 5 g, 25 mmol) in 50 mL of dry THF was added n-butyllithium (12 mL, 2.5 M in hexanes, 30 mmol) dropwise at ~78° C., and the reaction mixture was stirred 1 h. Sulfuryl chloride (2.5 ml, 31 mmol) was added at ~78° C., the cooling bath was removed and the reaction mixture was stirred overnight at room temperature. Then the reaction was quenched with water (30 mL). The product was extracted with diethyl ether (3×50 mL), and the combined organic layers were washed with brine (30 mL), dried over MgSO$_4$ and evaporated. The crude product was purified by column chromatography on silica gel, with a mixture of hexanes and ethyl acetate (100:0 to 95:5 gradient) as the eluent. Fractions of the pure 2-propylbenzenesulfonyl chloride were combined, and the solvent evaporated, yielding 500 mg of product as colorless liquid, which was subjected to the next step without further purification.

To a solution of 2-propylbenzenesulfonyl chloride in an acetone:water mixture (40 ml, 1:1 v/v) was added sodium azide (500 mg, 7.7 mmol) at 0° C. The cooling bath was removed and the reaction mixture was let to stir for 24 hours. Then the reaction mixture was concentrated to ca. 20 ml. The product was extracted with diethyl ether (3×30 mL), and the combined organic layers were washed with brine (30 mL), dried over MgSO$_4$ and evaporated. The crude product was purified by column chromatography on silica gel, with a mixture of hexanes and ethyl acetate (100:0 to 95:5 gradient) as the eluent. Fractions of the pure product were combined, and the solvent evaporated, yielding 400 mg (7%, 2 steps) of product as colorless liquid.

$^1$H NMR (500 MHz, CDCl$_3$): δ=8.01 (d, J=8.0 Hz, 1H), 7.59 (t, J=7.5 Hz, 1H), 7.42 (d, J=7.7 Hz, 1H), 7.36 (t, J=7.7 Hz, 1H), 2.99-2.89 (m, 2H), 1.69 (dq, J=15.0, 7.4 Hz, 2H), 1.00 (t, J=7.3 Hz, 3H); $^{13}$C NMR (151 MHz, CDCl$_3$): d=143.38, 136.73, 134.74, 134.71, 132.20, 129.69, 126.56, 35.15, 24.65, 14.26; HR MS (EI): calcd. for $C_{11}H_{14}O_2[M]^+$: 178.0994, found: 178.0997.

Example 22. General Procedure for Synthesis of Sultams

In a closed vial, a solution of benzenesulfonyl azide (100 mg) and Ir(Me)-PIX (~4 mg) in toluene (6 ml) was stirred at 80° C. The reaction progress was monitored by TLC. Upon completion (~16 hours), the volatile materials were evaporated under reduced pressure, and the residue was purified by column chromatography on silica gel, with a mixture of hexanes and ethyl acetate (100:0 to 70:30 gradient) as eluent. Fractions of the pure product were combined, and the solvent evaporated, yielding sultam products.

Example 23. General Procedure for Synthesis of Benzenesulfonamide

To a solution of benzenesulfonyl azide (100 mg, ~0.5 mmol) in THF (5 ml) sodium borohydride (100 mg, 2.6 mmol) was added at room temperature. The reaction progress was monitored by TLC. Upon completion (~1 hour), the reaction was quenched with water (10 ml). The reaction mixture was concentrated to ca. 10 ml. The product was extracted with ethyl acetate (3×30 mL), and the combined organic layers were washed with brine (30 mL), dried over MgSO4 and evaporated. The crude product was purified by column chromatography on silica gel, with a mixture of hexanes and ethyl acetate (100:0 to 70:30 gradient) as the eluent. Fractions of the pure product were combined, and the solvent evaporated, yielding benzenesulfonamide products.

Example 24. 2,5-Diethylbenzenesulfonamide

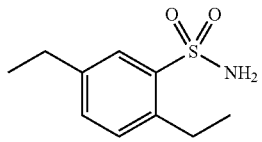

¹H NMR (600 MHz, CDCl₃): d=1H NMR (400 MHz, Chloroform-d) δ 7.82 (s, 1H), 7.36-7.25 (m, 2H), 3.00 (q, J=7.5 Hz, 2H), 2.64 (q, J=7.6 Hz, 2H), 1.28 (t, J=7.5 Hz, 3H), 1.21 (t, J=7.6 Hz, 3H); ¹H NMR (600 MHz, DMSO-d6): d=7.70 (s, 1H), 7.40-7.30 (m, 4H), 2.96 (q, J=7.5 Hz, 2H), 2.63 (q, J=7.6 Hz, 2H), 1.19 (q, J=7.2 Hz, 6H); 13C NMR (151 MHz, DMSO-d6): d=141.70, 141.30, 139.11, 131.25, 130.55, 126.26, 27.62, 24.89, 15.48, 15.40; HR MS (EI): calcd. for $C_9H_{13}NO_2S$ [M]⁺: 199.0667, found: 199.0668.

Example 25. 2-Propylbenzenesulfonamide

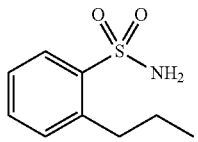

¹H NMR (600 MHz, CDCl₃): δ=7.96 (d, J=8.0 Hz, 1H), 7.46 (t, J=7.5 Hz, 1H), 7.34 (d, J=7.6 Hz, 1H), 7.26 (t, J=7.7 Hz, 1H), 4.94 (s, 2H), 2.98-2.92 (m, 2H), 1.70 (h, J=7.4 Hz, 2H), 0.99 (t, J=7.3 Hz, 3H); ¹³C NMR (151 MHz, CDCl₃): d=141.68, 139.87, 132.89, 131.46, 128.40, 126.23, 35.15, 24.48, 14.410; HR MS (EI): calcd. for $C_9H_{13}NO_2S$ [M]⁺: 199.0667, found: 199.0668.

Example 26. General Procedures for Synthesis of Cyclopropanes

Procedure A:

To a vial charged with the alkene (5-10 mmol, 5-10 equiv.) in toluene (10 ml), was added 100 µl of an 8 mM solution of Ir(Me)-PIX (0.0008 equiv.) in DMF. A solution of ethyl diazoacetate (EDA, 1 mmol, 1 equiv.) in toluene (1 ml) was then added slowly while the reaction mixture was vigorously stirred. After complete addition of EDA, the reaction was stirred for 30-60 minutes, after which time the evolution of nitrogen stopped, indicating full consumption of EDA. Then, the volatile materials were removed, and the residue was purified by column chromatography on silica gel, with a mixture of hexanes and ethyl acetate (100:0 to 85:15 gradient) as the eluent. Fractions of the pure product(s) were combined, and the solvent evaporated, yielding cyclopropanation products.

Procedure B:

To a solution of alkene (~0.2 M) and Rh₂AcO₄ (~0.1-1 mol % in respect to EDA) in dry DCM, a solution of ethyl diazoacetate (~1 M) in dry DCM was added slowly while the reaction mixture was vigorously stirred. After complete addition of EDA, the reaction was stirred for 30-60 min, after which time the evolution of nitrogen stopped, indicating full consumption of EDA. Then, the volatile materials were removed, and the residue was purified by column chromatography on silica gel, with a mixture of hexanes and ethyl acetate (100:0 to 85:15 gradient) as the eluent. Fractions of the pure product(s) were combined, and the solvent evaporated, yielding cyclopropanation products.

Example 27. Ethyl syn-2-methyl-syn-3-pentylcyclopropane-1-carboxylate

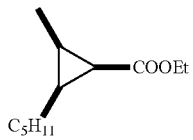

The product was isolated from a reaction of cis-2-octene (1 ml) with EDA (0.25 ml) conducted following Procedure B of Example 26. ¹H NMR (900 MHz, CDCl₃): δ=4.09-4.05 (m, 2H), 1.60-1.57 (m, 3H), 1.38-1.36 (dq, J=6.5 Hz, J=2.2 Hz, 1H), 1.31-1.22 (m, 11H), 1.18 (d, J=6.2 Hz, 3H), 0.85 (m, J=6.7 Hz, 3H); ¹³C NMR (151 MHz, CDCl₃): d=172.34, 59.76, 31.84, 29.57, 25.36, 22.82, 22.10, 20.76, 19.04, 14.55, 14.20, 7.53; HR MS (EI): calcd. for $C_{12}H_{21}O_2$ [M]⁺: 198.1620, found: 198.1622.

Example 28. Ethyl anti-2-methyl-anti-3-pentylcyclopropane-1-carboxylate

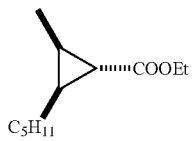

The product was isolated from a reaction of cis-2-octene (1 ml) with EDA (0.25 ml) conducted following Procedure B of Example 26. ¹H NMR (900 MHz, CDCl₃): δ=4.08 (q, J=7.2 Hz, 2H), 1.46 (m, 1H), 1.39-1.30 (m, 5H), 1.28-1.24 (m, 4H), 1.23 (t, J=7.2 Hz, 3H), 1.08 (d, J=6.3 Hz, 3H), 0.99 (t, J=4.8 Hz, 1H), 0.87 (t, J=7.4 Hz, 3H); 13C NMR (151 MHz, CDCl₃): d=174.85, 60.33, 31.77, 29.31, 28.15, 27.99, 27.23, 22.76, 21.92, 14.47, 14.19, 12.16; HR MS (EI): calcd. for $C_{12}H_{21}O_2$ [M]⁺: 198.1620, found: 198.1619.

Example 29. Syn-2-ethyl 1-ethyl 1-methylcyclopropane-1,2-dicarboxylate

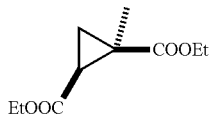

The product was isolated from a reaction of ethyl methacrylate (3 ml) with EDA (1 ml) conducted following Procedure B of Example 26. The isolated product contains 5% impurity by GC. Stereochemistry assigned based on comparison of NMR data to analogous compound (Chen et al. (2007) J. Am. Chem. Soc. 129:12074). ¹H NMR (500 MHz, CDCl₃): δ=4.10-4.20 (m, 4H), 1.78-1.84 (m, 2H), 1.41 (s, 3H), 1.24-1.28 (m, 6H), 1.04-1.10 (m, 1H); ¹³C NMR (151 MHz, CDCl₃): d=171.73, 170.55, 61.12, 60.93, 29.06, 28.97, 21.33, 19.64, 14.33, 14.24; HR MS (EI): calcd. for $C_{10}H_{16}O_4$[M]⁺: 200.1049, found: 200.1051.

Example 30. Anti-2-ethyl 1-ethyl 1-methylcyclopropane-1,2-dicarboxylate

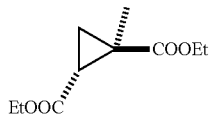

The product was isolated from a reaction of ethyl methacrylate (3 ml) with EDA (1 ml) conducted following Procedure B of Example 26. The isolated product contains 5% impurity by GC. Relative stereochemistry was assigned based on comparison with the NMR data for the methyl ester analogue: anti-2-ethyl 1-methyl 1-methylcyclopropane-1,2-dicarboxylate. $^1$H NMR (600 MHz, CDCl$_3$): δ=4.07-4.16 (m, 4H), 2.29 (dd, J=8.7, 6.5 Hz, 1H), 1.53 (dd, J=8.7, 4.2 Hz, 1H), 1.36 (s, 3H), 1.31-1.26 (m, 1H), 1.23 (dt, J=10.7, 7.1 Hz, 6H); $^{13}$C NMR (151 MHz, CDCl$_3$): d=173.64, 170.63, 61.37, 61.04, 27.98, 27.10, 21.12, 14.45, 14.28, 14.26, 13.21; HR MS (EI): calcd. for C$_{10}$H$_{16}$O$_4$[M]$^+$: 200.1049, found: 200.1051.

Example 31. Cis-ethyl 2-(3-oxobutyl)cyclopropane-1-carboxylate

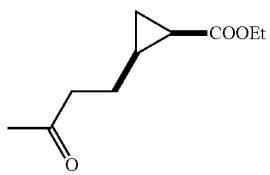

The product was isolated from a reaction of hex-5-en-2-one (2 ml) with EDA (1 ml) conducted following Procedure B of Example 26. $^1$H NMR (600 MHz, CDCl$_3$): δ=4.13-4.04 (m, 2H), 2.41 (td, J=7.3, 4.9 Hz, 2H), 2.08 (s, 2H), 1.83 (ddt, J=14.4, 7.2, 7.2 Hz, 1H), 1.72 (ddt, J=14.6, 7.4, 7.4 Hz, 1H), 1.63 (ddd, J=8.3, 5.5 Hz, 1H), 1.17-1.26 (m, 3+1H), 0.96 (ddd, J=8.2, 8.2, 4.5 Hz, 1H), 0.88 (ddd, J=6.9, 5.0, 5.0 Hz, 1H); 13C NMR (151 MHz, CDCl$_3$): d=208.44, 172.89, 60.46, 43.50, 29.92, 21.67, 21.65, 21.09, 21.08, 18.37, 14.46, 13.52, 13.51; HR MS (EI): calcd. for C$_{10}$H$_{16}$O$_3$[M]$^+$: 184.1099, found: 184.1199.

Example 32. 6-ethyl 3-methyl (1R,3s,5S,6s)-bicyclo[3.1.0]hexane-3,6-dicarboxylate

The product was isolated from a reaction of methyl cyclopent-3-ene-1-carboxylate (0.3 ml) with EDA (0.5 ml) conducted following Procedure B of Example 26. Relative stereochemistry was assigned based on comparison with the NMR data for the analogue: methyl syn-3-carbomethoxybicyclo[3.1.0]hexane-6-acetate (Carfagna et al. (1991) *J. Org. Chem.* 56:3924). $^1$H NMR (900 MHz, CDCl$_3$): δ=4.11 (q, J=7.1 Hz, 2H), 3.63 (s, 3H), 2.93 (p, J=8.7 Hz, 1H), 2.22 (m, 4H), 1.82 (m, 2H), 1.67 (t, J=8.3 Hz, 1H), 1.25 (t, J=7.4 Hz, 3H); $^{13}$C NMR (226 MHz, CDCl$_3$): d=176.50, 171.61, 61.24, 51.75, 43.08, 29.80, 25.71, 23.60, 14.26.; HR MS (EI): calcd. for C$_{11}$H$_{16}$O$_4$[M]$^+$: 212.1049, found: 212.1048.

Example 33. 6-ethyl 3-methyl (1R,3r,5S,6s)-bicyclo[3.1.0]hexane-3,6-dicarboxylate

The product was isolated from a reaction of methyl cyclopent-3-ene-1-carboxylate (0.3 ml) with EDA (0.5 ml) conducted following Procedure B of Example 26. $^1$H NMR (900 MHz, CDCl$_3$): δ=4.09 (q, J=7.1 Hz, 2H), 3.65 (s, 3H), 3.34 (p, J=9.5 Hz, 1H), 2.26 (m, 4H), 1.88 (m, 3H), 1.66 (t, J=8.5 Hz, 1H), 1.22 (t, J=7.2 Hz, 3H); 13C NMR (226 MHz, CDCl$_3$): d=175.18, 171.25, 59.90, 51.87, 49.45, 27.67, 26.29, 14.33; HR MS (EI): calcd. for C$_{11}$H$_{16}$O$_4$ [M]$^+$: 212.1049, found: 212.1050.

Example 34. Protein Expression Methods

Figure 2:
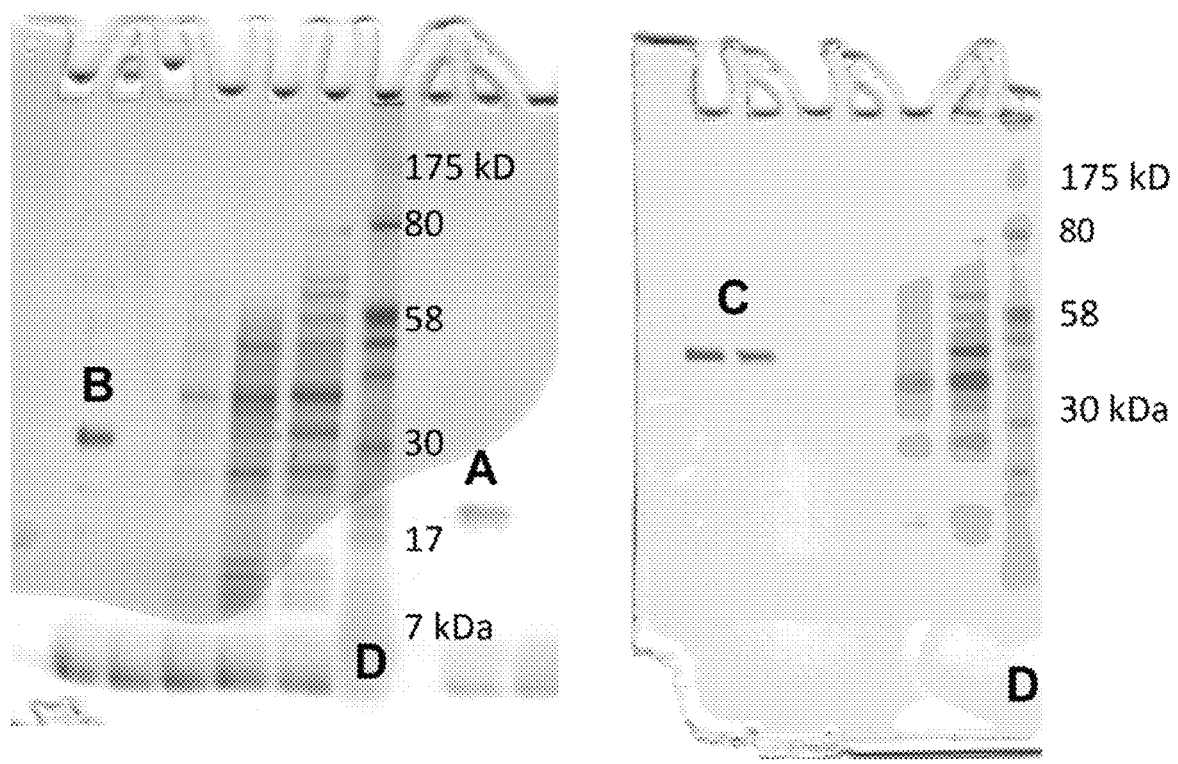
FIG. 2 presents results of characterization of purified apo myoglobin (indicated as "A") mOCR-myoglobin (indicated as "B"), and P411-CIS (indicated as "C") proteins by SDS-PAGE gel electrophoresis. Protein samples are shown in comparison to a standard protein ladder (indicated as "D").
Figure 3:
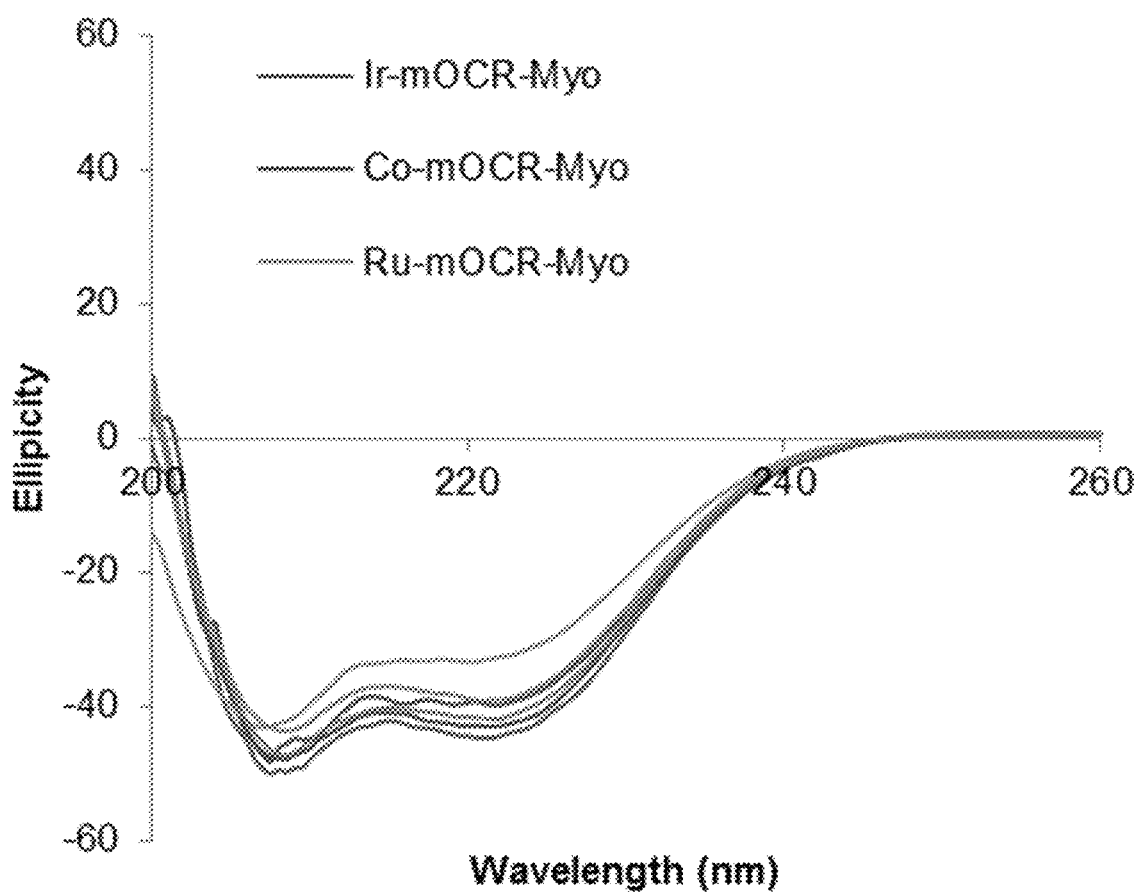
FIG. 3 presents the CD and UV spectra of native and artificially metallated proteins.

An evaluation of protein expression methods (Table 1) identified conditions to express and purify apo-PIX proteins directly (FIG. 1A). Mutants of Physeter macrocephalus myoglobin (Myo) (Carey et al. (2004) *J. Am. Chem. Soc.* 126:10812) and *Bacillus megaterium* cytochrome P450 BM3h (P450) (Coelho et al. (2013) *Nat. Chem. Biol.* 9:485) were overexpressed and purified (40 and 10 mg/L culture, respectively, FIG. 2, Table 2) with less than 5% incorporation of the native Fe-PIX cofactor, as determined by ICP-OES. To generate a more stable apo protein, a variant of myoglobin fused to an mOCR stability tag was also expressed (70 mg/L culture, FIG. 2). The CD spectra of the apo-proteins and their native Fe-counterparts indicated that the apo proteins retain the native fold (FIG. 1B, FIG. 3, FIG. 4, FIG. 5, and FIG. 6).

TABLE 1

| Expression Condition | Induction Method | OD at Induction | Induction Time | Induction Temp | Media pH | Isolated Protein Yield (Per liter expression) |
| --- | --- | --- | --- | --- | --- | --- |
| A | IPTG | 0.61 | 16 h | 30° C. | 7.2 | 5 mg |
| B | Auto | — | 24 h | 30° C. | 7.2 | 5 mg |
| C | IPTG | 0.82 | 16 h | 30° C. | 7.2 | 3 mg |
| D | IPTG | 0.98 | 16 h | 30° C. | 7.2 | 3 mg |
| E | IPTG | 0.98 | 16 h | 30° C. | 8.2 | 20 mg |

TABLE 1-continued

| Expression Condition | Induction Method | OD at Induction | Induction Time | Induction Temp | Media pH | Isolated Protein Yield (Per liter expression) |
|---|---|---|---|---|---|---|
| F | IPTG | 1.4 | 16 h | 15° C. | 8.2 | 16 mg |
| G | IPTG | 1.4 | 16 h | 20° C. | 8.2 | 40 mg |
| H | IPTG | 1.4 | 16 h | 25° C. | 8.2 | 15 mg |
| I | IPTG | 1.4 | 16 h | 30° C. | 8.2 | 18 mg |

TABLE 2

| Protein | Organism | Construction | Vector | Sequence |
|---|---|---|---|---|
| Myoglobin | Physeter macrocephalus | 6xHis-TEV-Myo | 2BT | EGDIHMKSSHHHHHHENLYFQSNAVLSEGE WQLVLHVWAKVEADVAGHGQDILIRLFKSH PETLEKFKHLKTEAEMKASEDLKKHGVTVL TALGAILKKKGHHEAELKPAQSHATKHKIP IKYLEFISEAIIHVLHSRHPGDFGADAQGA MNKALELFRKDIAAKYKELGYQG |
| mOCR-Myoglobin | Physeter macrocephalus | 6xHis-TEV-mOCR-Myo | 2BT | EGDIHMKSSHHHHHHENLYFQSNMSNMTYN NVFDHAYEMLKENIRYDDIRDTDDLHDAIH MAADNAVPHYYADIRSVMASEGIDLEFEDS GLMPDTKDDIRILQARIYEQLTIDLWEDAE DLLNEYLEEVEEYEEDEEGTGSETPGTSES GVLSEGEWQLVLHVWAKEADVAGHGQDILI RLFKSHPETLEKFDRFKHLKTEAEMKASED LKKHGVTVLTALGAILKKKGHHEAELKPLA QSHATKHKIPIKYLEFISEAIIHVLHSRHP GDFGADAQGAMNKALELFRKDIAAKYKELG YQG |
| P450BM3 | Bacillus megaterium | P450-BM3-6xHis | pcWori | MTIKEMPQPKTFGELKNLPLLNTDKPVQAL MKIADELGEIFKFEAPGRVTRYLSSQRLIK EACDESRFDKNLSQALKFARDFAGDGLVTS WTHEKNWKKAHNILLPSFSQQAMKGYHAMM VDIAVQLVQKWERLNADEHIEVSEDMTRLT LDTIGLCGFNYRFNSFYRDQPHPFIISMVR ALDEVMNKLQRANPDDPAYDENKRQEDIKV MNDLVDKIIADRKARGEQSDDLLTQMLNGK DPETGEPLDDGNIRYQIITFLIAGHEATSG LLSFALYFLVKNPHVLQKVAEEAARVLVDP VPSYKQVKQLKYVGMVLNEALRLWPTAPAF SLYAKEDTVLGGEYPLEKGDEVMVLIPQLH RDKTVWGDDVEEFRPERFENPSAIPQHAFK PFGNGQRASIGQQFALHEATLVLGMMLKHF DFEDHTNYELDIKETLTLKPKGFVVKAKSK KIPLGGIPSPSTHHHHHH |

Figure 7:
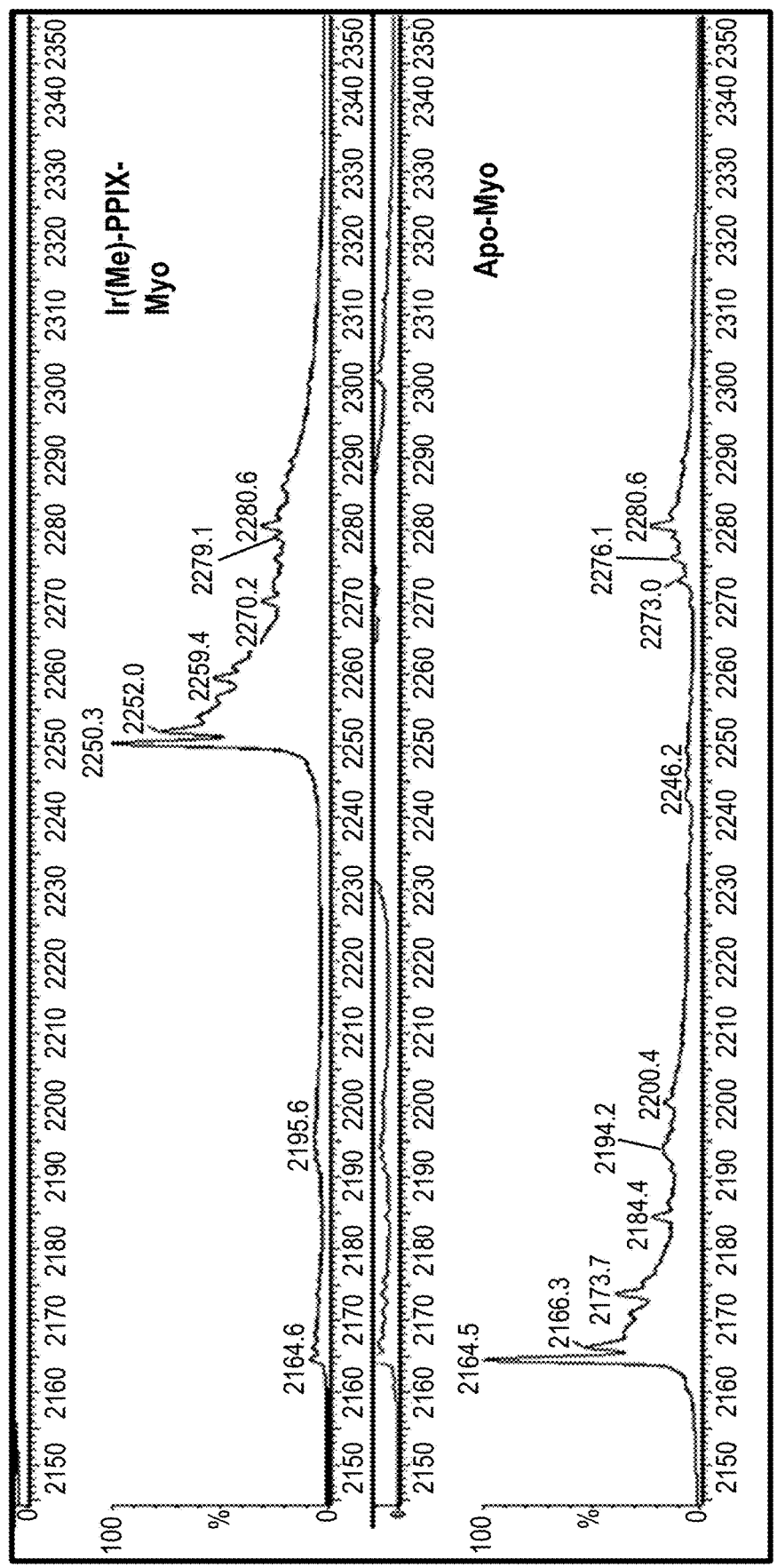
FIG. 7 presents native NS-ESI-MS data showing the binding of Ir(Me)-PIX to apo-Myo in a 1:1 stoichiometry.
Figure 8:
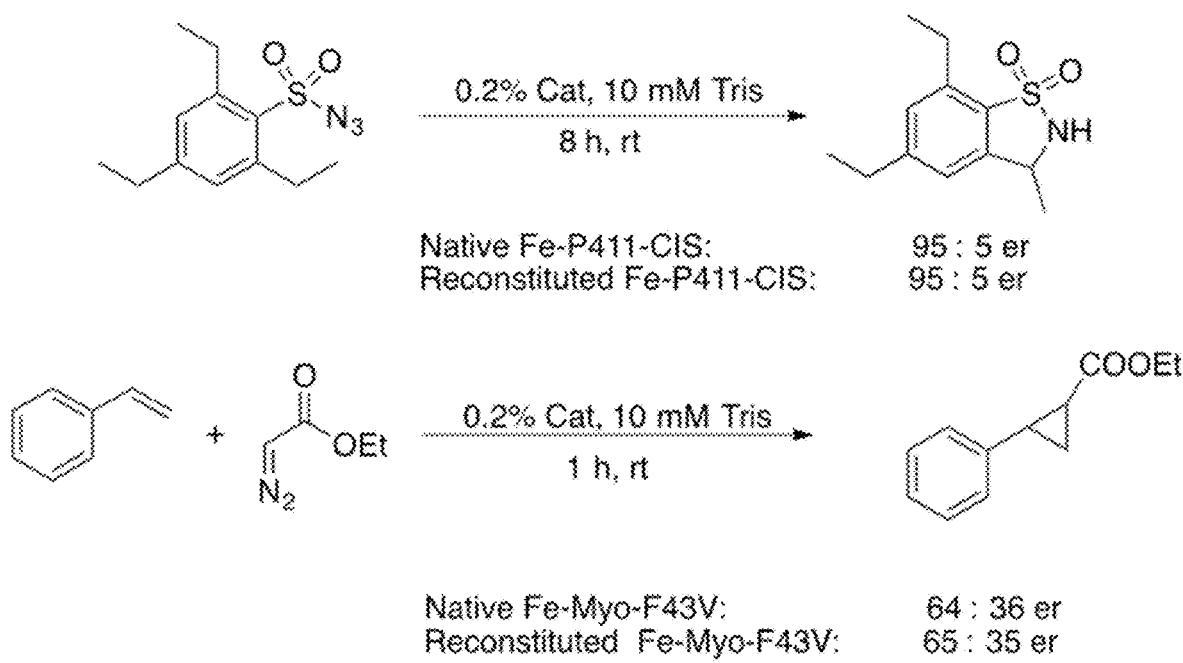
FIG. 8 presents schemes and selectivities of reactions catalyzed by native Fe and reconstituted Fe-PIX-proteins.
Figure 9:
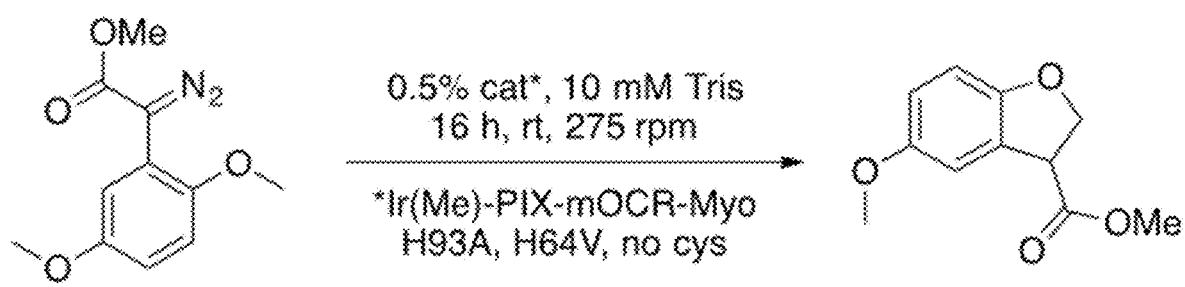
FIG. 9 presents schemes and selectivities of reactions of Ir(Me)-PIX-H93A/H64V upon storage under various conditions.

The obtained apo-proteins were reconstituted quantitatively within several minutes upon addition of stoichiometric amounts of various [M]-PIX cofactors, as determined by UV-Vis and CD spectroscopy, as well as size-exclusion chromatography (FIG. 1A, FIG. 3, FIG. 4, FIG. 5, and FIG. 6). Native nanoESI-MS of apo-Myo reconstituted with Fe(Cl)-PIX or the abiological Ir(Me)-PIX cofactor confirmed the 1:1 ratio of the cofactor to protein (FIG. 7). Moreover, cyclopropanation and C—H amidation reactions catalyzed by reconstituted Fe myoglobin and P450 occurred with the same enantioselectivities as those catalyzed by native Fe proteins (FIG. 8). The observation of reactivity and enantioselectivity matching those of the enzyme expressed under conventional conditions provides strong evidence that the [M]-PIX cofactors are bound within the apo-PIX protein at the native PIX-binding site, and that the catalyst constructs are stable throughout the reaction. These reconstituted mOCR-myoglobins are also stable upon storage; reactions catalyzed by freshly prepared, frozen, and lyophilized enzymes all proceed with comparable enantioselectivity (FIG. 9).

Example 35. Preparation of mOCR-Myo Catalysts with Diverse [M]-PIX Cofactors

Figure 10:
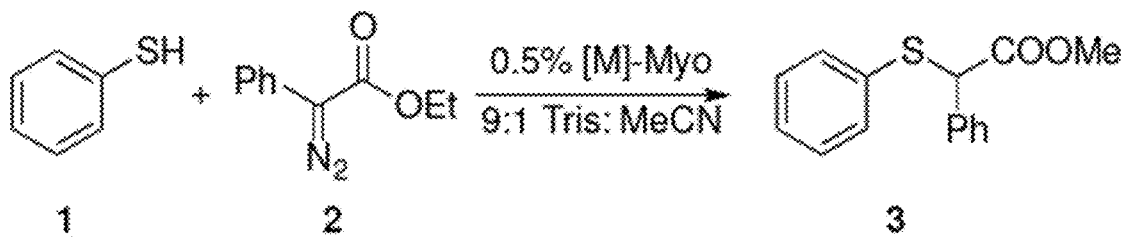
FIG. 10 presents results of S—H insertion of methyl phenyl diazoacetate (MPDA) into thiophenol catalyzed by an array of 64 artificial mOCR-myoglobins generated with eight, single-step affinity chromatography purifications of protein scaffolds. TON=turnover number.

Porphyrin catalyst variants were prepared that containing eight different amino acids in the axial position of the PIX-binding site, including neutral nitrogen donors (histidine; H, native ligand), anionic and neutral sulfur donors (cysteine; C and methionine; M), anionic and neutral oxygen donors (aspartic acid; D, glutamic acid; E, and serine; S), and small, non-coordinating moieties (alanine; A, glycine; G). An additional mutation to the residue directly above the catalytic metal (H64V) was incorporated to expand the binding site for artificial substrates. The [M]-PIX derivatives incorporated into these mutants contained Fe(Cl)-, Co(Cl)-, Cu-, Mn(Cl)-, Rh-, Ir(Cl)-, Ru(CO)- and Ag-sites. By this straightforward combinatorial pairing of solutions of cofactors and apo proteins, an array of 64 artificial mOCR-myoglobins was generated with only eight, single-step affinity chromatography purifications of protein scaffolds (FIG. 10).

To prepare the multidimensional catalyst array, BL21 Star competent E. coli cells (50 µL, QB3 Macrolab, UC Berkeley) were thawed on ice, transferred to 14 mL Falcon tubes, and transformed with the desired plasmid solution (2 µL, 50-250 ng/µL). The cells were incubated on ice (30 min), heat shocked (20 seconds, 42° C.), re-cooled on ice (2 minutes), and recovered with SOC media (37° C., 1 hour, 250 rpm). Aliquots of the cultures were diluted (0.02×), plated on minimal media plates (expression media supplemented with 17 g agar/L), and incubated (20 hours, 37° C.) to produce approximately 10-100 colonies per plate. Single colonies were used to inoculate starter cultures (3 mL, expression media), which were grown (6-8 hours, 37° C., 275 rpm) and used to inoculate 100 mL overnight cultures (minimal media, 37° C., 275 rpm). Each overnight culture was used to inoculate 750 mL of minimal media, which was further grown (9 hours, 37° C., 275 rpm). Expression was induced with IPTG (800 uL, 1M), and the cultures were further grown (15 hours, 20° C., 275 rpm). Cells were harvested by centrifugation (5000 rpm, 15 minutes, 4° C.), and the pellets were resuspended in 20 mL Ni-NTA lysis buffer (50 mM NaPi, 250 mM NaCl, 10 mM Imidazole, pH=8.0) and stored at −80° C. until purification.

Cell suspensions were thawed in a room temperature ice bath, decanted to 50 mL glass beakers, and lysed on ice by sonication (3×30 seconds on, 2×2 minutes off, 60% power). Crude lysates were transferred to 50 mL Falcon tubes, treated with triton X (100 µL, 2% in $H_2O$), and incubated on an end-over-end shaker (30 minutes, room temperature, 15 rpm). Cell debris was removed by centrifugation (10,000 rpm, 60 minutes, 4° C.), and Ni-NTA (5 mL, 50% suspension per 850 mL cell culture) was added. The lysates were briefly incubated with Ni-NTA (30 minutes, 4° C., 20 rpm) and poured into glass frits (coarse, 50 mL). The resin was washed with Ni-NTA lysis buffer (3×35 mL), and the wash fractions were monitored using Bradford assay dye. The desired protein was eluded with 18 mL Ni-NTA elusion buffer (50 mM *NaPi,* 250 mM NaCl, 250 mM Imidazole, pH=8.0), dialyzed against Tris buffer (10 mM, pH=8.0, 12 hours, 4° C.), concentrated to the desired concentration using a spin concentrator, and metallated within several hours. Apo protein was not stored for more than 8 hours.

Stock solutions of 9 metal cofactors (8.3 uL per well, 6 mM, DMF) were distributed in a nitrogen-atmosphere glove box down the columns of a 96-well plate containing 1.2 mL glass vials. Each mutant was concentrated to 0.6 mM and degassed on a Schlenk line (3 cycles vacuum/refill), and the mutants were distributed across the rows of the same 96-well plate (166 uL protein per vial) to generate 72 unique catalysts formed from different combinations of cofactors and mutants. The prepared portion of each catalyst was evenly divided among 4 separate 96-well reaction plates of the same type (42 uL per well), and each well was diluted to 250 uL with 10 mM tris buffer, pH=8.0.

Example 36. General Catalytic Experimental Methods Using mOCR-Myo

Unless otherwise noted, catalytic reactions were performed in 4 mL individually-capped vials or in 1.2 mL vials as part of a 96-well array fitted with a screw on cover. Reactions were either (1) assembled in a nitrogen atmosphere glove box or (2) assembled on the bench. In the latter case, the headspace of the vial purged with nitrogen through a septum cap. Solutions of Ir(Me)-PIX-mOCR-Myo were gently degassed on a Schlenk line (3 cycles vacuum/refill) before being pumped into a glove box in sealed vials. Organic reagents were added as stock solutions in acetonitrile (MeCN), such that the final amount of MeCN in the reaction was approximately 8% by volume. Protein catalysts were diluted to reaction concentration in Tris buffer (10 mM, pH=8.0) before being added to reaction vials. Unless otherwise noted, all reactions were performed with catalysts generated from a 1:2 ratio of [M]-cofactor:apo protein, with 0.5% catalyst loading with respect to [M] cofactor and limiting reagent. All reactions were conducted in a shaking incubator (20° C., 16 hours 275 rpm)

Example 37. Catalysis of MPDA Insertion by mOCR-Myo with Diverse [M]-PIX Cofactors To assess the activity of 64 [M]-mOCR-Myo proteins from Example 34, we evaluated them as catalysts for a series of reactions, including transformations for which there are no reported examples catalyzed by either native or artificial enzymes. To test catalytic S—H insertion, catalyst solution (240 µL, 0.1 mM protein, 0.24 µmol) was added to a vial. A stock solution of the appropriate thiol (2.5 µmol in 10 uL MeCN) was added, followed by a stock solution of the appropriate diazo compound (5 µmol in 10 µL MeCN).

We first evaluated this array of catalysts for the insertion of methyl phenyldiazoacetate (MPDA, 2) into the S—H bond of thiophenol (1), which we expected to be catalyzed by a range of the constructs. Indeed, catalysts containing various M-PIX produced desired thioether 3, verifying that the protocol generates active catalysts. Enzymes containing the Fe(Cl)-PIX, Ir(Cl)-PIX, and Cu-PIX cofactors were the most active, furnishing 3 with 40-53 turnovers. These studies further showed that the identity of the axial ligand supplied by the protein scaffold strongly influences the catalytic activity of the unnatural systems as it does for Fe-PIX enzymes. For example, the reaction catalyzed by Cu-PIX ligated with glutamic acid (H93E) occurred with 40 TON, while that catalyzed by other Cu-PIX myoglobins occurred with <15 TON. The enzyme containing Ir(Cl)-PIX was the most active overall (53 TON), but this high activity was observed only when the Ir was ligated by carboxylates (H93D and E). Considering these results, we prepared the cofactor Ir(Me)-PIX, which contains a methyl group as the non-labile axial ligand. Enzymes formed from the Ir(Me)-PIX cofactor were the most active enzymes for carbene insertion into the thiol, reacting with up to 100 turnovers.

Figure 11:
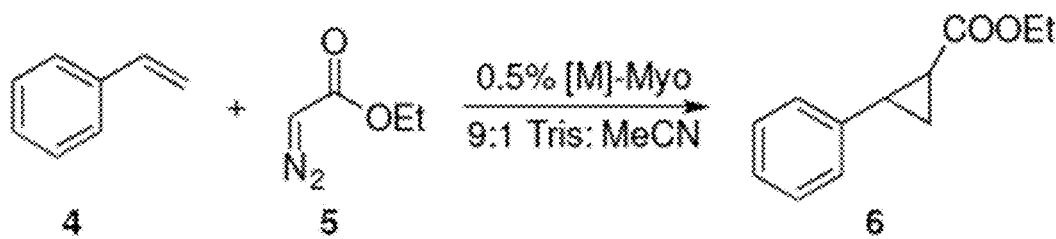
FIG. 11 presents results of cyclopropanation of styrene with ethyl diazoacetate (EDA) catalyzed by an array of 64 artificial mOCR-myoglobins generated with eight, single-step affinity chromatography purifications of protein scaffolds. TON=turnover number.

Example 38. Catalysis of Cyclopropanation by mOCR-Myo with Diverse [M]-PIX Cofactors To test catalytic cyclopropanation, catalyst solution (240 µL, 0.1 mM protein, 0.24 mol) was added to a vial. A stock solution of the appropriate olefin (2.5 µmol in 10 µL MeCN) was added, followed by a stock solution of the appropriate diazo compound (15 µmol in 10 µL MeCN). We evaluated the array of [M]-mOCR-Myo from Example 34 for the cyclopropanation of styrene (4, FIG. 11) with ethyl diazoacetate (5, EDA) to determine if systems containing non-native metals would be more reactive than those containing iron for this abiological reaction. Native Fe-PIX formed highly active catalysts for this reaction. However, we found that unnatural enzymes formed from Ru(CO)-PIX, Ir(Cl), and Ir(Me)-PIX were as active or more active than the Fe-PIX enzymes and that Ir(Me)-PIX was, again, the most active enzyme for this abiological process.

Figure 12:
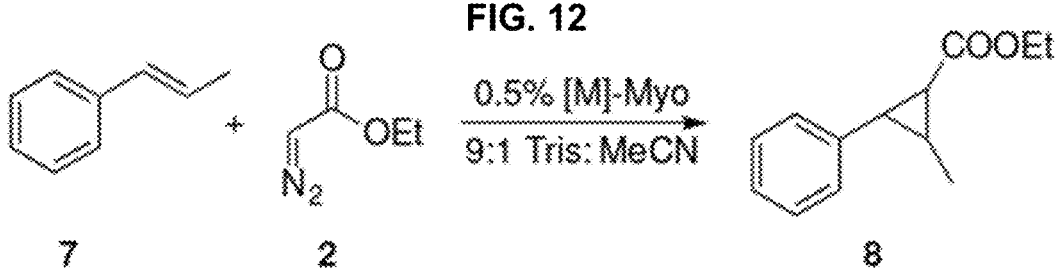
FIG. 12 presents results of cyclopropanation of trans-β-Me-Styrene with EDA catalyzed by an array of 64 artificial mOCR-myoglobins generated with eight, single-step affinity chromatography purifications of protein scaffolds. TON=turnover number.

To probe whether the abiological metal centers would generate enzymes that react with a broader scope of substrates and wider range of transformations than those catalyzed by their native Fe-analogs, we assessed the catalytic activity of the array from Example 34 for two unknown enzymatic reactions: cyclopropanation of less reactive, β-substituted styrenes with EDA and insertions of carbenes into C—H bonds. For the cyclopropanation of trans-β-methylstyrene (7, FIG. 12), only the abiological Rh, Ru, and Ir catalysts generated the addition product 8; Fe-PIX enzymes were completely inactive. Again, the Ir(Me)-PIX enzyme was the most active. Further studies on the scope revealed that the enzymes containing Ir(Me)-PIX also catalyze the previously unknown enzymatic cyclopropanation of aliphatic alkenes. The reaction of 1-octene with EDA generated the cyclopropane with up to 40 turnovers (Table 3).

TABLE 3

| Entry | [1-octene] | [EDA] | Method | TON | er |
|---|---|---|---|---|---|
| A | 10 mM | 60 mM | Standard Method | 20 | 85:15 |
| B | 10 mM | 60 mM | Syringe Pump Addition of EDA (1 hr) | 40 | |
| C | 10 mM | 60 mM | Syringe Pump Addition of EDA (12 hr) | 20 | 91:9 |

Figure 13:
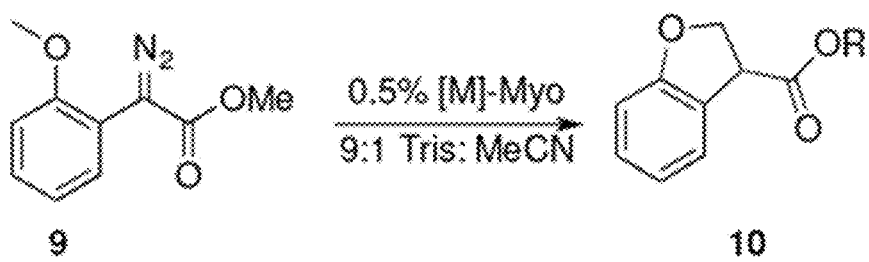
FIG. 13 presents results of intramolecular insertion of 2-OMe-MPDA into a C—H bond catalyzed by an array of 64 artificial mOCR-myoglobins generated with eight, single-step affinity chromatography purifications of protein scaffolds. TON=turnover number.
Figure 14:
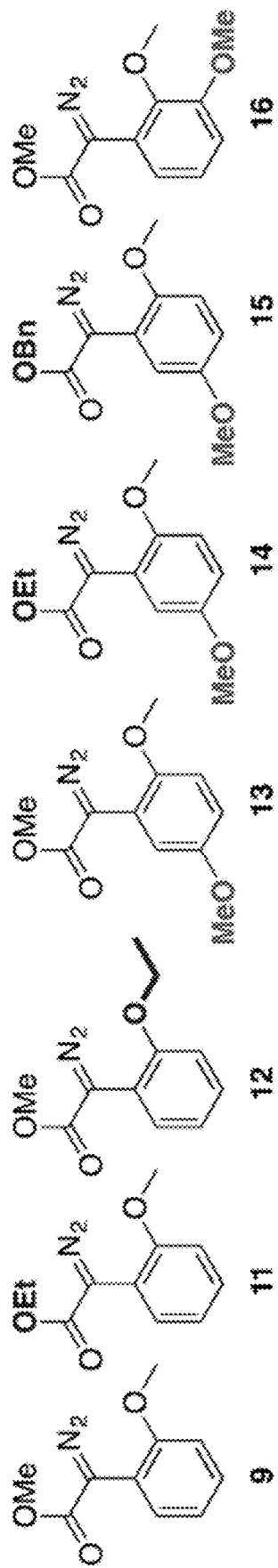
FIG. 14 presents a summary of activities and selectivities for reactions catalyzed by Ir(Me)-mOCR-Myo. Above: Substrates used for C—H insertion reactions. Below (left): Selectivities obtained from evaluation of eight initial mutants. Below (right): Highest selectivities obtained from directed evolution.
Figure 15:
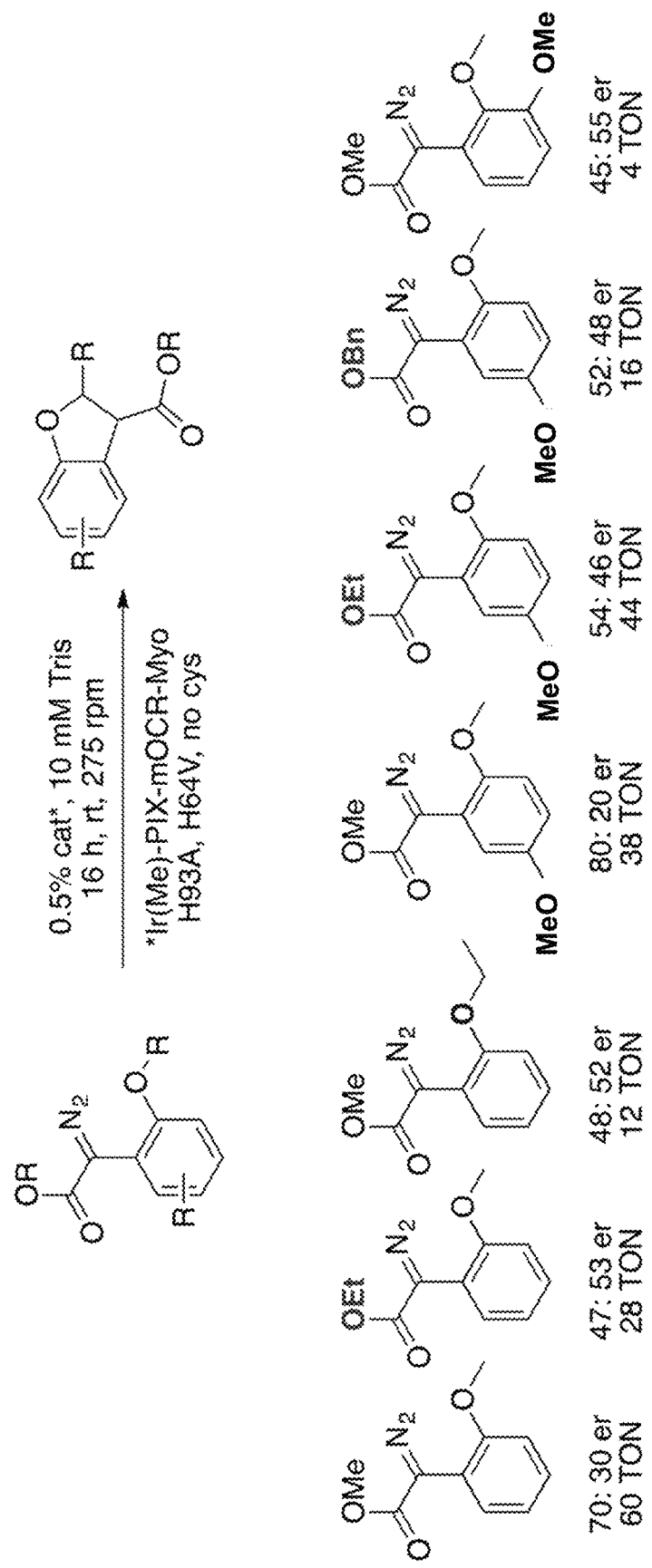
FIG. 15 presents comparisons of activities and selectivities for C—H insertion reactions catalyzed by the same Ir(Me)-PIX-mOCR-Myo mutant (H93A/H64V) for substrates varied at the arene, ester, and alkoxy-functionalities. Turnover numbers are determined by GC.

Example 39. Catalysis of Carbene Insertion by mOCR-Mo with Diverse [M]-PIX Cofactors To test catalytic intramolecular C—H insertion a stock solution of the appropriate diazo compound (2.5 μin 20 μL MeCN) was added to a vial followed by the catalyst solution (240 μL, 0.1 mM protein, 0.24 μmol). We evaluated [M]-mOCR-myo variants from Example 34 for the insertion of carbenes into C—H bonds (FIG. 13), a reaction class that has not been accomplished with native or artificial metalloenzymes. The reaction of 9 catalyzed by Ir(Me)-PIX enzymes (the most active catalysts identified) formed enantioenriched dibenzohydrofuran 10 with selectivities ranging from 38:64 er (H93G) to 56:44 er (H93A). The carbene C—H insertion reaction of six additional substrates 11-16 containing varied ester, arene, and alkoxy functionalities (FIG. 14) also occurred; the reactivity of these substrates and the enantioselectivity of the reactions varied, suggesting that significant interactions exist between the reactant and the protein (FIG. 15). The observation of enantioenriched products, albeit in modest enantiomer ratios with this first set of mutants, again, verifies that the reactions occur at the metal center of the cofactor embedded within the protein. Together, these results show that the multi-dimensional evaluation of reconstituted PIX-enzymes can identify new, artificial metalloenzymes that are more active for a range of reactions than are those containing the native metal, including reactions for which biological Fe-PIX-proteins are inactive.

Example 40. Design of a Size-Selective Inhibitor of Free Cofactor

To facilitate the screening process, we sought a size-selective inhibitor that would bind to any free cofactor released in the event of protein denaturation during the reaction, but that would be excluded from the porphyrin binding due to steric interactions with the protein scaffold. Such an inhibitor would enable a more direct comparison of the inherent selectivities of different mutants. Several classes of molecules are known to be potent inhibitors of Fe-PPIX-proteins, including imidazoles, pyridines, and isonitriles (Barrick (1994) Biochemistry 33:6546).

To ascertain whether size-selective inhibition could be realized, an assay was developed based on the enantioselective cyclopropanation of 4-OMe-styrene with EDA catalyzed by Fe-PPIX-Myo. The reaction catalyzed by the mutant Fe-PPIX-Myo-V68A occurs in 90% ee, whereas the reaction catalyzed by the combination of Fe-Myo-V68A and Ir(Me)-PPIX (free cofactor) occurs in lower ee (30%), due to the unselective Ir-PPIX cofactor. Therefore, we expected that reactions catalyzed by this combination of catalysts in the presence of a size-selective inhibitor would occur with ee's reflecting that of the Fe-PPIX-Myo-V68A protein. Using this assay, a series of inhibitors based on pyridines, imidazoles, and isocyanides were evaluated. Electron rich, sterically bulky pyridines were determined to be the best inhibitors; reactions catalyzed by the combination of Fe-Myo-V68A and Ir(Me)-PPIX in the presence of the combination of Fe-Myo-V68A and Ir(Me)-PPIX occurred with the highest yields and selectivities. A morpholine-substituted pyridine was chosen for further study, due to its effectiveness as a selective inhibitor of the free Ir-porphyrin and its high water solubility. An investigation of the combination of inhibitor concentration (0-10 mM), reaction concentration (10-40 mM substrate), and ratio of Ir(Me)-PPIX:Myo (0.5-1.0) revealed that high concentrations of inhibitor both suppressed yield and lowered the selectivity of the reaction, while 1-10 equiv. of inhibitor (relative to catalyst) permitted higher selectivities than were possible without the inhibitor. These effects were even higher at higher reaction concentrations and higher metallation levels, suggesting higher catalyst stability in the presence of lower reaction concentrations and limited inhibitor levels. Based on these results, 10 mM substrate, 1 mM inhibitor, 0.10 mM apo protein, and 0.05 mM cofactor were chosen as conditions for the directed evolution of Ir(Me)-mOCR-Myo catalysts for the C—H insertion reaction.

Example 41. Evolution of Enantioselective Ir(Me)-PIX Myoglobins

Figure 4:
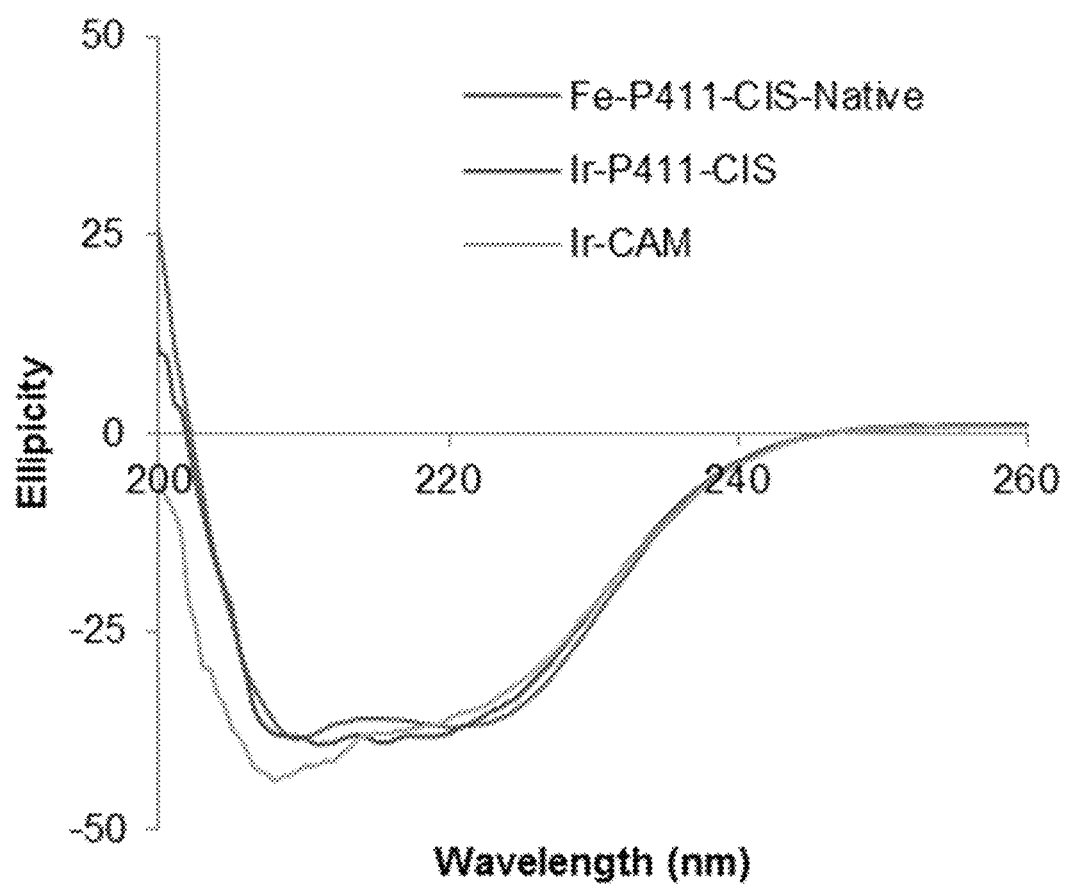
FIG. 4 presents the CD and UV spectra of native and artificially metallated proteins.
Figure 5:
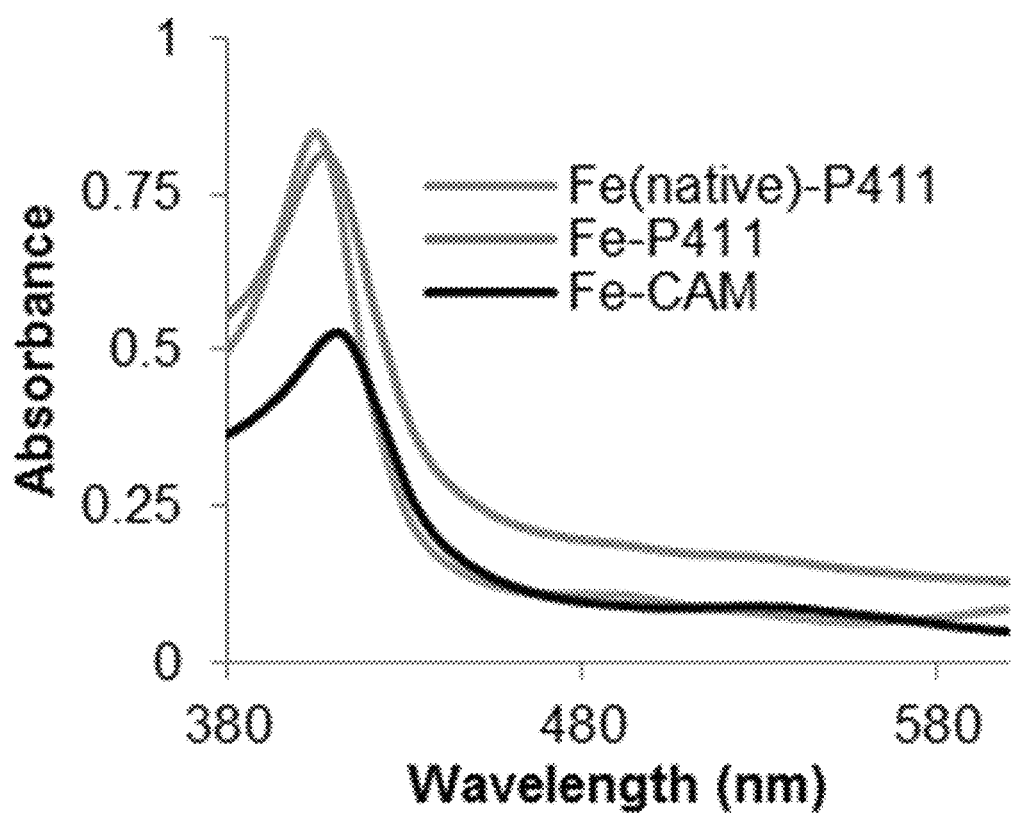
FIG. 5 presents the CD and UV spectra of native and artificially metallated proteins.
Figure 6:
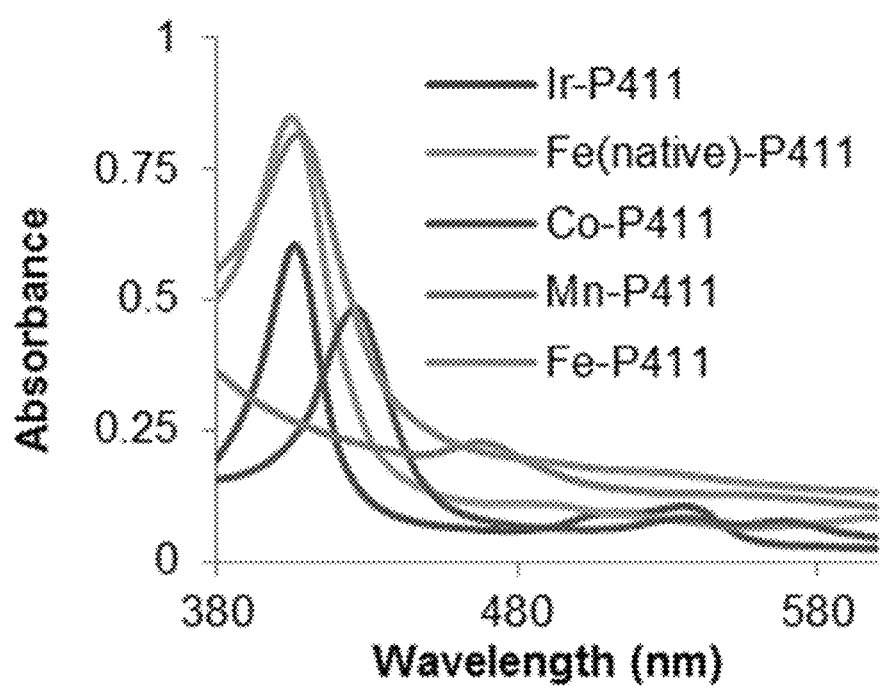
FIG. 6 presents the CD and UV spectra of native and artificially metallated proteins.
Figure 16:
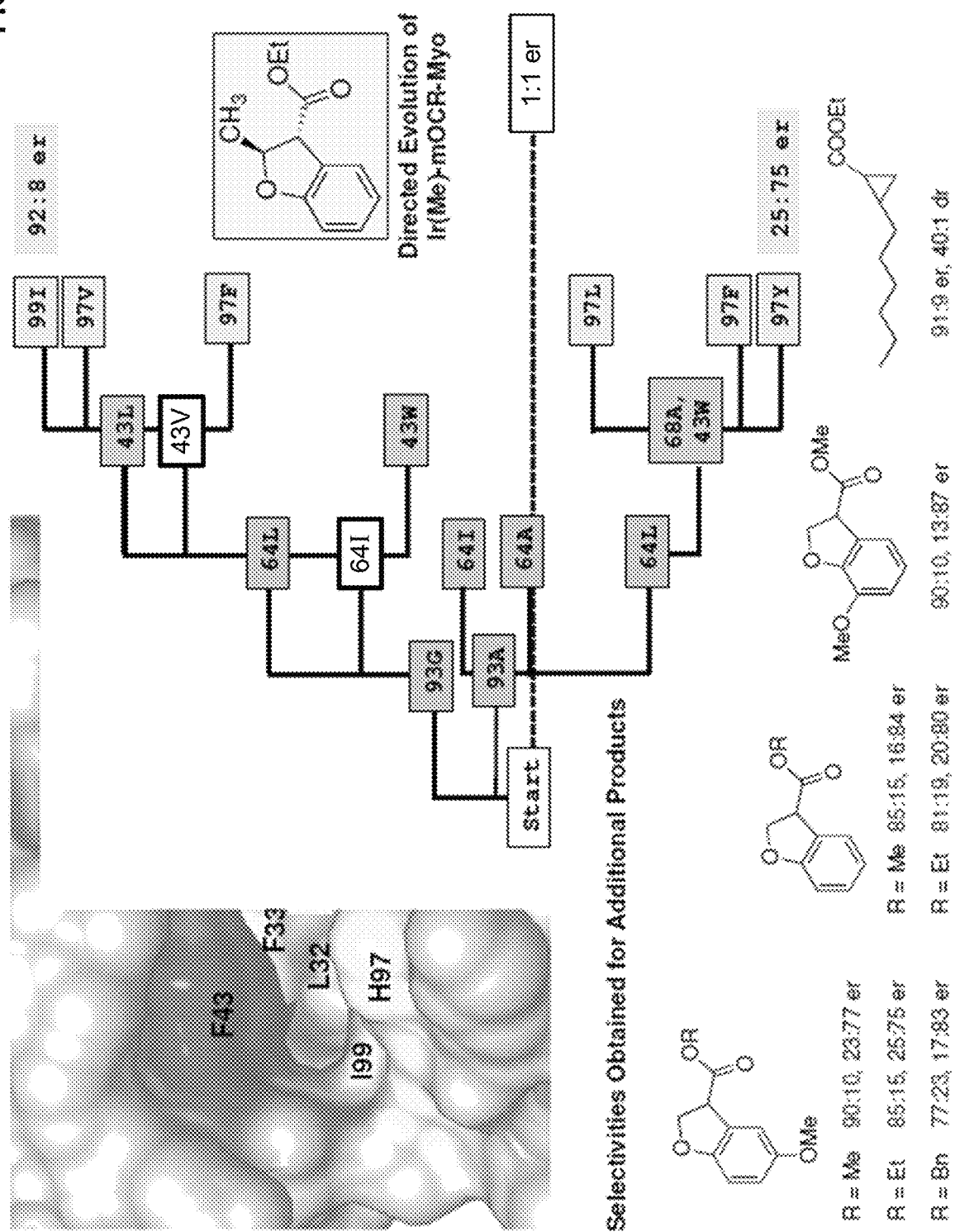
FIG. 16 illustrates a directed evolution strategy used to obtain Ir(Me)-mOCR-Myo mutants capable of producing either enantiomer of the products of C—H insertion reactions of SAR substrates. Inner sphere, middle sphere, and outer sphere residues are highlighted in the depiction of the active site and in the evolutionary tree (Image produced in Chimera from PDB: 1MBN (Watson (1969) *Protein Stereochem.* 4:299)).
Figure 17:
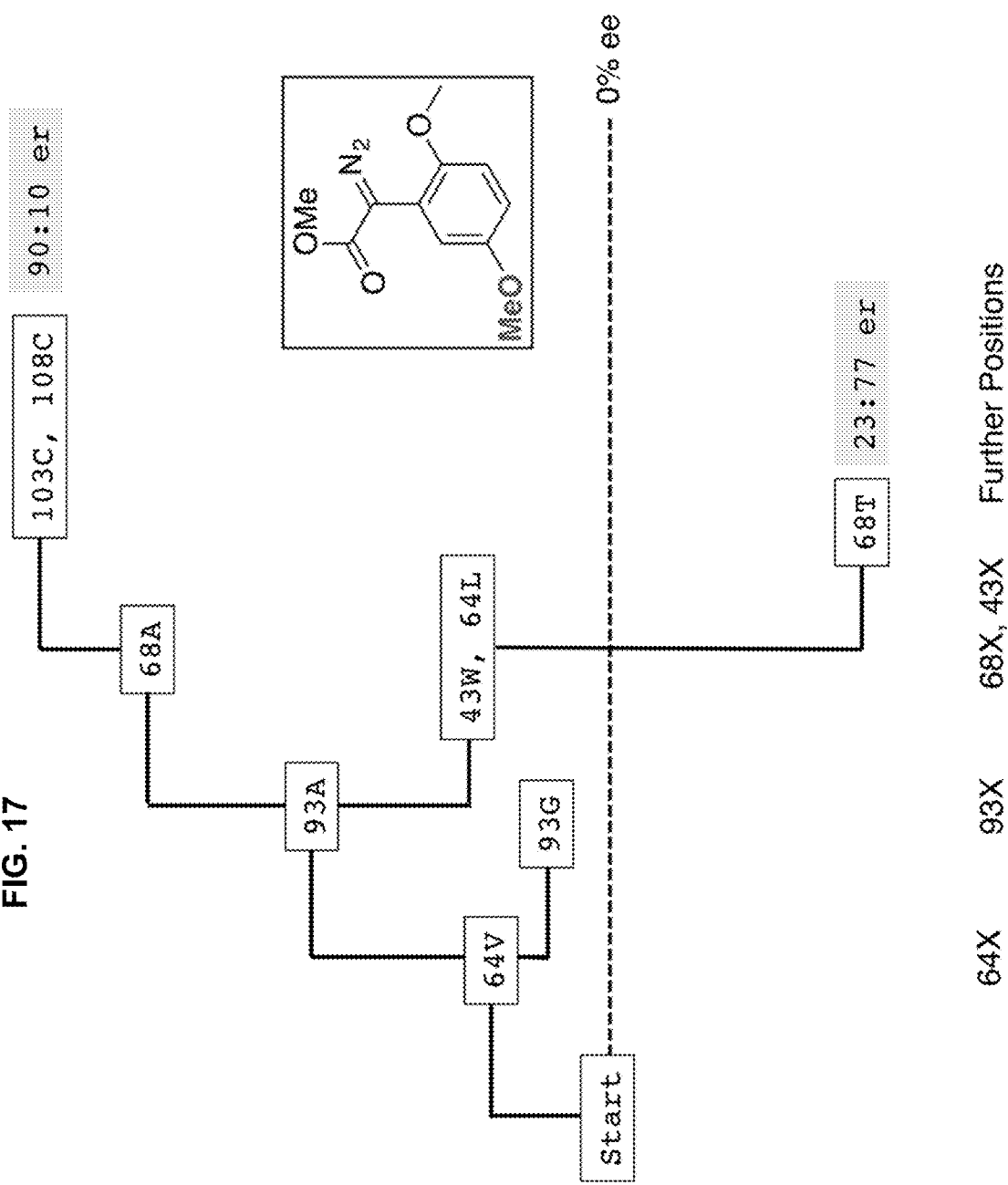
FIG. 17 illustrates a directed evolution tree showing the progression toward the most selective catalyst for C—H insertion into a substrate.
Figure 18:
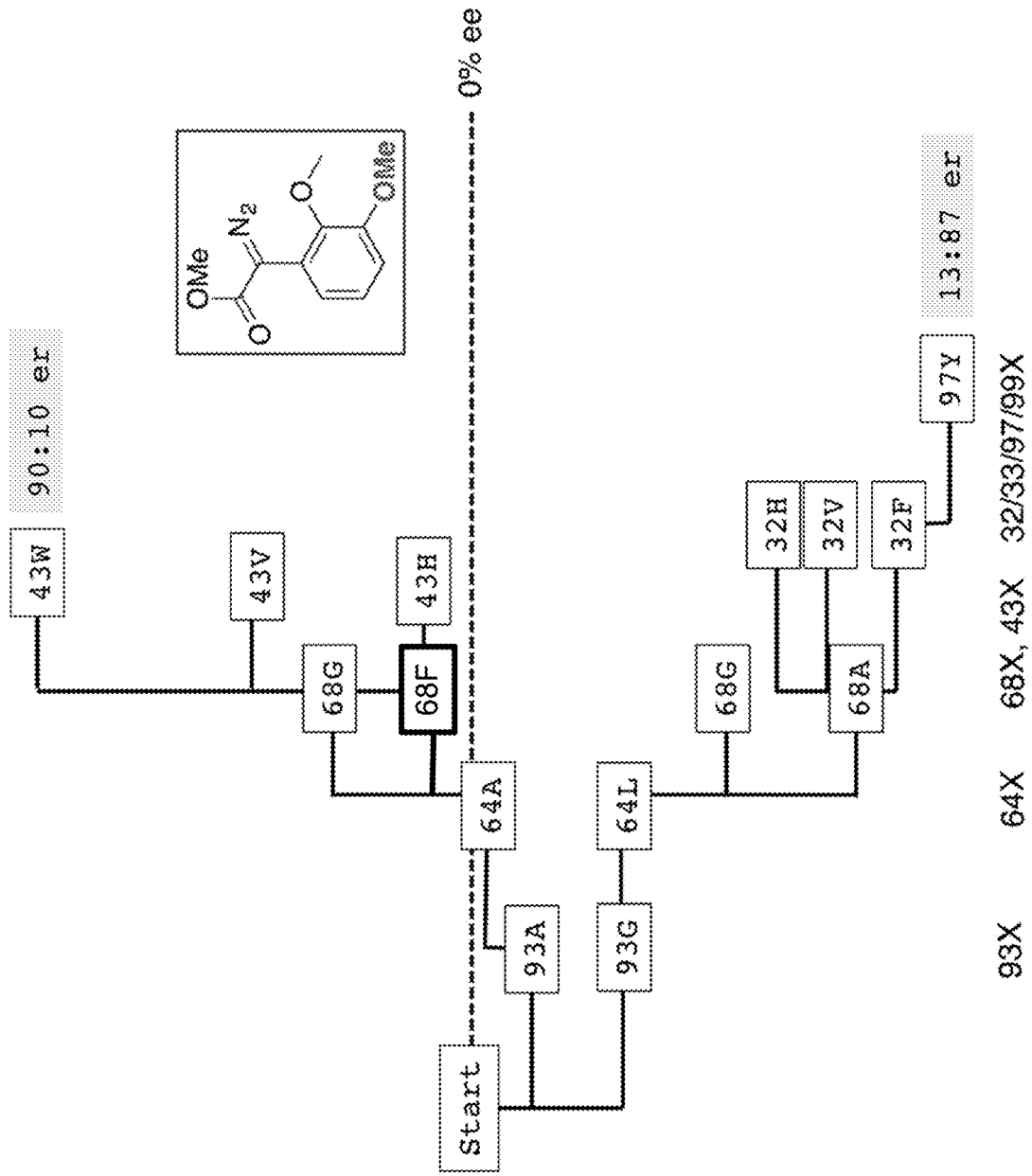
FIG. 18 illustrates a directed evolution tree showing the progression toward the most selective catalyst for C—H insertion into a substrate.
Figure 19:
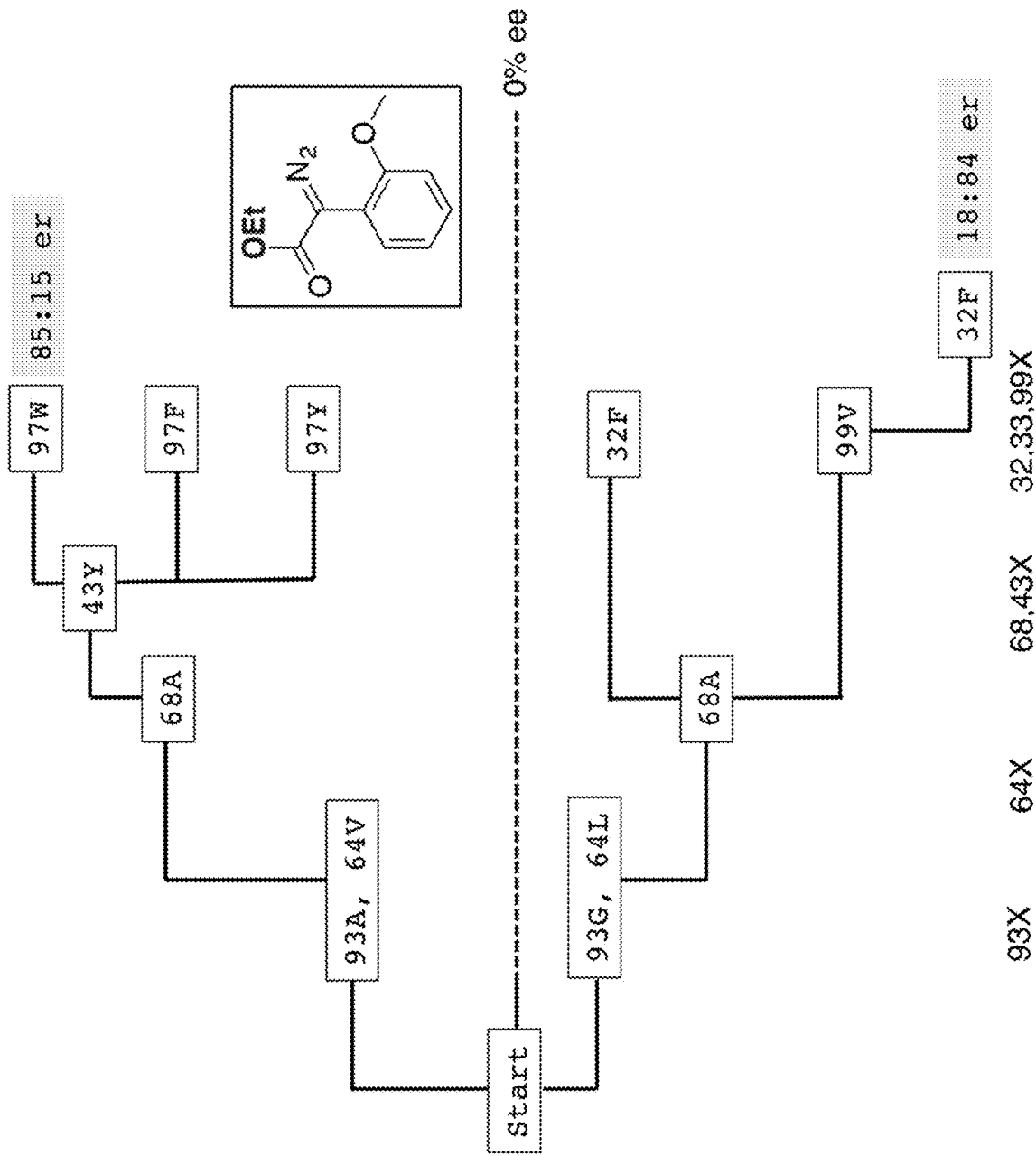
FIG. 19 illustrates a directed evolution tree showing the progression toward the most selective catalyst for C—H insertion into a substrate.

To evolve enantioselective myoglobins containing Ir(Me)-PIX, we followed a hybrid strategy based on stepwise optimization of three sets of amino acids, at positions progressively more distal from the binding site of the metal and substrate (FIG. 16). To retain the hydrophobicity of the PIX-binding site, a limited set of amino acid permutations was chosen for each targeted position. The axial ligand (H93) and the residue directly above the metal center (H64) were modified first (FIG. 4). Considering previous results (Example 37, Example 38, and Example 39), the axial ligand was mutated to alanine or glycine, and residue H64 was mutated to alanine, valine, leucine and isoleucine. These eight mutants were expressed and their Ir(Me) variants evaluated as catalysts for the insertion reactions for seven substrates (FIG. 14). For each substrate, at least one mutant reacted with higher enantioselectivity than the native protein containing the H93/H64 binding site (FIG. 14). Moreover, this set of eight mutants contained enzymes that form either enantiomer of the product from reaction of three of the seven substrates. For example, mutant H93A/H64L catalyzed the C—H insertion of substrate 9 with 77:23 er, while the mutant H93G/H64L catalyzed the same reaction with a reversed enantioselectivity: 26:74 er.

In the second phase of the evolution, we prepared enzymes having variations to residues F43 and V68, which are located further from the metal, but within the binding site of the substrate (FIG. 16). Once again, a limited number of amino acids were selected for each position (F43Y,W,L,I,T,H,V and V68A,G,F,Y,S,T), such that plasmids encoding 55 derivatives of each of the initial eight mutants were targeted.

Site-directed mutagenesis using mixed primers yielded a plasmid library covering 69% of these targeted mutants. From this library, mutants were selected, expressed, reconstituted with Ir(Me)-PIX, and evaluated as catalysts for reaction of the seven substrates for the C—H insertion reaction. The reactivity and selectivity of the mutants that were expressed earlier were used to select subsequent mutants for evaluation from the prepared library of plasmids. In total, 225 additional mutants were evaluated, and the results in Table 4 below revealed that a different mutant was the most selective catalyst for each substrate.

positions H93 and H64 catalyzed the cyclopropanation of β-Me-styrene and 1-octene with EDA with modest enantioselectivity (FIG. 14). However, reactions catalyzed by enzymes generated for our studies on carbene insertions into C—H bonds containing mutations at position F43 and V68 occurred with higher enantioselectivity, including a mutant that reacted with 91:9 er and 40:1 dr for the cyclopropanation of 1-octene (FIG. 14, FIG. 16 and Table 6). These results underscore the potential to evolve myoglobins containing abiological active sites for enantioselective intermo-

TABLE 4

| | Mutant Providing (−) enantiomer | | | | | Mutant Providing (+) enantiomer | | | | |
|---|---|---|---|---|---|---|---|---|---|---|
| Substrate | H93X | H64X | F43X | V68X | er (TON) | H93X | H64X | F43X | V68X | er (TON) |
| 9 | A | V | — | F | 79:21 (42) | G | L | — | A | 23:77 (50) |
| 11 | G | L | L | A | 80:20 (68) | G | L | V | G | 31:69 (46) |
| 12 | G | I | V | — | 84:16 (62) | A | L | Y | G | 31:69 (36) |
| 13 | A | V | — | A | 90:10 (98)* | A | L | W | T | 23:77 (164) |
| 14 | G | L | Y | — | 84:16 (100) | A | V | I | T | 25:75 (138) |
| 15 | A | V | H | S | 77:23 (44) | G | L | L | G | 33:67 (42) |
| 16 | A | A | W | G | 90:10 (52) | G | L | — | A | 20:80 (10) |

In the third phase of the evolution, the most selective mutants for each substrate identified from the second round of mutations were further modified at four positions (L32 and F33, which are adjacent to the substrate binding site; and H97 and I99, which are adjacent to the axial ligand) more remote from the substrate binding site than the positions modified in the second round (FIG. 16). From the obtained plasmid library encoding these final mutations (L32V,I,F,H,W,Y; F33V,L,I,H,W,Y; H97V,L,I,F,W,Y; I99V,L,F,H,W,Y), 217 mutant proteins were evaluated. In total, the directed evolution of Ir(Me)-myoglobins by this methodology uncovered enzymes that catalyze the insertion reaction to form either enantiomer for all seven substrates, with selectivities up to 92:8 er, TON up to 194, and yields up to 97% (FIG. 16, FIG. 17, FIG. 18, FIG. 19, and Table 5). Furthermore, the reactions can be carried out at larger scale; substrate 16 (28 mg) forms the product in 80% isolated yield with the same enantioselectivity (90:10 er) as observed at lower scale. These results demonstrate that the direct expression of apo-Myo, insertion of Ir(Me)-PIX, and subsequent directed evolution of the resulting enzymes is a strategy that creates stereoselective catalysts for reactions that have not been catalyzed by any natural or unnatural enzymes previously.

lecular and intramolecular reactions of substrates possessing diverse shapes and functional groups.

TABLE 6

| Entry | [1-octene] | [EDA] | Method | TON | er |
|---|---|---|---|---|---|
| A | 10 mM | 60 mM | Standard Method | 20 | 85:15 |
| B | 10 mM | 60 mM | Syringe Pump Addition of EDA (1 hr) | 40 | |
| C | 10 mM | 60 mM | Syringe Pump Addition of EDA (12 hr) | 20 | 91:9 |

Example 42. Synthetic Scale Reaction with mOCR-Myo

Catalyst solution (15 mL, 0.1 mM protein (mOCR-myo-93G,64L,43L,99F)) was added to a Schlenk flask and gently degassed on a Schlenk line (3 cycles vacuum/refill). A solution of substrate 11 (FIG. 14, 33 mg, 0.5 mmol in 600 uL DMF) was added. The flask was sealed and gently shaken (120 rpm) at 20° C. overnight. The reaction was diluted with brine (30 ml) and extracted with ethyl acetate (3.50 ml). If required, the phase separation was achieved by centrifuging

TABLE 5

| | Mutations Providing (−) enantiomer | | | | Mutations Providing (+) enantiomer | | | |
|---|---|---|---|---|---|---|---|---|
| Substrate | H93/H64 | F43/V68 | Additional Mutations | er (TON) | H93/H64 | F43/V68 | Additional Mutations | er (TON) |
| 9 | 93A, 64L | 43L | 33V | 85:15 (134)* | 93G, 64L | 68A | 32F, 99V | 16:84 (62) |
| 11 | 93A, 64V | 43Y, 68A | 97W | 81:19 (128) | 93G, 64L | 68A | 99V | 20:80 (26)* |
| 12 | 93G, 64L | 43L | 99F | 92:8 (92) | 93A, 64L | 68A, 43W | 97Y | 25:75 (68) |
| 13 | 93A, 64V | 68A | 103C, 108C | 90:10 (98) | 93A, 64L | 43W, 68T | — | 23:77 (164) |
| 14 | 93A, 64L | 43W, 68A | 33I | 85:15 (86) | 93A, 64V | 43I, 68T | — | 25:75 (138) |
| 15 | 93A, 64V | 43H, 68S | — | 77:23 (44) | 93A, 64V | 68A | 33V, 97Y | 17:83 (42) |
| 16 | 93A, 64A | 43W, 68G | — | 90:10 (52) | 93G, 64L | 68A | 32F, 97Y | 13:87 (144) |

Having demonstrated the potential to evolve Ir(Me)-mOCR-Myo, we sought to evolve enantioselective catalysts for the cyclopropanation reactions that are not catalyzed by heme enzymes. The eight mutants with variations only at (2000 rpm, 3 minutes) the mixture. The combined organic fractions were washed with sat. $NH_4Cl$ (5·30 ml), brine (30 ml), dried over $MgSO_4$. After filtration, the volatile material from the filtrate was evaporated under reduced pressure. The residue was purified by column chromatography on silica gel, with a mixture of hexanes and ethyl acetate (100:0 to 95:5 gradient) as the eluent. Fractions of the pure product were combined, and the solvent evaporated, yielding 10 mg (35%) of ethyl 2,3-dihydrobenzofuran-3-carboxylate. Er: 86:14, $[\alpha]_D^{20}$=+40°, (c=0.6, CHCl$_3$).

Example 43. Evolution of Ir(Me)-PIX CYP119 Enzymes

Upon combining the apo forms of P450-BM3, CAM, and CYP119 with 1 equiv. of Ir(Me)-PIX cofactor, the Ir(Me)-PIX is incorporated into the protein within 5 minutes, as evidenced by co-elution of the porphyrin with the protein in a desalting (size-exclusion) column and observation of a 1:1 cofactor:CYP119 assembly by native-nanospray ionization mass spectrometry (native nanoESI-MS). As hypothesized, the Ir(Me)-PIX protein formed from CYP119 had a much higher $T_m$ (69° C.) than those formed from P450-BM3 (45° C.) or P450-CAM (40° C.). This higher $T_m$ suggested that enzymes created from the scaffold of CYP119 could be used at elevated temperatures. Thus, this protein was used for our studies on catalytic reactions.

Figure 20:
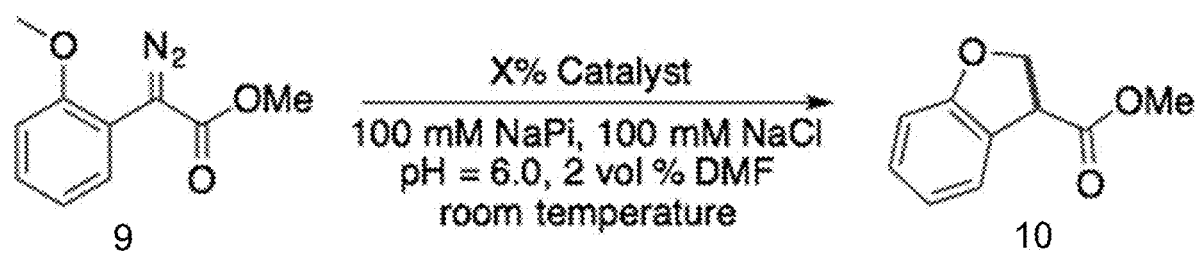
FIG. 20 presents a scheme for a model reaction converting diazoester to dihydrobenzofuran.
Figure 21:
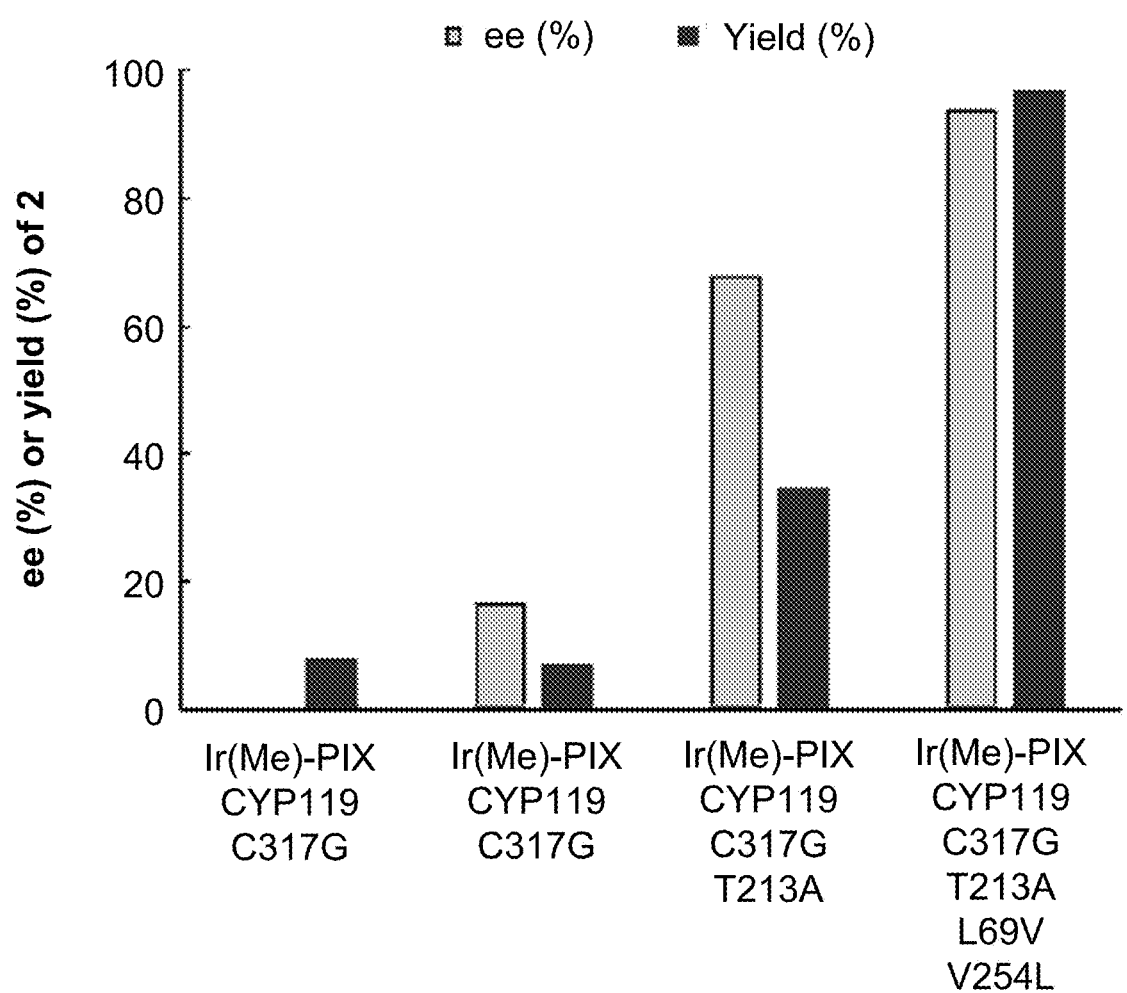
FIG. 21 presents the enantioselectivity and yields for the formation of dihydrobenzofuran catalyzed by sequentially evolved variants of CYP119 (0.17% catalyst loading, 10 mM substrate).

By studying the model reaction (FIG. 20) to convert diazoester 9 into dihydrobenzofuran 10, which does not occur in the presence of natural Fe-PIX enzymes, we found that the activity and selectivity of Ir(Me)-PIX CYP119 enzymes are readily evolved through molecular evolution of the natural substrate binding site of the CYP119 scaffold. The wild type (WT) Ir(Me)-CYP119 enzyme and its variant C317G (bearing a mutation that introduces space to accommodate the axial ligand of the Ir(Me)-PIX cofactor) catalyze the intramolecular C—H carbene insertion reaction to form 10, although with low rates (TOF=0.23 and 0.13 min$^{-1}$) and enantioselectivities (ee=0% and 14%) for reactions conducted with 5 mM 9 and 0.1 mol % catalyst. To identify mutants that form 10 with higher rates and enantioselectivity, we used a directed evolution strategy targeting the residues close to the active site (L69, A209, T213, and V254, FIG. 21). To retain the hydrophobicity of the active site, only hydrophobic and uncharged residues were introduced (V, A, G, F, Y, S, T) by site-directed mutagenesis to prepare a library of 24 double mutants of CYP119. The mutant C317G, T213G formed 10 with 68% ee and 80-fold higher activity (TOF=9.3 min$^{-1}$) than the single mutant C317G under the same reaction conditions described previously. Two additional rounds of evolution, in which approximately 150 additional variants were analyzed, identified the quadruple mutant C317G, T213G, L69V, V254L (CYP119-Max) that formed 10 with 94% enantioselectivity and with an initial TOF of 43 min$^{-1}$. This rate is more than 180 times faster than that of the WT variant. Such rates are unprecedented for abiological transformations catalyzed by artificial metalloenzymes with high enantioselectivity.

Figure 22:
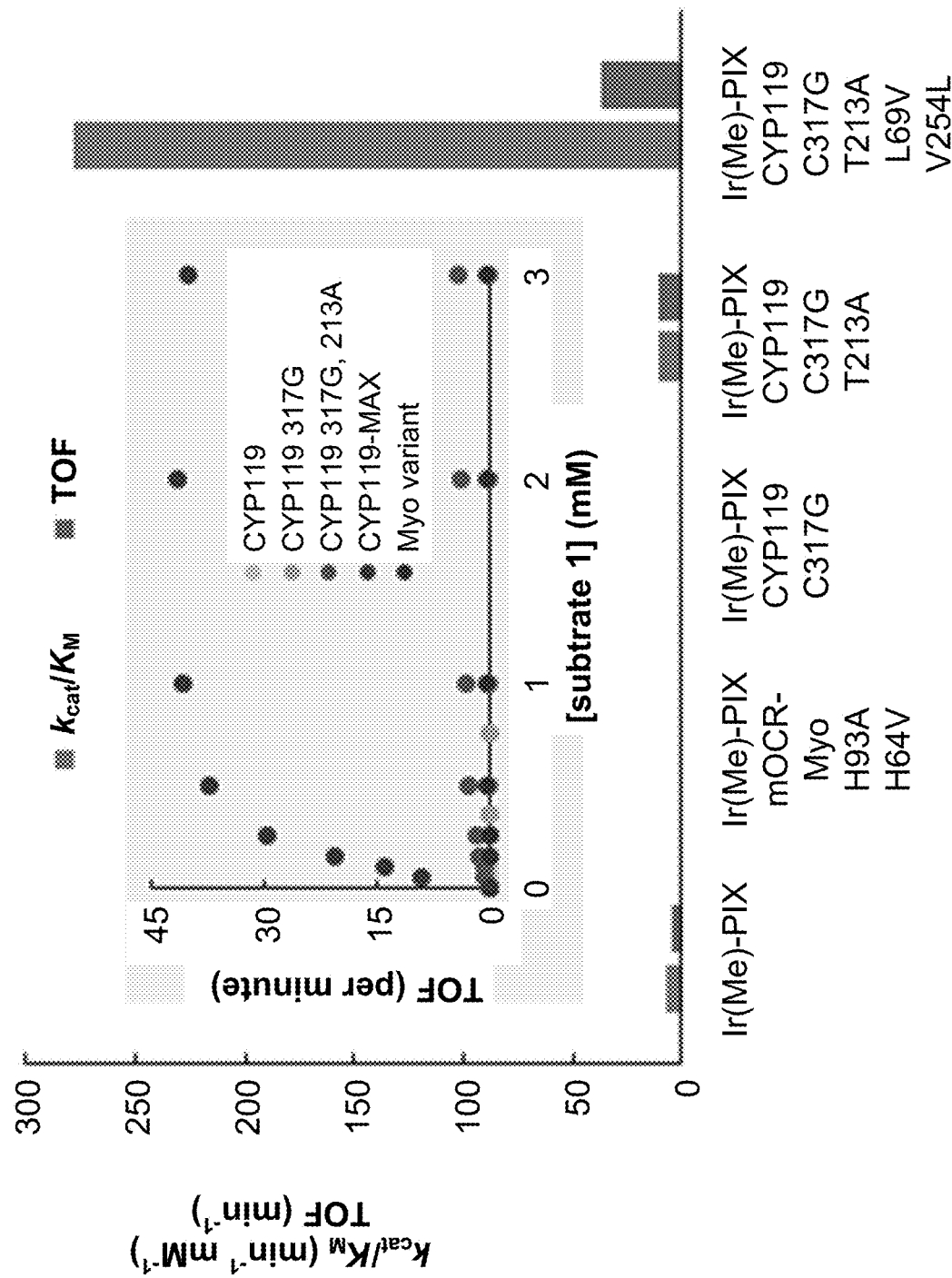
FIG. 22 presents kinetic parameters describing the formation of dihydrobenzofuran by variants of CYP119 using 0.1% catalyst and 5 mM substrate; for free Ir(Me)-PIX, $k_1$ (the first order kinetic constant) is listed instead of $k_{cat}/K_M$.

Kinetic studies (FIG. 22) provided insight into the origin of the differences in the enzymatic activity between the various mutants of Ir(Me)-CYP119. In particular, we determined the standard Michaelis-Menten kinetic parameters ($k_{cat}$ and $K_M$) for the mutants at each stage of the evolution. Using these terms, we determined the catalytic efficiency of each enzyme, which is defined as $k_{cat}/K_M$ and considered one of the most relevant parameters for comparing engineered enzymes to natural enzymes (Bar-Even et al. (2011) *Biochemistry* 50:4402). The affinity of substrate 1 for the WT enzyme is weak, as revealed by a high $K_M$ (>5 mM). The single mutant C317G, which lacks a sidechain at this position that could act as an axial ligand, exhibits higher substrate affinity ($K_m$=3.14 mM), catalytic activity ($k_{cat}$=0.22 min$^{-1}$), and, therefore, overall enzyme efficiency ($k_{cat}/K_M$=0.071 min$^{-1}$ mM$^{-1}$) than the WT enzyme. The double mutant T213G, C317G of Ir(Me)-CYP119 reacts with far more favorable Michaelis-Menten parameters ($k_{cat}$=4.88 min$^{-1}$ and $K_M$=0.43 mM, $k_{cat}/K_M$=11 min$^{-1}$ mM$^{-1}$) than those of this single mutant C317G. The incorporation of two additional mutations (L69V, V254L) led to further improvements of both $k_{cat}$ and $K_M$, creating an enzyme (CYP119-Max) with 4,000-times higher efficiency ($k_{cat}$=48.0 min$^{-1}$, $K_M$=0.17 mM, and $k_{cat}/K_M$=278 min$^{-1}$ mM$^{-1}$) than that of the WT system. These kinetic parameters mark a vast improvement over those of the variant of myoglobin Ir(Me)-PIX-mOCR-Myo H93A, H64V ($k_{cat}$=0.73 min$^{-1}$, $K_M$=1.1 mM, and $k_{cat}/K_M$=0.66 min$^{-1}$ mM$^{-1}$). Furthermore, the rates of reactions catalyzed by CYP119-Max at concentrations below $K_M$ are more than twenty times faster than those catalyzed by the free iridium-porphyrin in the presence of the same substrate concentration (TOF=21 min$^{-1}$ versus TOF=0.93 min$^{-1}$ at 0.17 mM 1), despite the fact that the free cofactor lacks any steric encumbrance near the metal site necessary to enable selective catalysis. These results show the value of conducting this iridium-catalyzed reaction within the enzyme active site to control selectivity and increase the reaction rate simultaneously.

A comparison of the kinetic parameters of reactions catalyzed by the Ir(Me)-PIX CYP119-Max enzyme to those of natural enzymes involved in intermediate and secondary metabolism, such as many cytochromes P450. This comparison indicates that Ir(Me)-PIX CYP119-Max reacts with kinetic parameters that are comparable to those of such natural enzymes. The binding affinity of Ir(Me)-CYP119-Max for the abiological substrate 1 is even higher than the affinity of P450s for their native substrates (compare $K_M$=0.17 mM for CYP119-Max to $K_M$=0.298 mM for the native substrate lauric acid of P450-BM3) and similar to the median $K_M$ value for natural enzymes (0.13 mM). In addition, the $k_{cat}$ of 48.0 min$^{-1}$ for this enzyme is within an order of magnitude of the median $k_{cat}$ of natural enzymes responsible for the production of biosynthetic intermediates (312 min$^{-1}$) and secondary metabolites (150 min$^{-1}$). This analysis demonstrates that direct replacement of the metal found in a natural metalloenzyme by an abiological metal creates artificial metalloenzymes that can be evolved into catalysts that react with tight binding and favorable preorganization of unnatural substrates, and thus with high activity and selectivity.

Figure 23A:
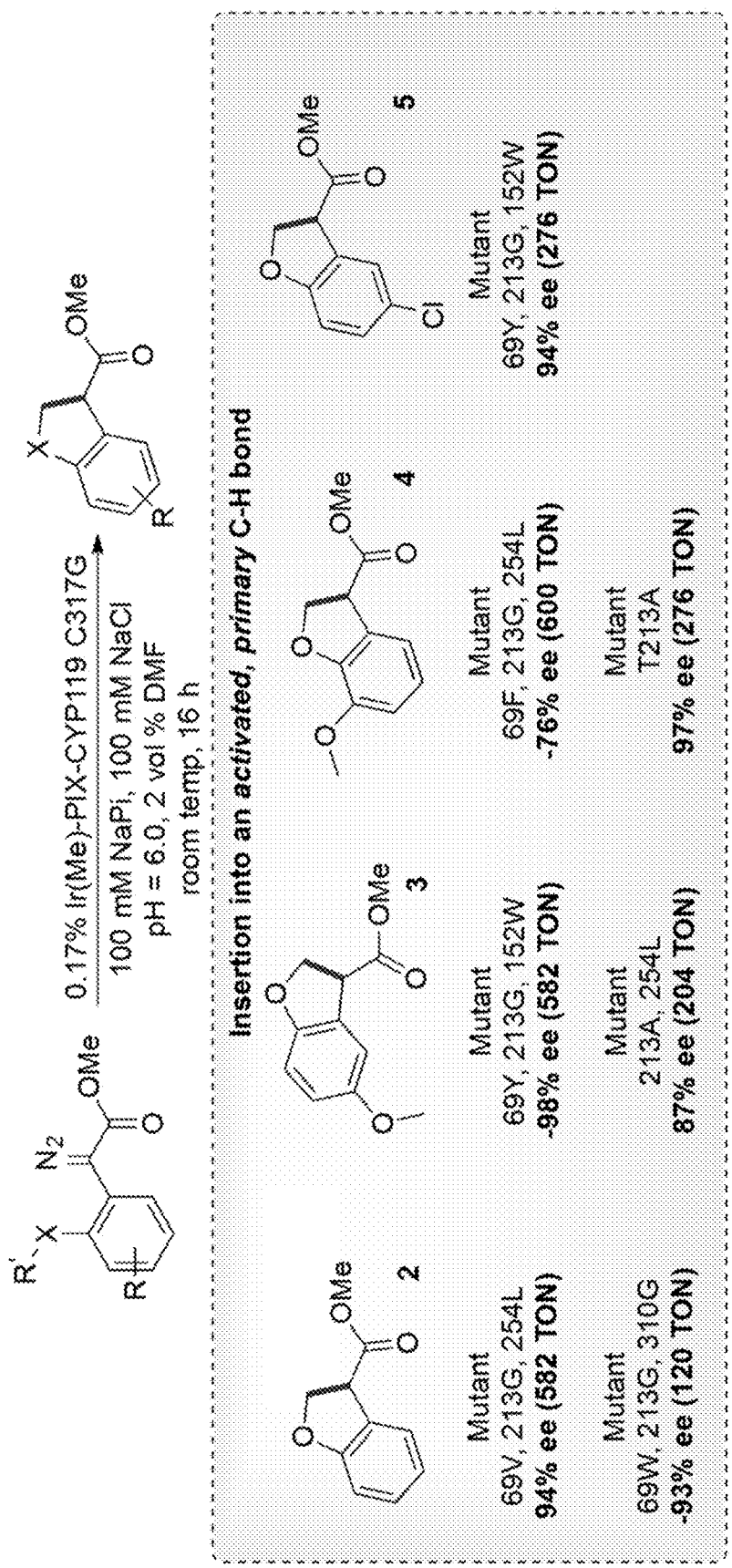

The potential to evolve proteins having advantageous enzyme-substrate interactions should also create the possibility to catalyze C—H carbene insertion reactions involving structurally diverse and less reactive substrates (FIG. 23). Directed evolution targeting high stereoselectivity led to suitable mutants to form products 3-7 in up to (+/−) 98% ee, in reactions conducted with a fixed catalyst loading (0.17 mol %). The reactions to form products 3-5 (FIG. 23) show that the enzyme reacts as selectively with substrates containing substituents on the aryl ring as it does for the unsubstituted 2 (FIG. 23). Such reactivity is relevant to contemporary synthetic challenges, as compound (S)-5 is an intermediate in the synthesis of BRL 37959—a potent analgesic—and was prepared previously by kinetic resolution (Bongen et al. (2012) *Chem. Eur. J.* 18:11063). This product was formed by variant 69Y-152W-213G in 94% ee. Product 6 (FIG. 23) results from carbene insertion into a secondary C—H bond, and product 7 (FIG. 23) results from carbene insertion into a sterically hindered, secondary C—H bond. Directed evolution furnished a mutant capable of forming 7 with high enantio- and diastereoselectivity favoring the cis isomer (90% ee, 12:1 dr (cis:trans)). The Ir(Me)-PIX enzymes based on myoglobin reported previously produced this product in only trace amounts, and the free Ir(Me)-PIX cofactor formed predominantly the trans isomer (3:1 dr, trans:cis). This reversal of diastereoselectivity from that of the free Ir(Me)-PIX cofactor to that of the artificial metalloenzyme highlights the ability of strong substrate-enzyme interactions to override the inherent selectivity of a metal cofactor or substrate.

Ir(Me)-CYP119-Max also catalyzes the insertion of carbenes into fully unactivated C—H bonds. Although substrates 1 and 7 (FIG. 23) are structurally similar, the primary C—H bonds in 7 are stronger and less reactive than those in 1, which are located alpha to an oxygen atom (Paradine and White (2012) *J. Am. Chem. Soc.* 134:2036). In fact, there are no metal catalysts of any type reported to form indanes by carbene insertion into an unactivated C—H bond with synthetically useful enantioselectivities. The synthesis of such chiral moieties was achieved only in a diastereoselective fashion, when a stoichiometric amount of a chiral auxiliary was built into the substrate (Hong et al. (2015) *J. Am. Chem. Soc.* 137:11946). In contrast, Ir(Me)-CYP119-Max catalyzed the formation of 8 (FIG. 23) in 90% ee, with no need for the auxiliary. To observe substantial amounts of this product (TON=31), the reaction was conducted at 40° C.; the enantioselectivity of the product at this temperature was the same as that of the small quantity of product formed at room temperature. These data constitute the first enzyme-catalyzed carbene insertion into an unactivated C—H bond and illustrate the value of employing a thermally stable enzyme scaffold.

In addition to catalyzing intramolecular reactions with unactivated C—H bonds, Ir(Me)-CYP 119-Max catalyzes the first enzyme-catalyzed, intermolecular carbene insertion into a C—H bond. Intermolecular insertions of carbenes into C—H bonds are challenging because the metal-carbene intermediate can undergo competitive diazo coupling or insert the carbene unit into the O—H bond of water (Srivastava et al. (2015) *nat. Commun.* 6:7789 and Weldy et al. (2016) *Chem. Sci.* 7:3142). In fact, the model reaction between phthalan (10, FIG. 23) and ethyl diazoacetate (EDA) forms alkene and alcohol as the dominant products when catalyzed by the free Ir(Me)-PIX cofactor; only trace amounts of carbene insertion product 11 (FIG. 23) were formed. In sharp contrast, the same reaction catalyzed by the mutant Ir(Me)-PIX CYP119-Max-A152F occurred to form 11 in 55% yield with 330 TON and 68% ee. Dimerization of the carbene when catalyzed by Ir(Me)-CYP119-Max is limited, presumably because of selective binding and pre-organization of the substrate; the selectivity for formation of the C—H carbene insertion product 11 over the alkene side product 12 (FIG. 23) was 70-fold higher when catalyzed by Ir(Me)-PIX CYP119-Max-A152F than when catalyzed by the free cofactor. This intermolecular, enzyme-catalyzed C—H carbene insertion reaction opens new possibilities for selective C—H functionalizations.

Example 44. Synthetic Scale Reaction with CYP119

Figure 24:
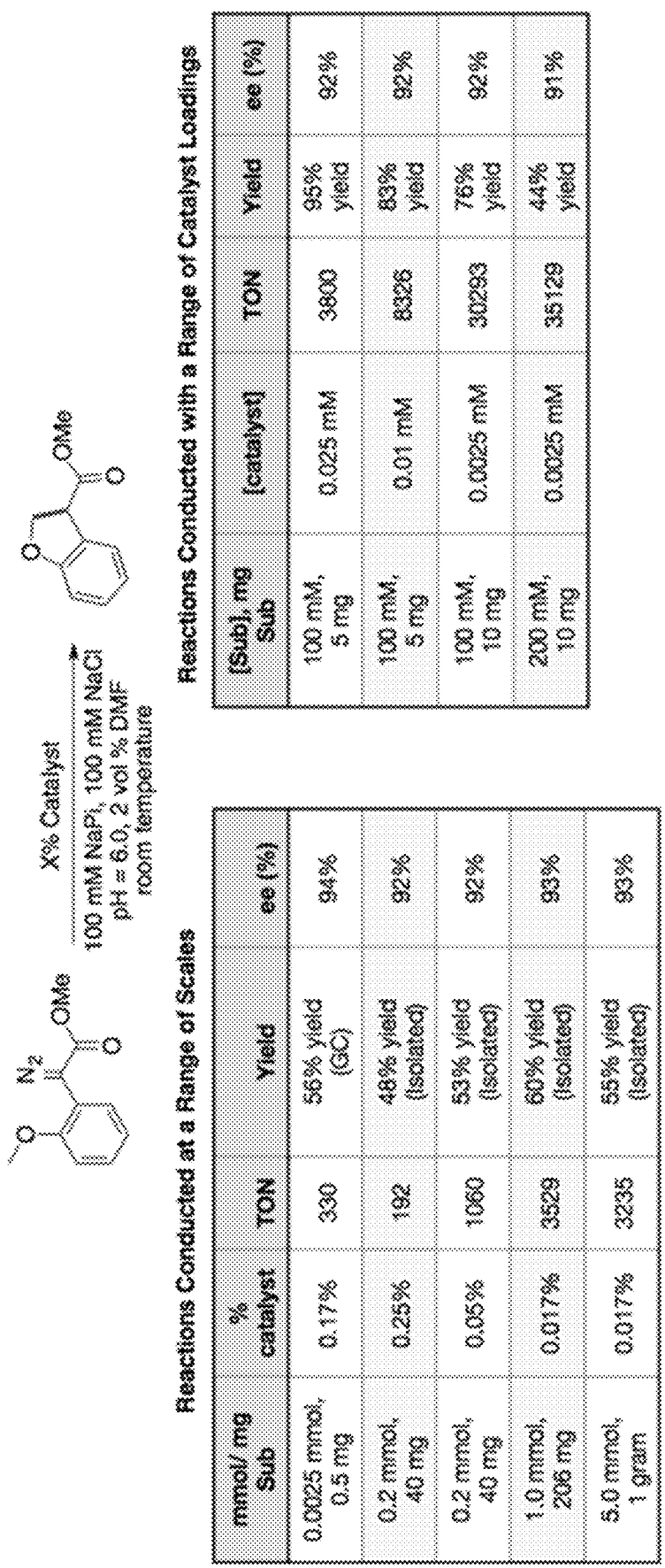
FIG. 24 presents results for catalyst productivity in intramolecular C—H carbene insertion reactions catalyzed by Ir(Me)-PIX CYP119-Max under synthetically relevant reaction conditions.

We found that a series of reactions containing between 40 mg and 1 g of substrate 9 (FIG. 13) catalyzed by Ir(Me)-CYP-Max occurred with yields and enantioselectivities that were similar to each other (91-94% ee), showing that the outcome of the reaction is independent of the scale (FIG. 24). Moreover, with 200 mM of substrate, reactions catalyzed by Ir(Me)-CYP-Max (0.0025 mM) formed product 10 (FIG. 13) with up to 35,000 TON without loss of enantioselectivity (93% ee, FIG. 24). Thus, this artificial metalloenzyme operates with high productivity under conditions suitable for preparative scales. Finally, Ir(Me)-CYP-Max supported on CNBr-activated sepharose catalyzed the conversion of 9 to 10 by carbene insertion into a C—H bond in 52% yield and 83% ee. This supported catalyst was used, recovered, and recycled four times without loss of the enantioselectivity for formation of 10, while retaining 64% of the activity.

Example 45. Catalysis of Chemoselective C—H Amination

Figure 25:
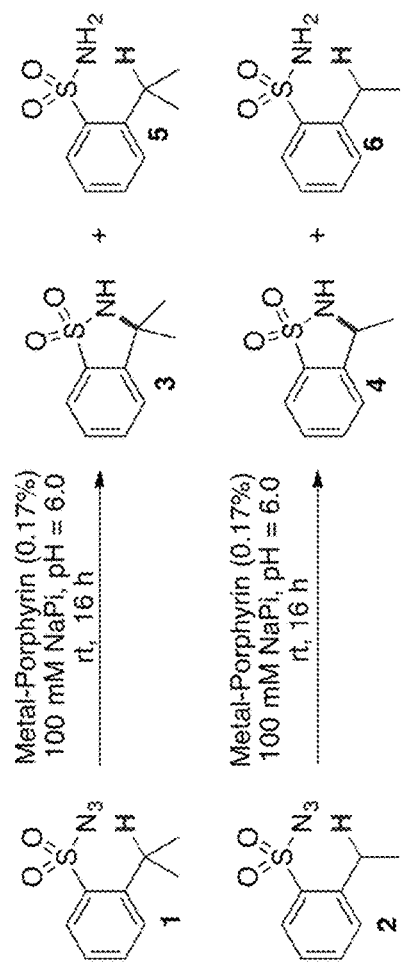
FIG. 25 presents results from an evaluation of [M]-PIX-IX complexes as catalysts for metal catalyzed C—H amination reactions. Top: C—H amination reaction involving the insertion of tertiary and secondary C—H bonds. The targeted products of the C—H insertion reactions are shown in addition to the side products formed from metal-nitrene reduction. Bottom: Outcome of C—H insertion reactions catalyzed by each metal complex. Bars reflect the mol ratio of two products (sultam and sulfonamide) formed, and a comparison of the outcomes in the case of insertions into secondary C—H bonds (dark gray bars) and tertiary C—H bonds (light gray bars). Reactions catalyzed by Cu and Mn porphyrins produced trace sulfonamide product and no observable sultam product.
Figure 25:
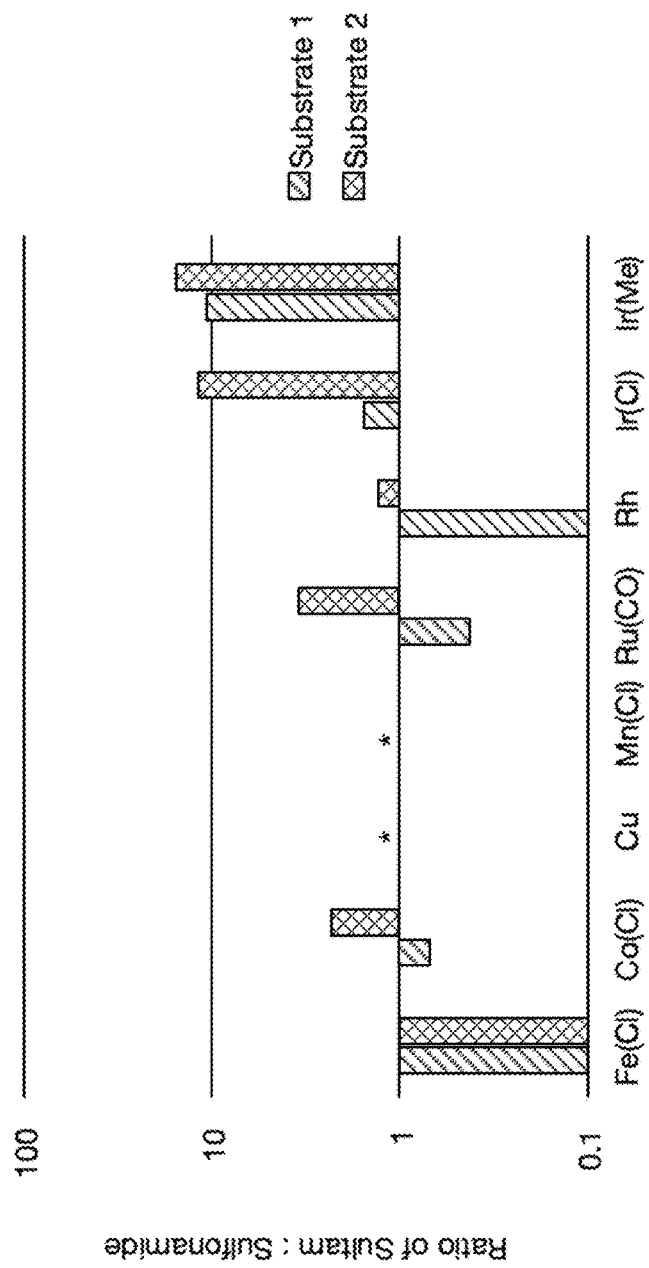

To create an artificial heme enzyme for chemoselective C—H amination, we first assessed the reactivity of a set of free metallo-porphyrins IX (M-PIX) for the model reactions to convert sulfonylazides 1 and 2 into sultams 3 and 4 (FIG. 25). These model substrates require activation of azide to form the metal-nitrene followed by the insertion of the nitrene unit into either tertiary or secondary C—H bonds respectively. The [M]-PIX complexes containing Fe, Cu, and Mn either did not react with the sulfonyl azide or reacted with chemoselectivity strongly favoring the sulfonamide products (5, 6, FIG. 25) over the sultam product. Reactions of sulfonyl azide 1, in the presence of the metal-PIX complexes containing Co, Ru, or Rh formed preferentially the sultam over the sulfonamide product with modest chemoselectivity. However, in reactions of sulfonyl azide 2, containing stronger, secondary C—H bonds, the same catalysts formed predominantly sulfonamide over sultam.

Although porphyrins containing iridium have not been reported for the insertion of nitrenes into C—H bonds (Suematso et al. (2008) *J. Am. Chem. Soc.* 130:10327), Ir(Me)-PIX was found to be the most active and the most chemoselective catalyst from the series of tested M-PIXs for the formation of C—H insertion products under aqueous conditions, producing the sultam over the sulfonamide with >10:1 chemoselectivity for both substrates (FIG. 25). In the presence of Ir(Me)-PIX, substrate 1 (FIG. 25) reacted to form sultam 3 (FIG. 25) in 92% yield, with 14:1 selectivity over the formation of sulfonamide 5 (FIG. 25). Under otherwise identical conditions, substrate 2 (FIG. 25) containing less reactive secondary C—H bonds underwent the reaction to form 4 (FIG. 25) in 72% along with 6% of side-product 6 (FIG. 25). Upon heating the reaction to 37° C., the yield for the reaction of substrate 2 was increased to 89% of sultam 4 and 8% of sulfonamide 6.

Example 46. Creation of Catalyst with Increased C—H Amination Activity and Chemoselectivity In light of the results of Example 45, we sought to create thermally stable Ir-containing P450s, which can be used at elevated temperatures in order to achieve enzymatic C—H amination activity. The apo-form of WT CYP119 was expressed recombinantly in *E. coli* in high yield (10-20 mg/L cell culture) using minimal media without supplementation with any source of iron to limit heme biosynthesis. The apo protein was purified directly using Ni-NTA chromatography, after which the protein was reconstituted by the addition of a stoichiometric addition of Ir(Me)-PIX cofactor, without any need for subsequent purification.

Figure 26:
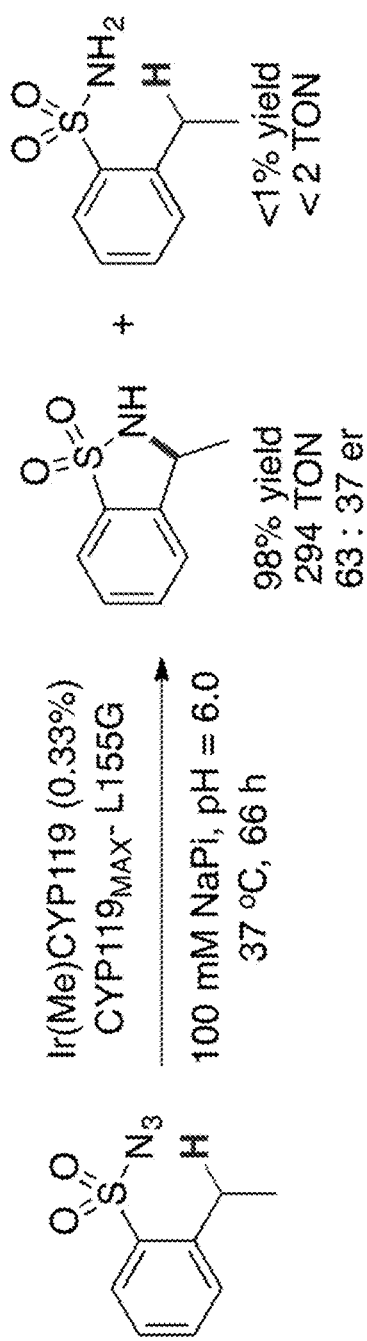
FIG. 26 is a scheme of a C—H amination reaction catalyzed by a variant of Ir(Me)-PIX CYP119 containing the following mutations: C317G, L69V, T213G, V254L, L155G. Selectivity and yield determined by SFC using an internal standard.

To assess initially the activity of Ir(Me)-PIX CYP119 variants to catalyze the insertion of nitrenes into C—H bonds, we evaluated the WT Ir(Me)-PIX enzyme, the variant containing the single mutation C317G to the axial ligand, and the variant CYP119-Max-L155G (discovered previously to be highly active for the insertion of carbenes into C—H bonds) as catalysts for the formation of sultam 4 from sulfonylazide 2 (FIG. 25). From results shown in FIG. 26 it can be seen that while the WT and C317G Ir(Me)-PIX enzymes reacted with low activity, the reaction catalyzed by the variant CYP119-Max-L155G formed the sultam in excellent yield (98% yield, 294 TON) and excellent chemoselectivity (<1% yield of sulfonamide 6, FIG. 25). Thus, by changing only the metal site of a P450 from iron to an iridium-methyl unit, a highly active and chemoselective catalyst for C—H amination is created.

Example 47. Creation of Catalyst with Improved C—H Amination Eneatioselectivity

Given the findings of Example 46, we then evaluated whether the enantioselectivity of this transformation could be improved. In our previous studies of Ir(Me)-PIX enzymes, directed evolution of the enzymes to improve enantioselectivity was successful, but laborious, as each variant of the enzymes was expressed and purified prior to evaluation. Therefore, in our pursuit of enantioselective enzymes for C—H amination, we aimed to develop simultaneously a more efficient strategy for the directed evolution of artificial heme proteins that does not require purification or concentration of the enzyme variants.

Toward these objectives, we created a library of plasmids encoding variants of CYP119 with mutants at eight different positions within the active site. To enable rapid evaluation of Ir(Me)-PIX CYP119s, we overexpressed in E. coli the apo form of the CYP119 variants, after which we added the Ir(Me)PIX cofactor to the cell lysate. The metallated lysates were incubated at 37° C. in the presence of the substrate, and the enantioselectivities of the reactions were determined after extracting the product with organic solvent. By this protocol, we evaluated as catalysts 142 variants of Ir(Me)-PIX CYP119 that contained between 2-4 mutations at the targeted active site positions. Many of the mutants evaluated were inactive; however, the screening identified several variants that did form product 4 (FIG. 27) in an enantioselective fashion. The mutant C317G, T213G, V254L, F310L formed product 4 with 84:16 er, while the mutant C317G, T213A, A152L formed the opposite enantiomer of the product (26:74 er).

Figure 27:
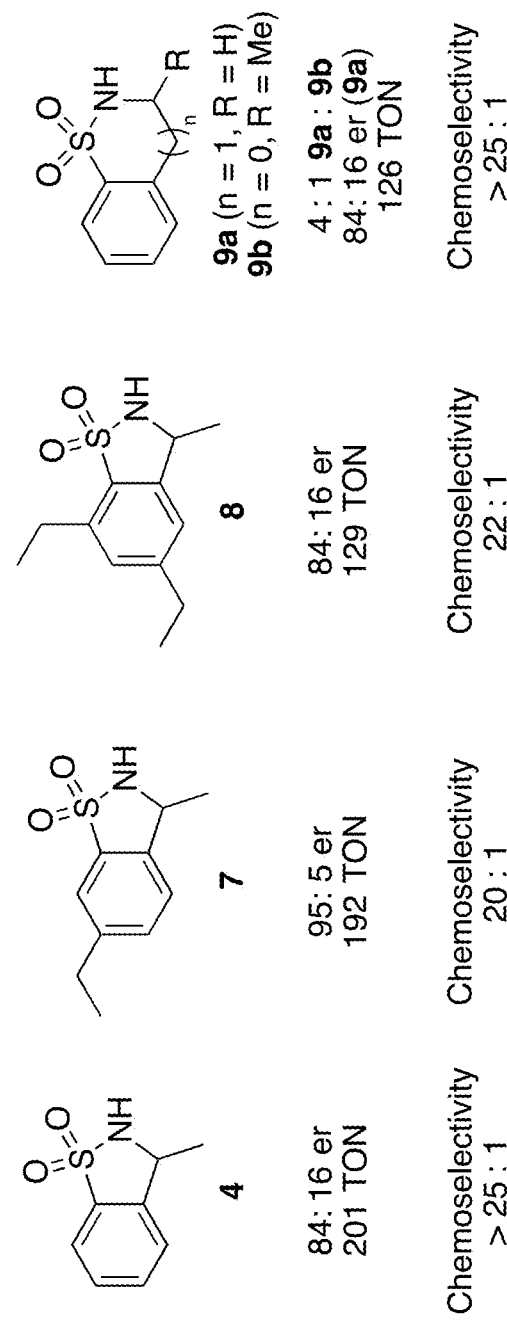
FIG. 27 presents results of C—H insertion reactions of nitrenes using various substrates. Conditions: 0.33% Ir(Me)-PIX CYP119 (mutations C317G, T213G, V254L, F310G), 10 mM substrate, 0.5 mL solvent (100 mM NaPi, 100 mM NaCl, pH=6.0 containing 2 vol % DMF). Reaction time=66 hours. Chemoselectivity refers to mol ratio of sultam formed in comparison to sulfonamide formed. Yield and TON refer to the formation of the sultam product.

A subset of mutants that formed 4 (FIG. 27) with the highest enantiomeric ratios were evaluated subsequently as purified enzymes in the reaction to form 4 and in reactions of similar sulfonyl azides to form products 7-9 (FIG. 27). Results from these experiments shown in FIG. 27 revealed that the mutants identified to be highly selective by screening cell lysates were equally selective in forming 4 when used as purified enzymes. In particular, the mutant C317G, T213G, V254L, F310G functioned as an active and chemoselective catalyst for the formation of 4 and 7-9 in an enantioselective fashion. Under optimized conditions, this mutant catalyzed the formation of various sultams with up to 95:5 er, 200 TON, 67% yield, and >25:1 chemoselectivity. In the case of 2-propyl benzenesulfonylazide, the nitrene can be inserted into either the alpha C—H bonds or beta C—H bonds of the propyl group, forming either a six- or a five-membered ring (9a, 9b, FIG. 27). While the free Ir(Me)-PIX cofactor forms the five-membered product 9b with slight preference over the six-membered 9a (40:60, 9a:9b), the mutant T213G, V254L, F310L catalyzes the reaction with opposite site-selectivity, forming 9b with 4:1 site-selectivity and with 84:16 er, while also producing less than 1% yield of the free sulfonamide byproduct. These results show that directed evolution can lead to catalysts for enantio-, chemo-, and site-selective C—H amination. Moreover, this study also shows that the evaluation of variants of artificially metallated PIX-proteins can be accomplished rapidly using cell lysates, without the need for protein purification or concentration.

Example 48. Catalytic Formation of Aryl Sulfamate

Figure 28:
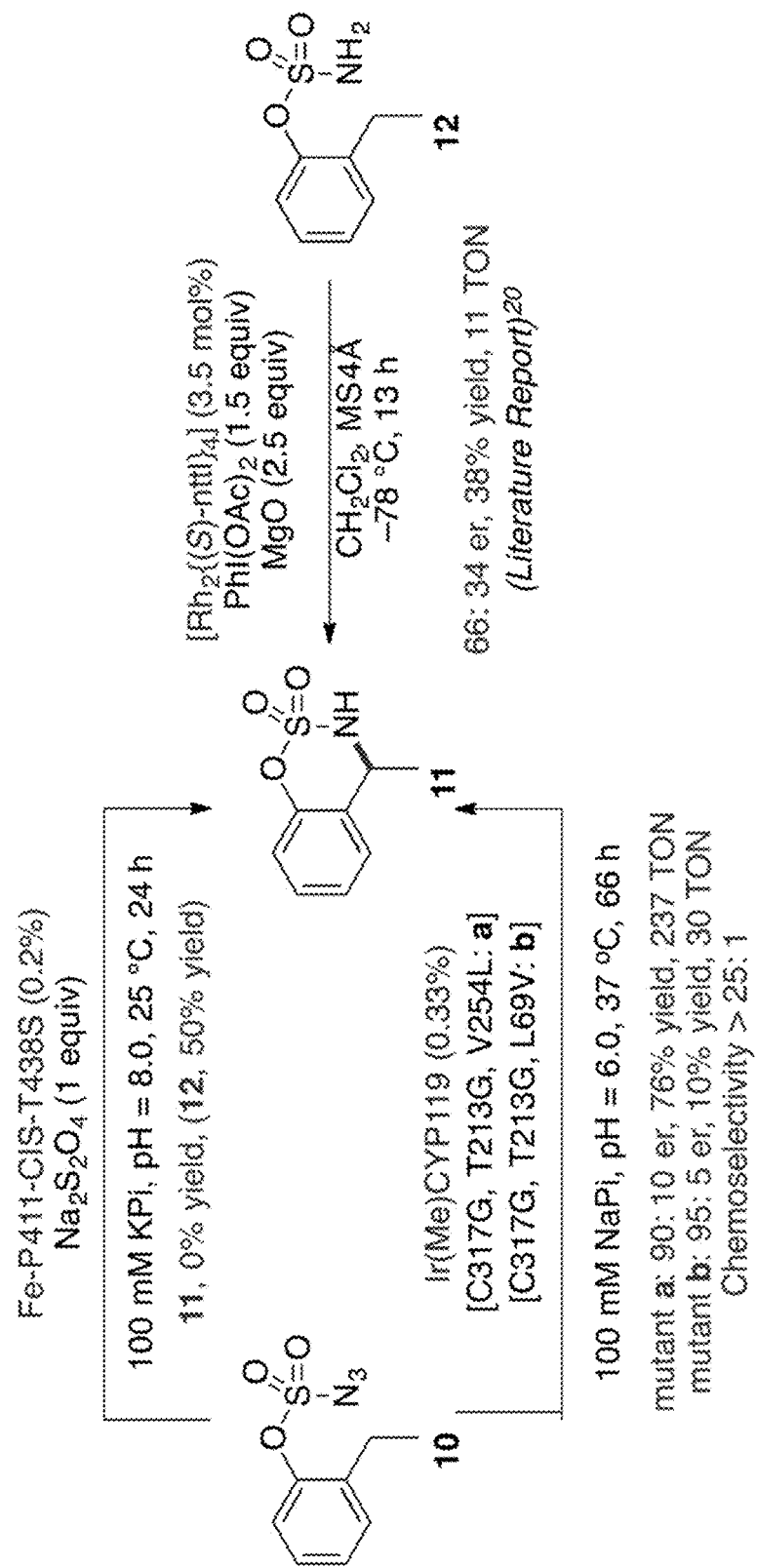
FIG. 28 presents results of a C—H amination approach to aryl sulfamate. The conditions with Ir(Me)CYP119 mutants are same as FIG. 27. The conditions with Fe-P411-CIS mutant: 0.2% Fe-P411-CIS-T438S, 2 mM substrate, 2 mM $N_2S_2O_4$, 1 mL solvent (100 mM KPi, pH 8.0 containing 2.5 vol % DMSO).

To demonstrate further the potential of the Ir(Me)-PIX cofactor to enhance C—H amination reactions catalyzed by enzymes, we evaluated Ir(Me)-PIX CYP119 variants as catalysts in the model reaction to form an aryl sulfamate motif (FIG. 28), which is the versatile intermediate for various chiral benzyl amine compounds by nickel-catalyzed cross-couplings (When and Bois (2005) Org. Lett. 7:4685 and Luo et al. (2012) Angew. Chem. Int. Ed. 51:6762). The C—H amination reaction of 10 (FIG. 28) is not catalyzed effectively by either Fe-P450-BM3 reported previously for C—H amination (McIntosh et al. (2013) Angew. Chem. Int. Ed. 52:9309) or by the Ir(Me)-PIX cofactor (10% yield). Therefore, we sought to identify a variant of Ir(Me)-PIX CYP119 that would catalyze this reaction with rate acceleration compared to the same reaction catalyzed by the free cofactor. Indeed, by evaluating 20 mutants that were active or selective for the reaction of substrate 2 (FIG. 25), we identified the mutant C317G, T213G, V254L that formed 11 (FIG. 28) with 76% yield, 237 TON, 90:10 er, and >25:1 chemoselectivity. We could also obtain 11 with excellent enantioselectivity (95:5 er) with mutant C317G, T213G, L69V, although the yield was low. The previous method with chiral rhodium catalyst for enantioselective C—H amination of aryl sulfonamide to 12 (FIG. 28) gave 11 in low yield with low ee (up to 66:34 er) (Fruit and Muller (2004) Tetrahedron: Asymmetry 15:1019). Therefore, by incorporating the abiological Ir(Me)-PIX cofactor into CYP119, we create catalyst that can form selectively an important class of molecules have not been created previously with any natural enzymes and transition metal catalysts.

Figure 29:
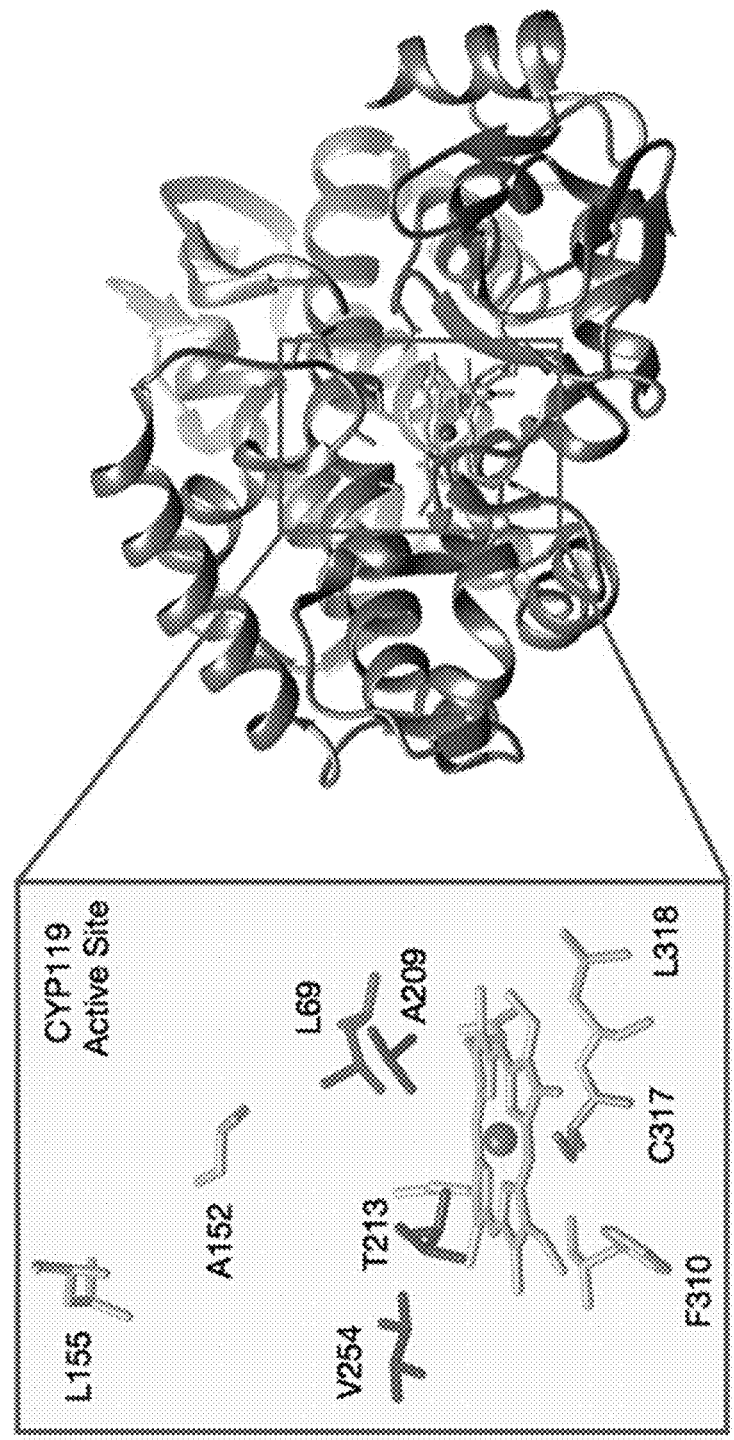
FIG. 29 illustrates the structure of wild type Fe-CYP119 (prepared in Chimera from PDB 1IO7). Left: Structure of Fe-CYP119. Right: Residues targeted in the evolution of the protein scaffold to increase activity and selectivity in C—H bond insertion reactions involving the addition of a carbene unit to an alkene to form a cyclopropane.

Example 49. Evolution of Ir(Me)-PIX P450 Enzymes for the Cyclopropanation of Alkenes Artificial metalloenzymes created from a P450, instead of myoglobin, and Ir(Me)-PIX for cyclopropanation of alkenes were developed by evaluating reactions of ethyl diazoacetate (EDA) with alkene substrates in the presence of Ir(Me)-CYP119 (FIG. 29). Optimized expression of apo CYP119 enzyme production and protein purification for the P450-Ir (Me)-PIX metalloenzymes were performed using multidimensional catalyst array methods as described in Example 35. To identify selective mutants for cyclopropanation, a multi-phase, directed evolution approach was followed.

For the first phase of Ir(Me)-CYP119 directed evolution, double mutants of CYP119 carrying the mutation C317G and one additional mutation (to L, V, A, G, Y, W, F, or T) at one site close to the substrate binding site (V254, T213, A209, and L69) were evaluated as catalysts for the reaction of alkene substrates. Twenty-four mutants were evaluated in Phase 1.

In the second phase of the evolution, a library of triple mutants of CYP119 carrying the mutation C317G and two additional mutations (to L, V, A, G, Y, W, F, or T) at two sites close to the substrate binding site (V254, T213, A209, and L69) was prepared using site directed mutagenesis. Fifty-six mutants were evaluated in Phase 2. From the first two phases of the evolution, the mutants CYP119(+) and (−) were identified as catalysts leading to high, complementary selectivity for most of the substrates, as shown in Table 7. Double mutant "CYP119(+)" refers Ir(Me)-PIX CYP119 with the mutations C317G, V254A and triple mutant "CYP119(−)" refers to Ir(Me)-PIX CYP119 with the mutations C317G, L69F, T213V.

positions that are located more distally from the substrate binding site (A152, L155, F310, L318). In all cases, the native amino acids were changed to L, V, A, G, Y, W, F, or T. Approximately 100 variants of CYP119(+) and CYP119 (−) that contain additional mutations at positions A152, L155, F310, and L318 mutants were evaluated for the cyclopropanation reactions of alkene substrates in Phase 3, the results of which are disclosed in the following Examples.

TABLE 7

| alkene | CYP119(+) | | CYP119(−) | | Free Ir(Me)-PIX | |
|---|---|---|---|---|---|---|
| | ee (%) | dr (cis:trans) | ee (%) | dr (cis:trans) | ee (%) | dr (cis:trans) |
| styrene (17) | 73 | 2:1 | −74 | 5:1 | 0 | 1:4 |
| α-Me-styrene (18) | 82 | 11:1 | −86 | 3:1 | 0 | 1:2 |
| cis-β-Me-styrene (19) | 75 | 27:1* | −18 | 40:1* | 0 | 10:1* |
| trans-β-Me-styrene (20) | 86 | 13:1** | −32 | 4:1** | 0 | 1:>25** |
| hexen-5-one (25) | 79 | 4:1 | −88 | 8:1 | 0 | 1:4 |
| cyclopentene (27) | — | 2:1:t:t*** | — | 228:1:t:1*** | — | 3:1:1:3*** |
| 1-octene (29) | 66 | 4:1 | −78 | 6:1 | 0 | 1:4 |
| cis-2-octene (31) | 39 | 8:1** | −60 | 1:1** | 0 | 5:1** |

*Major diastereomer is 2-c, 3-c:2-t, 3-t, Ref = COOEt, c = cis, t = trans;
**Major diastereomer is 2-c, 3-c:2-t, 3-t, Ref = COOEt, c = cis, t = trans;
***minor products not determined, major product shown as compound 28, t = trace The tabulated data in Table 7 above describes the outcome for cyclopropanation reactions of alkenes having differing steric and electronic properties with EDA using the two mutants of CYP119 identified in the first two phases of directed evolution in comparison to the same reactions catalyzed by the free Ir(Me)-PIX cofactor. The initial evaluation of approximately 100 variants of Ir(Me)-CYP119 containing mutations at positions within the active site (positions L69, A209, T213, V254, FIG. 29) identified the CYP119(+) and CYP119(−) mutants that form opposite enantiomers of the cyclopropane products from reactions of olefins 17-20 and EDA with up to 40:1 dr and up to 86% ee (dr as defined in FIG. 30, FIG. 31, and FIG. 32). For reactions of substrates 17-18 and 20, enzymes were identified that form the opposite diastereomer of the product than is formed from reactions catalyzed by the free Ir(Me)-PIX cofactor (Table 7). Specifically, the double mutant CYP119 (+) formed the (1S,2R)-enantiomer of the cis cyclopropane 21 with 73% ee, while the second variant, the triple mutant CYP119(−) gave the opposite enantiomer (1R,2S) of the cis product 21 with (−)74% ee. In all cases, the analogous reactions of substrates 18-20 catalyzed by the mutant CYP119(+) formed the diastereomer of the cyclopropane products 22-24 containing the ester and the phenyl ring in a cis relationship to one another with >2:1 dr and 73-86% ee. The mutant CYP119(−) gave the opposite enantiomer of the same cyclopropane diastereomer in >3:1 dr and up to (−)86% ee (Table 7). The free cofactor formed the racemic trans isomer as the major cyclopropane product in all cases.

Figure 30:
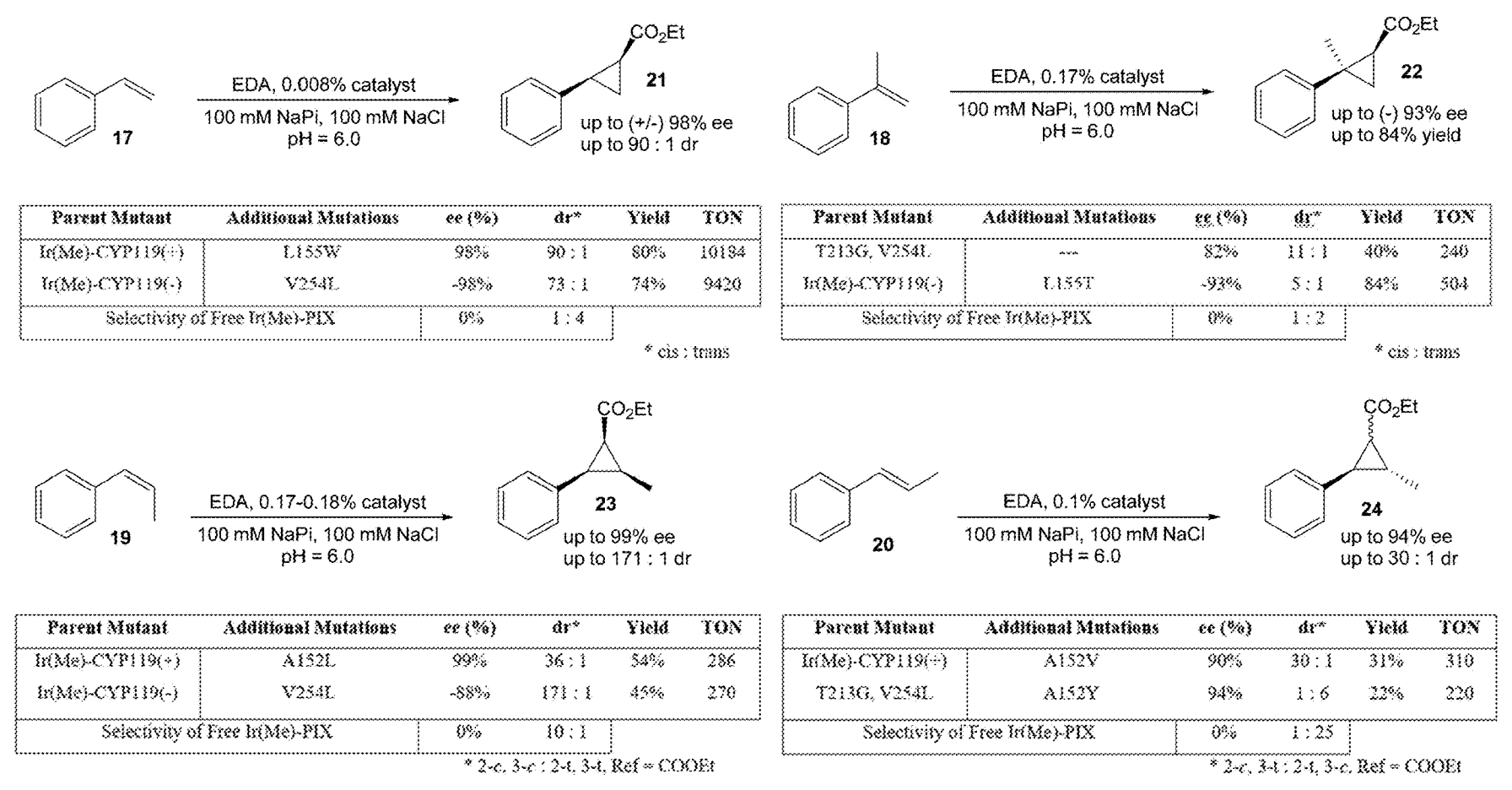

The results from the initial two phases of the directed evolution approach suggested that stereodivergent catalysts for the formation of cyclopropanes from diverse alkenes with high diastereoselectivity and enantioselectivity could be generated by further evolving the two mutants CYP119 (+) and CYP119(−) in the next phase. As such, in the third phase of the evolution, a library of additional mutants was created from CYP119(+) and (−). These mutants contained one or two additional mutations at either the original positions that were targeted (V254, T213, A209, and L69) or at Example 50. Cyclopropanation of Vinylarenes Distinct variants of Ir(Me)-CYP119, which were selected from the final library of mutants, catalyzed the cyclopropanation of the four vinylarenes 17-20 with high enantioselectivity and diastereoselectivity (FIG. 30). Specifically, cyclopropanation of styrene 17 with EDA in the presence of the mutant CYP119(+)-L155W formed the (1S,2R)-enantiomer of the cis cyclopropane 21 in (+)98% ee, 90:1 dr, and 80% yield (10,000 TON). The same reaction in the presence of CYP119(−)-V254L gave the opposite (1R,2S)-enantiomer of 21 with (−)98% ee, 73:1 dr, and similar yield (74%). The diastereoselectivity for the cis products formed by variants of Ir(Me)-PIX CYP119 was over 6-fold higher than that by evolved Fe-PIX enzymes (Fe-P450 CIS-T438S, reported previously by Arnold et al., catalyzes the same transformation producing the same stereoisomer of the product with 11.5:1 dr), and variants of Ir(Me)-PIX CYP119 were identified that provide either enantiomer of the cis-cyclopropane product with high enantioselectivity. The cyclopropanation of 18 with EDA in the presence of variant C317G, T213G, V254L afforded the (1S,2S) enantiomer of product 22 in (+)82% ee, 11:1 dr, and 40% yield (240 TON), while the (1R, 2R)-enantiomer of 22 was formed in 84% yield with 504 TON, $(-)_{93}$% ee, 5:1 dr using the mutant CYP119(−)-L155T in −93% ee (FIG. 30). Because the solubility of EDA is than that of the alkene in water and because EDA competitively couples with itself to form alkene, EDA was added by syringe pump. This procedure, commonly applied for the reactions of highly active iridium catalysts, leads to higher yields than does the procedure with batch addition of EDA (Anding et al. (2012) *Organometallics* 31:3628; Davies et al. (2009) *Chem. Soc. Rev.* 38:3061).

The cis- and trans-isomers of f-methylstyrene (19 and 20) do not react with Fe-PIX proteins or artificial metalloenzymes reported previously, but they underwent highly selective cyclopropanation reactions in the presence of variants of Ir(Me)-CYP119(+) and (−), as shown in FIG. 30. In the presence of the mutant CYP119(+)-A152L, cis-alkene 19 reacted with EDA to form the all-cis diastereomer of the cyclopropane product 23 with 286 TON, 99% ee, and 36:1 dr (2-c,3-c: 2-t,3-t, ref=CO₂Et, c=cis, t=trans). The mutant CYP119(−) afforded the opposite enantiomer of the cyclopropane 23 with 270 TON, >100:1 dr (2-c,3-c: 2-t,3-t, ref=CO₂Et) and (−)₈₈% ee. trans-alkene 20 reacted with EDA in the presence of the mutant CYP119(+)-A152V, to form the 2-c,3-t-cyclopropane 24 with 310 TON, 30:1 dr (2-c,3-t: 2-t,3-c, ref=CO₂Et), and 90% ee. Mutants that form the opposite diastereomers of the cyclopropane formed from trans-1-methylstyrene 20 were also identified. The reaction of trans alkene 20 and EDA in the presence of the variant C317G, T213G, V254L, A152Y afforded the cyclopropane with a trans relationship between the ester and the phenyl group with 220 TON, 94% ee, and 6:1 dr (2-t,3-c: 2-c,3-t, ref=CO₂Et) (FIG. 30).

Example 51. Cyclopropanation of Unactivated Alkenes

Figure 31:
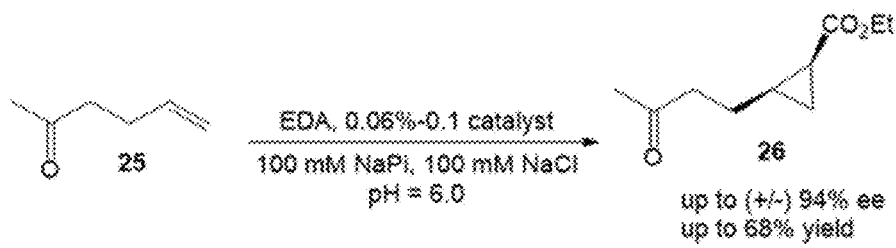
FIG. 31 presents results of cyclopropanation of aliphatic alkenes using Ir(Me)-CYP119 mutants. The reactions were conducted on 1 mL scale under the listed conditions using 20 mM substrate (25 or 27) and 3 equiv. of EDA (added over 3 hours by syringe pump as a 30% (v:v) solution in DMF). The yields were determined by GC using dodecane as internal standard. The stereochemistry of products was assigned based on NMR analysis; absolute stereochemistry of 26 was not assigned.
Figure 31:
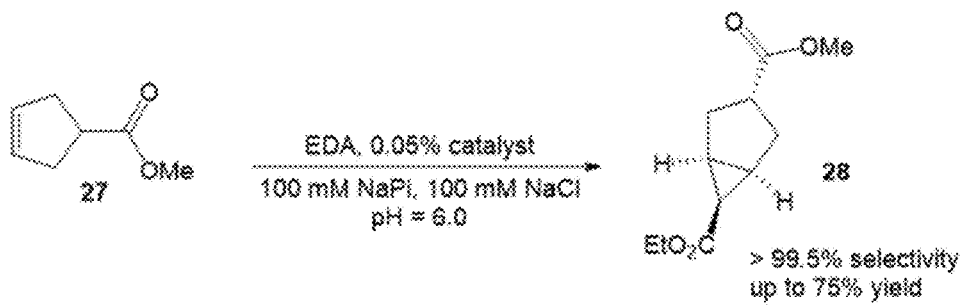

Having identified selective Ir(Me)-PIX CYP119 variants for cyclopropanation reactions, these artificial enzymes were then evaluated as catalysts for the cyclopropanation of unactivated alkenes. This class of alkene has not been reported to react in the presence of Fe-PIX enzymes. The mutants CYP119(+) and CYP119(−) catalyzed the reaction of hexen-2-one 25 and EDA to form opposite enantiomers of cis-cyclopropanes (Table 7). Highly selective variants of the enzymes were identified from the pool of mutants that catalyzed the reactions of substrates 17-20 with the highest enantioselectivities (FIG. 31). No further mutagenesis was needed to achieve high diastereoselectivity and enantioselectivity. In the presence of CYP119(−)-V254L-L155T, the terminal alkene 25 underwent cyclopropanation with EDA to form the cis-cyclopropane 26 in (−)99% ee, 7:1 dr (cis: trans), and 68% yield with 1006 TON. The variant CYP119 (+)-L155W formed the opposite enantiomer of the cis-cyclopropane (44% yield, 440 TON, 99% ee, 19:1 dr). The related substrate 1-octene 29 was also functionalized with high enantio- and diastereoselectivity to form cyclopropane 30 (FIG. 32), although the yield of this reaction was limited by the poor water solubility of 1-octene.

Figure 32:
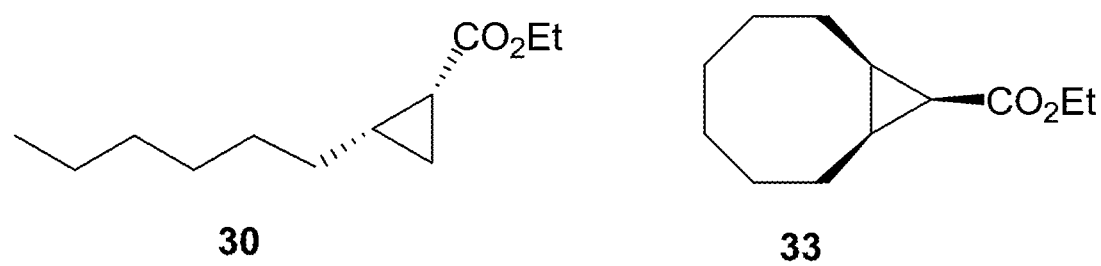
FIG. 32 presents results of cyclopropanation of additional aliphatic alkenes using Ir(Me)-CYP119 mutants. The reactions were conducted on 1 mL scale using 20 mM substrate and 3 equiv. of EDA (added over 3 hours by syringe). Product 30 was obtained using the variant CYP119-C317G, A209G (0.02 mol % cat). Product 33 was obtained using the variant CYP119(+)-F69L, L318F, L155W (0.2 mol % cat). Product 32 was obtained using the variant CYP119(−)-V254L (0.1 mol % cat), and product 34 was obtained using the variant CYP119(+)-L155W (0.2 mol % cat). The TON were determined by GC using dodecane as internal standard. The stereochemistry of products was assigned based on NMR analysis.
Figure 32:
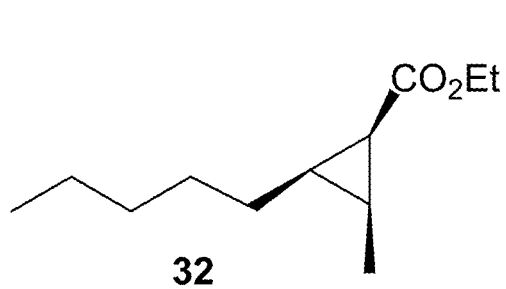
Figure 32:
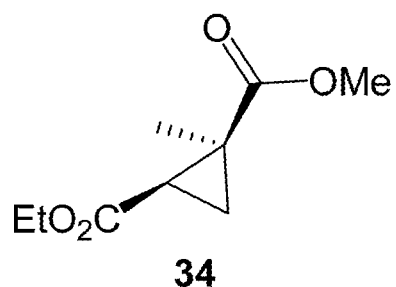

Internal, unactivated, aliphatic alkenes also underwent highly stereoselective cyclopropanation in the presence of the derivatives of Ir(Me)-PIX CYP119(+) and (−). The reaction of cyclopentene 27 and EDA formed cyclopropane 28 in 76% yield with 1300 TON in the presence of CYP119 (−)-F310W(FIG. 31). The stereoisomer 28 was formed with >99.5% diastereomeric excess. This diastereoselectivity contrasts sharply with that of the reaction in the presence of the free Ir(Me)-PIX cofactor. The free cofactor formed a mixture of four diastereomers, none of which accounted for >45% of the product. The related substrate cyclooctene (33a) reacts with EDA in the presence of the mutant T213G, V254L, L318F, L155W to form the cis-cyclopropane 33 with 14:1 dr and 36 TON (FIG. 32). Like the yield of the reaction of 1-octene 29, the yield of this reaction was limited by the poor water solubility of the alkene.

The acyclic, internal alkene cis-2-octene 31 also underwent stereoselective cyclopropanation with EDA. This reaction formed cyclopropane 32 in up to 94% ee, 108:1 dr, and with 94 TON in the presence of Ir(Me)-CYP119(−)-V254L (FIG. 32). No comparable stereoselectivities have been achieved using a small molecule catalyst for the cyclopropanation of acyclic, internal, aliphatic alkenes (Deng et al. (2012) *Angew. Chem., Int. Ed.* 51:11620). Electron poor, unactivated, 1,1-disubstituted alkenes also underwent stereoselective cyclopropanation in the presence of Ir(Me)-CYP119 enzymes, but with modest yields and turnover numbers (FIG. 32). The variant CYP119(+)-L155W catalyzed the reaction of ethyl methacrylate and EDA to form the product 34 in 80% ee and 8:1 dr (cis: trans) with 47 TON. The variant CYP119(−)-L155V afforded the opposite enantiomer of 34 with 88% ee, 1:1 dr and 145 TON.

Example 52. Cyclopropanation of Terpenes

Figure 33:
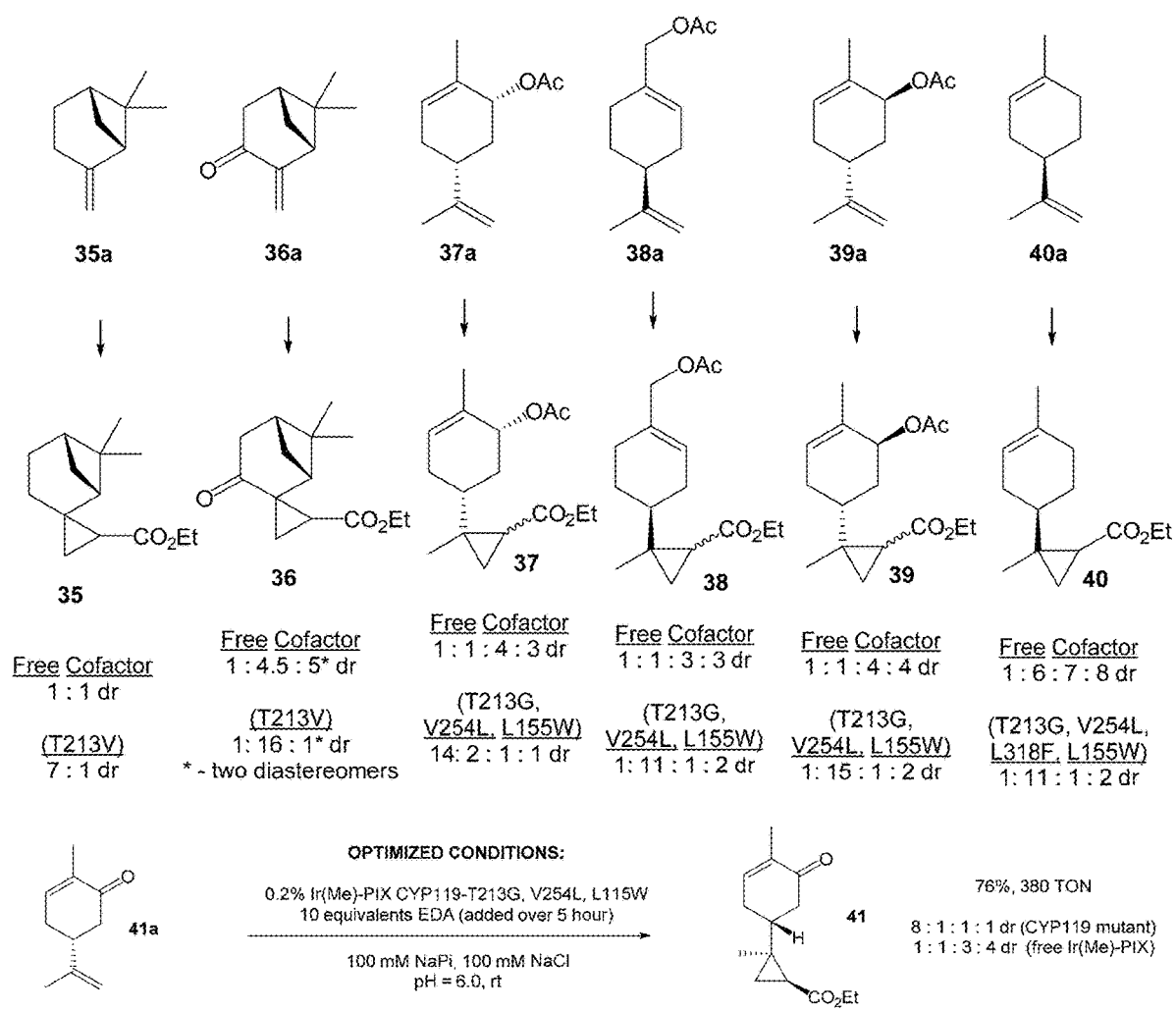
FIG. 33 presents results of cyclopropanation reactions of natural terpenes and their derivatives. Above: selectivities obtained from free Ir(Me)-PIX cofactor and Ir(Me)-PIX CYP119 variants designed by directed evolution. Products 35-40 were obtained under the following reaction conditions: 0.2% cat., 10-17 mM substrate 35a-40a (5 μL in DMF), 6-10 equiv. EDA (5 μL in DMF, slow addition over 5 h), 1 mL buffer solution (100 mM *NaPi*, 100 mM NaCl, pH 6.0). Below: The reaction of (−)-carvone 41a with EDA under conditions optimized to produce product 41 in the highest yield and diastereoselectivity. The yields were determined by GC using dodecane as internal standard. EDA was added slowly using a syringe pump.

The reactivity of the artificial P450 enzymes described above was then tested for cyclopropanation of unactivated aliphatic alkenes commonly found in natural products, such as terpenes (FIG. 33). The selective cyclopropanation of this class of molecules represents a challenging synthetic problem because of possibility to form multiple diastereomeric products (Friedrich et al. (1991) *J. Org. Chem.* 56:2202). An enzyme catalyst provides the potential to recognize the overall structure of the substrate, rather than the local orientation of substituents at the alkene or relative local size of substituents at the alkene.

The evaluation of the cyclopropanation reactions of seven terpenes (35a-41a)catalyzed by a library of mutants of Ir(Me)-PIX CYP119 revealed that specific variants of the enzyme catalyze the reactions with control over diastereoselectivity (FIG. 33 and Table 8). For example, the reaction of P-pinene (35a) and EDA in the presence of the free Ir(Me)-PIX cofactor occurred to form an equimolar mixture of diastereomers (35), whereas the same reaction in the presence of Ir(Me)CYP119-T213V formed predominantly one isomer of the product, with 7:1 dr. In the presence of the same variant of the enzyme, (+)-pinocarvone (36a), a close derivative of Pf-pinene, underwent reaction with EDA to form one major isomer of the product 36, which is 89% of the stereoisomers formed, while the same reactions catalyzed by the free cofactor formed this isomer as only 43% of the cyclopropane product (FIG. 33).

TABLE 8

| Substrate | Equiv. of EDA | Mutant | Yield* | TON | Selectivity* |
|---|---|---|---|---|---|
| 35a | 6 | T213V | 9% | 46 | 6.6:1** |
| 33a | 6 | T213G, V254L, L318F, L155W | 7% | 35 | 14:1*** |
| 41a | 10 | T213G, V254L, L155W | 76% | 380 | 8:1:1:1 |

Reaction Conditions: 10 mM substrate, EDA (5 μL in DMF, slow addition over 5 h), 1 mL buffer solution (100 mM NaPi, 100 mM NaCl, pH 6.0);
*The yields of major products were measured by GC with dodecane as internal standard and diastereoselectivity analyzed by GC;
**Only two major products observed;
***cis/trans Cyclopropanations of the other five terpenes catalyzed by variants of Ir(Me)CYP119 also occurred with diastereoselectivities that were distinct from those of reactions of the free cofactor. The major diastereomers from the reactions catalyzed by the enzymes were different from those of the reactions catalyzed by the free cofactor, and the reactions catalyzed by the enzymes occurred with higher diastereoselectivities. In the presence of the mutant T213G, V254L, L155W, cyclopropanes 37-39 were formed with the major diastereomer being 73-790 of the stereoisomers formed, while the same reactions catalyzed by the free Ir(Me)-cofactor produced the same diastereomers as only 9-12% of the cyclopropanation products. Similarly, in the presence of the same mutant of the enzyme, the cyclopropanation of (−)-carvone (41a) occurred to form a product mixture of 41 consisting of 730 of a major diastereomer, which was a minor diastereomer (11%) formed in the presence of the free cofactor. The reaction of (+)-limonene (40a) with EDA, producing 40, occurred with higher stereoselectivity when catalyzed by a Ir(Me)CYP119 variant containing the additional mutation L318F (FIG. 33).

After identifying a selective enzyme for each substrate, we conducted studies to determine if modification of the reaction parameters would result in an improvement in the yield of reactions of this class of substrate. Using the reaction of carvone with EDA as a representative example, it was determined that the reaction of carvone 41a with 10 equivalents of EDA delivered the cyclopropane products in 76% yield, with 380 TON, and 8:1:1:1 diastereoselectivity. The (1S,2R)-isomer 41 was the major product (FIG. 33). The Ir(Me)-PIX enzyme was also suitable for preparative reactions: the reaction of 1 mmol of carvone gave product 38 in 52% isolated yield with 1400 TON and with diastereoselectivity that was comparable to that observed for the reaction on an analytical scale.

To determine the relative propensity of these artificial enzymes and more conventional chiral rhodium catalysts to catalyze stereoselective cyclopropanations, reactions were conducted for carvone with dirhodium complexes that are well established to catalyze enantioselective cyclopropanations of certain alkenes (Davies et al. (2009) *Chem. Soc. Rev.* 38:3061; Denton et al. (2009) *Org. Lett.* 11:787; Chepiga et al. (2013) *Tetrahedron* 69:5765; Wang et al. (2013) *Chemical Science* 4:2844; Chanthamath et al. (2016) *Acc. Chem. Res.* 49:2080; Doyle et al. (1994) *Tetrahedron* 50:1665). In contrast to the high selectivity for the reaction of carvone catalyzed by the artificial metalloenzyme, the reactions catalyzed by $Rh_2(OAc)_4$, $Rh_2(5R\text{-}MEPY)_4$, and $Rh_2(4S\text{-}MEOX)_4$ occurred with low diastereoselectivity (Table 9). The cyclopropanation of carvone catalyzed by these complexes formed the four diastereomers in 1:1:2:1, 1:2:2:3, and 3:1:3:1 ratios, respectively (Table 9).

TABLE 9

| Entry | Catalyst | Cat. Loading (mol %) | Substrate (41a) (mmol) | EDA (mmol) | Solvent volume | Slow addition time (h) | dr | GC yield (isolated yield) |
|---|---|---|---|---|---|---|---|---|
| 1 | $Rh_2(OAc)_4$ | 0.2 | 5 | 5 | 11 mL DCM | 5 | — | (60%) |
| 2 | $Rh_2(OAc)_4$ | 0.5 | 10 | 2 | 15 mL DCM | 5 | 1:1.1:1.7:1.1 | 50% |
| 3 | $Rh_2(5R\text{-}MEPY)_4$ | 0.5 | 10 | 2 | 9 mL DCM | 5 | 1:2:1.7:3.4 | 13% |
| 4 | $Rh_2(4S\text{-}MEOX)_4$ | 0.5 | 10 | 2 | 9 mL DCM | 5 | 2.6:1:3.4:1.2 | 24% |
| 5 | T213G, V254L, L155W | 0.2 | 0.01 | 0.1 | 1 mL NaPi | 2 | 80% dr (major product) | 76% |
| 6 | T213G, V254L, L155W | 0.037 | 1 | 10 (+750 μL DMF) | 66 mL NaPi | 2 | 79% dr (major product) | (52%) |

Example 53. Substrate-Selective Cyclopropanation

Figure 34:
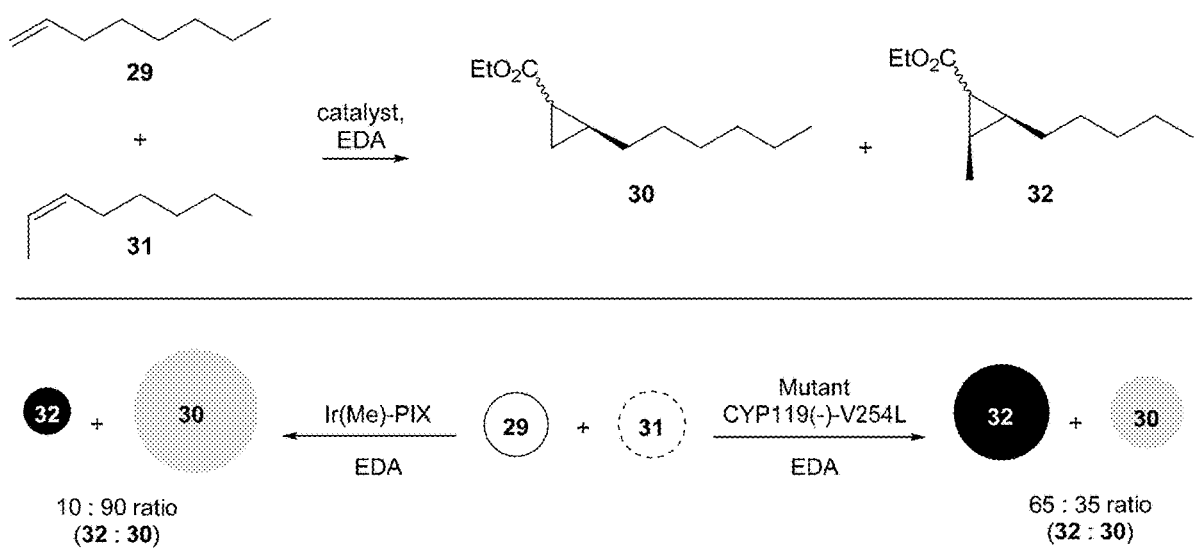
FIG. 34 presents results of substrate-selective cyclopropanation reactions of an alkene mixture. catalyzed by a variant of CYP119 in comparison to the same reaction catalyzed by the free cofactor. Above: general reaction scheme for the substrate mixture of 29 and 31. Below: substrate-selective cyclopropanation of mixed substrates 29 and 31 catalyzed by a variant of CYP119 in comparison to the same reaction catalyzed by the free cofactor. Reaction conditions: 10 mM 29, 10 mM 31, 60 mM EDA (added by syringe pump over 1 hr), 0.17% catalyst, 100 mM NaPi/100 mM NaCl, pH 6.0, 3 vol. % DMF. The amounts of 30 and 32 are the sum of all stereoisomers of the product. In the case of the enzyme catalyzed reaction, 30 and 32 were produced in comparable stereoselectivities to those of reactions of the individual substrates.

Selective binding of one substrate in the presence of a mixture allows natural enzymes to react with substrates that are typically less reactive in the presence of those that are typically more reactive (Johnston et al. (2011) *Arch. Biochem. Biophys.* 507:86; Whitehouse et al. (2012) *Chem. Soc. Rev.* 41:1218). For example, the size of alkenes 29 and 31 are similar, but the position of the double bond is different. Hence, the reactivity of these two alkenes is different and the terminal alkene is more reactive toward most catalysts (Maxwell et al. (1992) *Organometallics* 11:645). The reaction of a mixture of 29 and 31 in the presence of the free Ir(Me)-PIX occurred preferentially with 1-octene 29 over 2-octene 31 to form cyclopropane 30 as 92% of the total product mixture (FIG. 34). In sharp contrast, the reaction of EDA with a mixture of 29 and 31 catalyzed by Ir(Me)-CYP119(−)-V254L occurred predominantly with 31, producing a 65:35 ratio of 32 to 30 (FIG. 34).

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

Table of Illustrative Sequences:

SEQ ID NO: 1 CYP119 *Sufolobus sofataricus*
MYDWFSEMRKKDPVYYDGNIWQVFSYRYTKEVLNNFSKFSSDLTGYHERLEDLRNGKI
RFDIPTRYTMLTSDPPLHDELRSMSADIFSPQKLQTLETFIRETTRSLLDSIDPREDDIVKK
LAVPLPIIVISKILGLPIEDKEKFKEWSDLVAFRLGKPGEIFELGKKYLELIGYVKDHLNSG
TEVVSRVVNSNLSDIEKLGYIILLLIAGNETTTNLISNSVIDFTRFNLWQRIREENLYLKAIE
EALRYSPPVMRTVRKTKERVKLGDQTIEEGEYVRVWIASANRDEEVFHDGEKFIPDRNP
NPHLSFGSGIHLCLGAPLARLEARIAIEEFSKRFRHIEILDTEKVPNEVLNGYKRLVVRLK
SNE SEQ ID NO: 2 sperm whale myoglobin sequence
VLSEGEWQLVLHVWAKVEADVAGHGQDILIRLFKSHPETLEKFDRFKHLKTEAEMKAS
EDLKKHGVTVLTALGAILKKKGHHEAELKPLAQSHATKHKIPIKYLEFISEAIIHVLHSRH
PGDFGADAQGAMNKALELFRKDIAAKYKEL SEQ ID NO: 3 CYP 119 *Sufolobus sofataricus* HxHis-CYP 119.
The CYP119 region of the sequence is underlined
TEVGDIHMKSSHHHHH<u>ENLYFQSNAMYDWFSEMRKKDPVYYDGNIWQVFSYRYTKE
VLNNFSKFSSDLTGYHERLEDLRNGKIRFDIPTRYTMLTSDPPLHDELRSMSADIFSPQKL
QTLETFIRETTRSLLDSIDPREDDIVKKLAVPLPIIVISKILGLPIEDKEKFKEWSDLVAFRL
GKPGEIFELGKKYLELIGYVKDHLNSGTEVVSRVVNSNLSDIEKLGYIILLLIAGNETTTN
LISNSVIDFTRFNLWQRIREENLYLKAIEEALRYSPPVMRTVRKTKERVKLGDQTIEEGEY
VRVWIASANRDEEVFHDGEKFIPDRNPNPHLSFGSGIHLCLGAPLARLEARIAIEEFSKRF
RHIEILDTEKVPNEVLNGYKRLVVRLKSNE</u>

SEQ ID NO: 4 P450 BM3 (*Bacillus megaterium*) The His tag is underlined.
TIKEMPQPKTFGELKNLPLLNTDKPVQALMKIADELGEIFKFEAPGRVTRYLSSQRLIKEA
CDESRFDKNLSQALKFARDFAGDGLVTSWTHEKNWKKAHNILLPSFSQQAMKGYHAM
MVDIAVQLVQKWERLNADEHIEVSEDMTRLTLDTIGLCGFNYRFNSPYRDQPHPFIISM
VRALDEVMNKLQRANPDDPAYDENKRQFQEDIKVMNDLVDKIIADRKARGEQSDDLLT
QMLNGKDPETGEPLDDGNIRYQIITFLIAGHEATSGLLSFALYFLVKNPHVLQKVAEEAA
RVLVDPVPSYKQVKQLKYVGMVLNEALRLWPTAPAFSLYAKEDTVLGGEYPLEKGDE
VMVLIPQLHRDKTVWGDDVEEFRPERFENPSAIPQHAFKPFGNGQRASIGQQFALHEAT
LVLGMMLKHFDFEDHTNYELDIKETLTLKPKGFVVKAKSKKIPLGGIPSPST<u>HHHHHH</u>

SEQ ID NO: 5 P450 CAM *Psudeomonas putida* (P45-CAM-6xHis)
The His tag is underlined.
MTTETIQSNANLAPLPPHVPEHLVFDFDMYNPSNLSAGVQEAWAVLQESNVPDLVWTR
CNGGHWIATRGQLIREAYEDYRHFSSECPFIPREAGEAYDFIPTSMDPPEQRQFRALANQ
VVGMPVVDKLENRIQELACSLIESLRPQGQCNFTEDYAEPFPIRIFMLLAGLPEEDIPHLK
YLTDQMTRPDGSMTFAEAKEALYDYLIPIIEQRRQKPGTDAISIVANGQVNGRPITSDEA
KRMCGLLLVGGLDTVVNFLSFSMEFLAKSPEHRQELIQRPERIPAACEELLRRFSLVADG
RILTSDYEFHGVQLKKGDQILLPQMLSGLDERENACPMHVDFSRQKVSHTTFGHGSHLC
LGQHLARRIIVTLKEWLTRIPDFSIAPGAQIQHKSGIVSGVQALPLVWDPATTKAV<u>HHHH
HH</u>

SEQ ID NO: 6 TEV-cleavable N-terminal His6-mOCR myoglobin.
The myoglobin region is underlined.
EGDIHMKSSHHHHHHENLYFQSNMSNMTYNNVFDHAYEMLKENIRYDDIRDTDDLHD
AIHMAADNAVPHYYADIRSVMASEGIDLEFEDSGLMPDTKDDIRILQARIYEQLTIDLWE
DAEDLLNEYLEEVEEYEEDEEGTGSETPGTSESG<u>VLSEGEWQLVLHVWAKVEADVAGH
GQDILIRLFKSHPETLEKFDRFKHLKTEAEMKASEDLKKHGVTVLTALGAILKKKGHHE
AELKPLAQSHATKHKIPIKYLEFISEAIIHVLHSRHPGDFGADAQGAMNKALELFRKDIA
AKYKELGYQG</u>

---

What is claimed is:

1. A catalyst composition comprising:
   a porphyrin;
   M(L), wherein the porphyrin and M(L) form a complex;
   M is a metal, wherein the metal is Ir;
   L is a ligand selected from the group consisting of alkyl, haloalkyl, halogen, CO, and CN; and
   a heme apoprotein, wherein the porphyrin-M(L) complex is bound to the heme apoprotein, wherein the heme apoprotein comprises at least one mutation, wherein the at least one mutation is close to an active site of the heme apoprotein,
   wherein the heme apoprotein is a cytochrome P450 or a myoglobin, and
   wherein the cytochrome P450 has at least 70% sequence identity to the P450 region of SEQ ID NO:3 and comprises a substitution of C317G/A and a second substitution selected from the group of substitutions consisting of T213G/V/A, L69V/Y/W/F, V254L/A/V/G, A209G, A152F/W/Y/L/V, L155T/W/F/V/L, F310G/A/L, and L318G/A/F, as determined with reference to SEQ ID NO:1, wherein when the cytochrome P450 comprises the substitution T213A, the cytochrome P450 additionally comprises a third substitution selected from said group of substitutions.

2. The catalyst composition of claim 1, wherein the ligand L is selected from the group consisting of methyl, ethyl, F, Cl and Br.

3. The catalyst composition of claim 1, wherein M(L) is Ir(Me).

4. The catalyst composition of claim 1, wherein the porphyrin-M(L) complex is a porphyrin-Ir(L) complex comprising the formula:

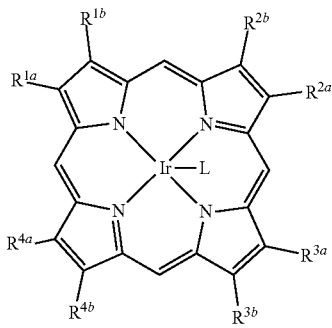

wherein $R^{1a}$, $R^{1b}$, $R^{2a}$, $R^{2b}$, $R^{3a}$, $R^{3b}$, $R^{4a}$ and $R^{4b}$ are each independently selected from the group consisting of hydrogen, $C_{1-6}$ alkyl, $C_{2-6}$ alkenyl, $C_{2-6}$ alkynyl, $C_{3-8}$ cycloalkyl and $C_{6-10}$ aryl, wherein the alkyl can be optionally substituted with —C(O)OR$^5$ wherein R$^5$ is hydrogen or $C_{1-6}$ alkyl.

5. The catalyst composition of claim 4, wherein $R^{1a}$, $R^{1b}$, $R^{2a}$, $R^{2b}$, $R^{3a}$, and $R^{4a}$ are each independently selected from the group consisting of hydrogen, $C_{1-6}$ alkyl and $C_{2-6}$ alkenyl; and $R^{3b}$ and $R^{4b}$ are each independently selected from the group consisting of $C_{1-6}$ alkyl, wherein the alkyl is substituted with —C(O)OR$^5$ wherein R$^5$ is hydrogen or $R^{1a}$, $R^{1b}$, $R^{2a}$, $R^{2b}$, $R^{3a}$, and $R^{4a}$ are each independently selected from the group consisting of hydrogen, methyl, ethyl and ethenyl; and $R^{3b}$ and $R^{4b}$ are each —CH$_2$CH$_2$—C(O)OH.

6. The catalyst composition of claim 4, wherein the porphyrin-Ir(L) complex is selected from the group consisting of:

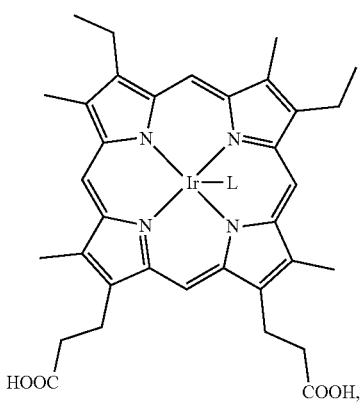

-continued

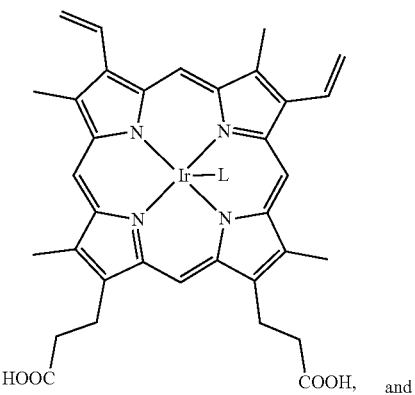

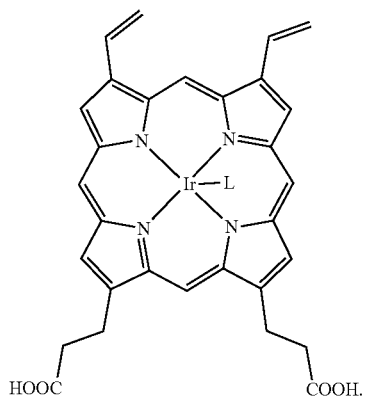

7. The catalyst composition of claim 4, wherein the porphyrin-Ir(L) complex is selected from the group consisting of:

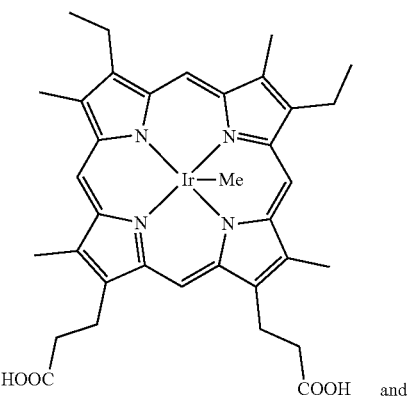

-continued

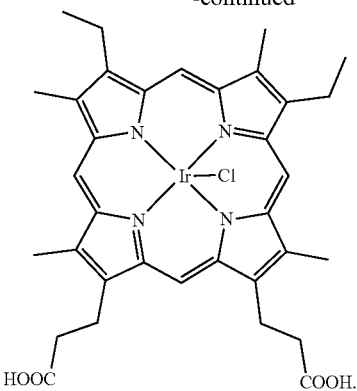

8. The catalyst composition of claim 1, wherein the at least one mutation close to the active site is at a position corresponding to an axial ligand position of a naturally occurring heme apoprotein.

9. The catalyst composition of claim 1, wherein the heme apoprotein is the cytochrome P450 and the cytochrome P450 has at least 70% sequence identity to the P450 region of SEQ ID NO:3; and comprises substitutions C317G, L69V, T213G, and V254L;
substitutions C317G, T213G, and F310G; substitutions C317G, L69Y, T213G, and A152W;
substitutions C317G, T213A, and V254L; substitutions C317G, L69F, T213G, and V254L;
substitutions C317G, L69Y, T213G, and A152W; substitutions C317G, L69W, T213G, and L318G; substitutions C317G, T213G, and V254L; substitutions C317G, L69V, T213G, and V254L; substitutions C317G, T213G, and V254L; substitutions C317G, L69W, and T213G; or substitutions C317G, L69V, T213A, V254L, and A152W, wherein the positions are numbered with reference to SEQ ID NO:1; or
the cytochrome P450 has at least 70% sequence identity to the P450 region of SEQ ID NO:3;
and comprises substitutions C317G and V254A; C317G, L69F, and T213V; C317G, V254A, and L155W; C317G, L69F, T213V, and V254L; T213G and V254L; C317G, L69F, T213V, and L155T;
C317G, V254A, and A152L; C317G, L69F, T213V, and V254L; C317G, V254A, and A152V;
C317G, T213G, V254L, and A152Y; C317G, V254A, and L155W; C317G, L69F, T213V, V254L, and L155T; C317G, L69F, T213V, and L155W; C317G and A209G; C317G, L69F, T213V, and V254L; C317G, V254A, F69L, L318F, and L155W; or C317G, L69F, T213V, and L155W; wherein the residues are numbered with reference to SEQ ID NO:1.

10. The catalyst composition of claim 1, wherein the heme apoprotein is the myoglobin and the myoglobin comprises a substitution at position H93 as determined with reference to SEQ ID NO:2;
the myoglobin comprises a substitution at positions H93, F43, and V68 as determined with reference to SEQ ID NO:2;
the myoglobin comprises an amino acid substitution at positions H64, F43, F33, L32, V68, H97, I99, Y103, and S108 as determined with reference to SEQ ID NO:2, optionally wherein the myoglobin comprises a substitution H93A/G, H64L/V/A, F43L/Y/W/H/I, L32F, F33V/I, V68A/S/G/T, H97W/Y, I99F/V, Y103C, and S108C as determined with reference to SEQ ID NO:2; or
the myoglobin has at least 70% sequence identity to the myoglobin region of SEQ ID NO:6;
and comprises substitutions H93A, H64L, F43L, and F33V; substitutions H93A, H64V, F43Y, V68A, and H97W; substitutions H93A, H64L, F43W, V68A, and H97Y; substitutions H93G, H64L, F43L, and I99F; substitutions H93A, H64V, V68A, Y103C, and S108C; substitutions H93A, H64L, F43W, V68A, and F33I; substitutions H93A, H64V, F43H, and V68S; substitutions H93A, H64A, F43W, and V68G; substitutions H93A, H64A, F43W, and V68T; substitutions H93A, H64A, F43I, and V68T; substitutions H93G, H64L, V68A, and I99V substitutions H93A, H64L, V68A, and I99V; substitutions H93A, H64V, V68A, F33V and H97Y; or substitutions H93G and H64L.

11. The catalyst composition of claim 1, wherein the heme apoprotein is the cytochrome P450 that has at least 80% identity to the P450 region of SEQ ID NO:3, wherein:
(a) the cytochrome P450 comprises substitutions at positions:
(i) C317, L69, T213, and V254; C317, T213, and F310; C317, L69, T213, and A152;
C317, T213, and V254; C317, L69, T213, and V254; C317 and T213; C317, L69, T213, and A152; C317, L69, T213, and L318; C317, T213, and V254; C317, L69, T213, and V254; C317, T213, and V254; C317, L69, and T213; or C317, L69, T213, V254, and A152, wherein the positions are numbered with reference to SEQ ID NO:1; or
(ii) C317 and V254; C317, L69, and T213; C317, V254, and L155; C317, L69, T213, and V254; T213 and V254; C317, L69, T213, and L155; C317, V254, and A152; C317, L69, T213, and V254; C317, V254, and A152; C317, T213, V254, and A152; C317, V254, and L155; C317, L69, T213, V254, and L155; C317, L69, T213, and L155; C317 and A209; C317, L69, T213, and V254; C317, V254, F69, L318, and L155; or C317, L69, T213, and L155, wherein the positions are numbered with reference to SEQ ID NO:1; or
(b) the cytochrome P450 comprises:
(i) substitutions C317G, L69V, T213G, and V254L; substitutions C317G, T213G, and F310G; substitutions C317G, L69Y, T213G, and A152W; substitutions C317G, T213A, and V254L; substitutions C317G, L69F, T213G, and V254L; substitutions C317G, L69Y, T213G, and A152W; substitutions C317G, L69W, T213G, and L318G; substitutions C317G, T213G, and V254L; substitutions C317G, L69V, T213G, and V254L; substitutions C317G, T213G, and V254L; substitutions C317G, L69W, and T213G; or substitutions C317G, L69V, T213A, V254L, and A152W, wherein the positions are numbered with reference to SEQ ID NO:1; or
(ii) substitutions C317G and V254A; C317G, L69F, and T213V; C317G, V254A, and L155W; C317G, L69F, T213V, and V254L; T213G and V254L; C317G, L69F, T213V, and L155T; C317G, V254A, and A152L; C317G, L69F, T213V, and V254L; C317G, V254A, and A152V; C317G, T213G, V254L, and A152Y; C317G, V254A, and L155W;
C317G, L69F, T213V, V254L, and L155T; C317G, L69F, T213V, and L155W; C317G and A209G; C317G, L69F, T213V, and V254L; C317G, V254A, F69L, L318F, and L155W; or C317G, L69F, T213V, and L155W; wherein the residues are numbered with reference to SEQ ID NO: 1.

12. The catalyst composition of claim 1, wherein the heme apoprotein is the myoglobin having at least 80% identity to the myoglobin region of SEQ ID NO:6; and further, wherein the myoglobin comprises substitutions at positions: H93, H64, F43, and F33; H93, H64, F43, V68, and H97; H93, H64, F43W, V68, and H97; H93, H64, F43, and I99; H93, H64, V68, Y103, and 5108; H93, H64, F43, V68, and F33; H93, H64, F43, and V68; H93, H64, F43, and V68; H93, H64, F43, and V68; H93, H64, F43, and V68; H93, H64, V68, and I99; H93, H64, V68, and I99; H93, H64, V68, F33 and H97; or H93, H64, V68, L32, and H97; wherein the residues are numbered with reference to SEQ ID NO:2; optionally wherein the myoglobin has at least comprises: substitutions H93A, H64L, F43L, and F33V; substitutions H93A, H64V, F43Y, V68A, and H97W; substitutions H93A, H64L, F43W, V68A, and H97Y; substitutions H93G, H64L, F43L, and I99F; substitutions H93A, H64V, V68A, Y103C, and S108C; substitutions H93A, H64L, F43W, V68A, and F33I; substitutions H93A, H64V, F43H, and V68S; substitutions H93A, H64A, F43W, and V68G; substitutions H93A, H64A, F43W, and V68T; substitutions H93A, H64A, F43I, and V68T; substitutions H93G, H64L, V68A, and I99V; substitutions H93A, H64L, V68A, and I99V; substitutions H93A, H64V, V68A, F33V and H97Y; or substitutions H93G, H64L, V68A, L32F, and H97Y; wherein the residues are numbered with reference to SEQ ID NO:2.

13. A method of forming a bond, comprising forming a reaction mixture comprising a catalyst composition of claim 1, a reactant selected from the group consisting of a carbene precursor and a nitrene precursor, and a substrate comprising an olefin or a C—H group, under conditions where the reactant forms a carbene or nitrene which inserts into the alkene or C—H bond of the substrate to form the bond between the reactant and the substrate.

14. The method of claim 13, wherein the carbene or nitrene precursor comprises a diazo

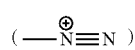

group.

15. The method of claim 13, wherein the reactant is a carbene precursor selected from the group consisting of an α-diazoester, an α-diazoamide, an α-diazonitrile, an α-diazoketone, an α-diazoaldehyde, and an α-diazosilane; or the reactant is a nitrene precursor selected from the group consisting of a sulfonyl azide, a sulfinyl azide, keto azide, ester azide, phosphono azide and phosphino azide.

16. The method of claim 13, wherein the substrate comprises an olefin selected from the group consisting of an alkene, cycloalkene and an arylalkene; or the substrate comprises an olefin such that the bond formed between the reactant and the substrate results in formation of a cyclopropane.

17. The method of claim 13, wherein the substrate and the reactant are the same compound such that the substrate comprises a C-H group, and such that the bond formed between the reactant and the substrate results in formation of a $C_{5-6}$ cycloalkyl or $C_{5-6}$ heterocycloalkyl; or the substrate and the reactant are the same compound such that the substrate comprises a C-H group and a sulfonyl azide, such that the bond formed between the reactant and the substrate results in formation of an amine bond.

18. The catalyst composition of claim 1, wherein the porphyrin is selected from the group consisting of:

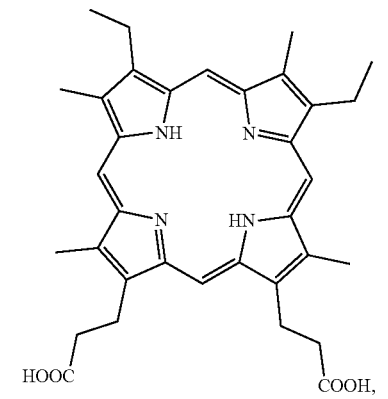

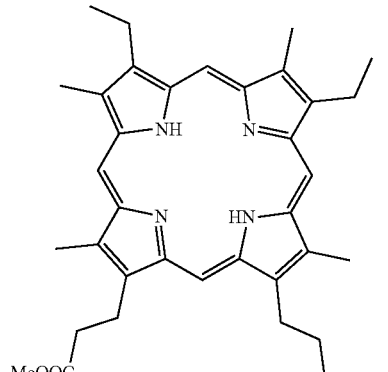

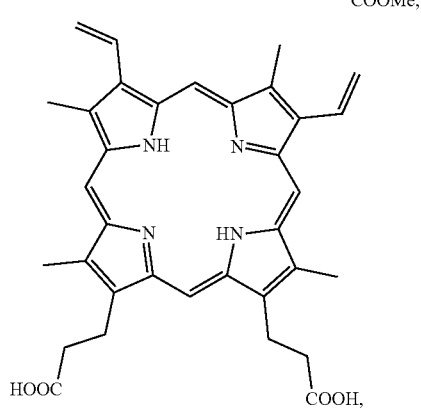 and

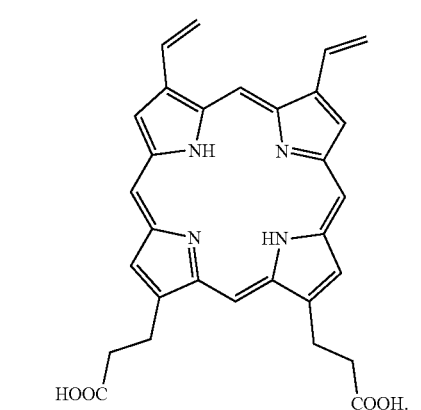

19. The catalyst composition of claim 4, wherein the heme apoprotein is a variant of a myoglobin.

\* \* \* \* \*

SEQUENCE LISTING

<160> NUMBER OF SEQ ID NOS: 12

<210> SEQ ID NO 1
<211> LENGTH: 368
<212> TYPE: PRT
<213> ORGANISM: Sufolobus sofataricus

<400> SEQUENCE: 1

Met Tyr Asp Trp Phe Ser Glu Met Arg Lys Lys Asp Pro Val Tyr Tyr
1               5                   10                  15

Asp Gly Asn Ile Trp Gln Val Phe Ser Tyr Arg Tyr Thr Lys Glu Val
            20                  25                  30

Leu Asn Asn Phe Ser Lys Phe Ser Ser Asp Leu Thr Gly Tyr His Glu
        35                  40                  45

Arg Leu Glu Asp Leu Arg Asn Gly Lys Ile Arg Phe Asp Ile Pro Thr
50                  55                  60

Arg Tyr Thr Met Leu Thr Ser Asp Pro Pro Leu His Asp Glu Leu Arg
65                  70                  75                  80

Ser Met Ser Ala Asp Ile Phe Ser Pro Gln Lys Leu Gln Thr Leu Glu
                85                  90                  95

Thr Phe Ile Arg Glu Thr Thr Arg Ser Leu Leu Asp Ser Ile Asp Pro
                100                 105                 110

Arg Glu Asp Asp Ile Val Lys Lys Leu Ala Val Pro Leu Pro Ile Ile
            115                 120                 125

Val Ile Ser Lys Ile Leu Gly Leu Pro Ile Glu Asp Lys Glu Lys Phe
130                 135                 140

Lys Glu Trp Ser Asp Leu Val Ala Phe Arg Leu Gly Lys Pro Gly Glu
145                 150                 155                 160

Ile Phe Glu Leu Gly Lys Lys Tyr Leu Glu Leu Ile Gly Tyr Val Lys
                165                 170                 175

Asp His Leu Asn Ser Gly Thr Glu Val Val Ser Arg Val Val Asn Ser
                180                 185                 190

Asn Leu Ser Asp Ile Glu Lys Leu Gly Tyr Ile Ile Leu Leu Leu Ile
                195                 200                 205

Ala Gly Asn Glu Thr Thr Thr Asn Leu Ile Ser Asn Ser Val Ile Asp
            210                 215                 220

Phe Thr Arg Phe Asn Leu Trp Gln Arg Ile Glu Glu Asn Leu Tyr
225                 230                 235                 240

Leu Lys Ala Ile Glu Glu Ala Leu Arg Tyr Ser Pro Pro Val Met Arg
                245                 250                 255

Thr Val Arg Lys Thr Lys Glu Arg Val Lys Leu Gly Asp Gln Thr Ile
                260                 265                 270

Glu Gly Glu Tyr Val Arg Val Trp Ile Ala Ser Ala Asn Arg Asp
                275                 280                 285

Glu Glu Val Phe His Asp Gly Glu Lys Phe Ile Pro Asp Arg Asn Pro
290                 295                 300

Asn Pro His Leu Ser Phe Gly Ser Gly Ile His Leu Cys Leu Gly Ala
305                 310                 315                 320

Pro Leu Ala Arg Leu Glu Ala Arg Ile Ala Ile Glu Glu Phe Ser Lys
                325                 330                 335

Arg Phe Arg His Ile Glu Ile Leu Asp Thr Glu Lys Val Pro Asn Glu
                340                 345                 350

Val Leu Asn Gly Tyr Lys Arg Leu Val Val Arg Leu Lys Ser Asn Glu
                355                 360                 365

<210> SEQ ID NO 2
<211> LENGTH: 149
<212> TYPE: PRT
<213> ORGANISM: Physeter macrocephalus

<400> SEQUENCE: 2

Val Leu Ser Glu Gly Glu Trp Gln Leu Val Leu His Val Trp Ala Lys
1               5                   10                  15

Val Glu Ala Asp Val Ala Gly His Gly Gln Asp Ile Leu Ile Arg Leu
                20                  25                  30

Phe Lys Ser His Pro Glu Thr Leu Glu Lys Phe Asp Arg Phe Lys His
            35                  40                  45

Leu Lys Thr Glu Ala Glu Met Lys Ala Ser Glu Asp Leu Lys Lys His
50                  55                  60

Gly Val Thr Val Leu Thr Ala Leu Gly Ala Ile Leu Lys Lys Lys Gly
65                  70                  75                  80

His His Glu Ala Glu Leu Lys Pro Leu Ala Gln Ser His Ala Thr Lys
                85                  90                  95

His Lys Ile Pro Ile Lys Tyr Leu Glu Phe Ile Ser Glu Ala Ile Ile
            100                 105                 110

His Val Leu His Ser Arg His Pro Gly Asp Phe Gly Ala Asp Ala Gln
            115                 120                 125

Gly Ala Met Asn Lys Ala Leu Glu Leu Phe Arg Lys Asp Ile Ala Ala
130                 135                 140

Lys Tyr Lys Glu Leu
145

<210> SEQ ID NO 3
<211> LENGTH: 394
<212> TYPE: PRT
<213> ORGANISM: Artificial Sequence
<220> FEATURE:
<223> OTHER INFORMATION: Synthetic construct

<400> SEQUENCE: 3

Thr Glu Val Gly Asp Ile His Met Lys Ser His His His His
1               5                   10                  15

His Glu Asn Leu Tyr Phe Gln Ser Asn Ala Met Tyr Asp Trp Phe Ser
                20                  25                  30

Glu Met Arg Lys Lys Asp Pro Val Tyr Tyr Asp Gly Asn Ile Trp Gln
            35                  40                  45

Val Phe Ser Tyr Arg Tyr Thr Lys Glu Val Leu Asn Asn Phe Ser Lys
50                  55                  60

Phe Ser Ser Asp Leu Thr Gly Tyr His Glu Arg Leu Glu Asp Leu Arg
65                  70                  75                  80

Asn Gly Lys Ile Arg Phe Asp Ile Pro Thr Arg Tyr Thr Met Leu Thr
                85                  90                  95

Ser Asp Pro Pro Leu His Asp Glu Leu Arg Ser Met Ser Ala Asp Ile
            100                 105                 110

Phe Ser Pro Gln Lys Leu Gln Thr Leu Glu Thr Phe Ile Arg Glu Thr
        115                 120                 125

Thr Arg Ser Leu Leu Asp Ser Ile Asp Pro Arg Glu Asp Asp Ile Val
130                 135                 140

Lys Lys Leu Ala Val Pro Leu Pro Ile Ile Val Ile Ser Lys Ile Leu
145                 150                 155                 160

Gly Leu Pro Ile Glu Asp Lys Glu Lys Phe Lys Glu Trp Ser Asp Leu
                165                 170                 175

Val Ala Phe Arg Leu Gly Lys Pro Gly Glu Ile Phe Glu Leu Gly Lys
            180                 185                 190

Lys Tyr Leu Glu Leu Ile Gly Tyr Val Lys Asp His Leu Asn Ser Gly
        195                 200                 205

Thr Glu Val Val Ser Arg Val Val Asn Ser Asn Leu Ser Asp Ile Glu
210                 215                 220

Lys Leu Gly Tyr Ile Ile Leu Leu Ile Ala Gly Asn Glu Thr Thr
225                 230                 235                 240

Thr Asn Leu Ile Ser Asn Ser Val Ile Asp Phe Thr Arg Phe Asn Leu
                245                 250                 255

Trp Gln Arg Ile Arg Glu Glu Asn Leu Tyr Leu Lys Ala Ile Glu Glu
            260                 265                 270

```
Ala Leu Arg Tyr Ser Pro Pro Val Met Arg Thr Val Arg Lys Thr Lys
            275                 280                 285

Glu Arg Val Lys Leu Gly Asp Gln Thr Ile Glu Gly Glu Tyr Val
290                 295                 300

Arg Val Trp Ile Ala Ser Ala Asn Arg Asp Glu Glu Val Phe His Asp
305                 310                 315                 320

Gly Glu Lys Phe Ile Pro Asp Arg Asn Pro Asn Pro His Leu Ser Phe
                325                 330                 335

Gly Ser Gly Ile His Leu Cys Leu Gly Ala Pro Leu Ala Arg Leu Glu
                340                 345                 350

Ala Arg Ile Ala Ile Glu Glu Phe Ser Lys Arg Phe Arg His Ile Glu
            355                 360                 365

Ile Leu Asp Thr Glu Lys Val Pro Asn Glu Val Leu Asn Gly Tyr Lys
            370                 375                 380

Arg Leu Val Val Arg Leu Lys Ser Asn Glu
385                 390

<210> SEQ ID NO 4
<211> LENGTH: 469
<212> TYPE: PRT
<213> ORGANISM: Artificial Sequence
<220> FEATURE:
<223> OTHER INFORMATION: Synthetic construct

<400> SEQUENCE: 4

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
        50                  55                  60

Ser Arg Phe Asp Lys Asn Leu Ser Gln Ala Leu Lys Phe Ala Arg Asp
65                  70                  75                  80

Phe Ala Gly Asp Gly Leu Val Thr Ser Trp Thr His Glu Lys Asn Trp
                85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
            115                 120                 125

Lys Trp Glu Arg Leu Asn Ala Asp Glu His Ile Glu Val Ser Glu Asp
130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
                180                 185                 190

Pro Asp Asp Pro Ala Tyr Asp Glu Asn Lys Arg Gln Phe Gln Glu Asp
            195                 200                 205

Ile Lys Val Met Asn Asp Leu Val Asp Lys Ile Ile Ala Asp Arg Lys
        210                 215                 220

Ala Arg Gly Glu Gln Ser Asp Asp Leu Leu Thr Gln Met Leu Asn Gly
225                 230                 235                 240
```

Lys Asp Pro Glu Thr Gly Glu Pro Leu Asp Asp Gly Asn Ile Arg Tyr
            245                 250                 255

Gln Ile Ile Thr Phe Leu Ile Ala Gly His Glu Ala Thr Ser Gly Leu
        260                 265                 270

Leu Ser Phe Ala Leu Tyr Phe Leu Val Lys Asn Pro His Val Leu Gln
    275                 280                 285

Lys Val Ala Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
            325                 330                 335

Glu Asp Thr Val Leu Gly Gly Glu Tyr Pro Leu Glu Lys Gly Asp Glu
        340                 345                 350

Val Met Val Leu Ile Pro Gln Leu His Arg Asp Lys Thr Val Trp Gly
    355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Ser
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Lys Gly Phe Val Val Lys Ala
            435                 440                 445

Lys Ser Lys Lys Ile Pro Leu Gly Gly Ile Pro Ser Pro Ser Thr His
450                 455                 460

His His His His His
465

<210> SEQ ID NO 5
<211> LENGTH: 420
<212> TYPE: PRT
<213> ORGANISM: Artificial Sequence
<220> FEATURE:
<223> OTHER INFORMATION: Synthetic construct

<400> SEQUENCE: 5

Met Thr Thr Glu Thr Ile Gln Ser Asn Ala Asn Leu Ala Pro Leu Pro
1               5                   10                  15

Pro His Val Pro Glu His Leu Val Phe Asp Phe Asp Met Tyr Asn Pro
            20                  25                  30

Ser Asn Leu Ser Ala Gly Val Gln Glu Ala Trp Ala Val Leu Gln Glu
        35                  40                  45

Ser Asn Val Pro Asp Leu Val Trp Thr Arg Cys Asn Gly Gly His Trp
    50                  55                  60

Ile Ala Thr Arg Gly Gln Leu Ile Arg Glu Ala Tyr Glu Asp Tyr Arg
65                  70                  75                  80

His Phe Ser Ser Glu Cys Pro Phe Ile Pro Arg Glu Ala Gly Glu Ala
            85                  90                  95

Tyr Asp Phe Ile Pro Thr Ser Met Asp Pro Pro Glu Gln Arg Gln Phe
        100                 105                 110

Arg Ala Leu Ala Asn Gln Val Val Gly Met Pro Val Val Asp Lys Leu
    115                 120                 125

Glu Asn Arg Ile Gln Glu Leu Ala Cys Ser Leu Ile Glu Ser Leu Arg
            130                 135                 140

Pro Gln Gly Gln Cys Asn Phe Thr Glu Asp Tyr Ala Glu Pro Phe Pro
145                 150                 155                 160

Ile Arg Ile Phe Met Leu Leu Ala Gly Leu Pro Glu Glu Asp Ile Pro
                165                 170                 175

His Leu Lys Tyr Leu Thr Asp Gln Met Thr Arg Pro Asp Gly Ser Met
            180                 185                 190

Thr Phe Ala Glu Ala Lys Glu Ala Leu Tyr Asp Tyr Leu Ile Pro Ile
        195                 200                 205

Ile Glu Gln Arg Arg Gln Lys Pro Gly Thr Asp Ala Ile Ser Ile Val
210                 215                 220

Ala Asn Gly Gln Val Asn Gly Arg Pro Ile Thr Ser Asp Glu Ala Lys
225                 230                 235                 240

Arg Met Cys Gly Leu Leu Val Gly Gly Leu Asp Thr Val Val Asn
                245                 250                 255

Phe Leu Ser Phe Ser Met Glu Phe Leu Ala Lys Ser Pro Glu His Arg
            260                 265                 270

Gln Glu Leu Ile Gln Arg Pro Glu Arg Ile Pro Ala Ala Cys Glu Glu
        275                 280                 285

Leu Leu Arg Arg Phe Ser Leu Val Ala Asp Gly Arg Ile Leu Thr Ser
290                 295                 300

Asp Tyr Glu Phe His Gly Val Gln Leu Lys Lys Gly Asp Gln Ile Leu
305                 310                 315                 320

Leu Pro Gln Met Leu Ser Gly Leu Asp Glu Arg Glu Asn Ala Cys Pro
                325                 330                 335

Met His Val Asp Phe Ser Arg Gln Lys Val Ser His Thr Thr Phe Gly
            340                 345                 350

His Gly Ser His Leu Cys Leu Gly Gln His Leu Ala Arg Arg Ile Ile
        355                 360                 365

Val Thr Leu Lys Glu Trp Leu Thr Arg Ile Pro Asp Phe Ser Ile Ala
370                 375                 380

Pro Gly Ala Gln Ile Gln His Lys Ser Gly Ile Val Ser Gly Val Gln
385                 390                 395                 400

Ala Leu Pro Leu Val Trp Asp Pro Ala Thr Thr Lys Ala Val His His
                405                 410                 415

His His His His
        420

<210> SEQ ID NO 6
<211> LENGTH: 304
<212> TYPE: PRT
<213> ORGANISM: Artificial Sequence
<220> FEATURE:
<223> OTHER INFORMATION: Synthetic construct

<400> SEQUENCE: 6

Glu Gly Asp Ile His Met Lys Ser Ser His His His His His His Glu
1               5                   10                  15

Asn Leu Tyr Phe Gln Ser Asn Met Ser Asn Met Thr Tyr Asn Asn Val
            20                  25                  30

Phe Asp His Ala Tyr Glu Met Leu Lys Glu Asn Ile Arg Tyr Asp Asp
        35                  40                  45

Ile Arg Asp Thr Asp Asp Leu His Asp Ala Ile His Met Ala Ala Asp
    50                  55                  60

Asn Ala Val Pro His Tyr Tyr Ala Asp Ile Arg Ser Val Met Ala Ser
65                  70                  75                  80

Glu Gly Ile Asp Leu Glu Phe Glu Asp Ser Gly Leu Met Pro Asp Thr
            85                  90                  95

Lys Asp Asp Ile Arg Ile Leu Gln Ala Arg Ile Tyr Glu Gln Leu Thr
            100                 105                 110

Ile Asp Leu Trp Glu Asp Ala Glu Asp Leu Leu Asn Glu Tyr Leu Glu
            115                 120                 125

Glu Val Glu Glu Tyr Glu Glu Asp Glu Glu Gly Thr Gly Ser Glu Thr
130                 135                 140

Pro Gly Thr Ser Glu Ser Gly Val Leu Ser Glu Gly Leu Trp Gln Leu
145                 150                 155                 160

Val Leu His Val Trp Ala Lys Val Glu Ala Asp Val Ala Gly His Gly
                165                 170                 175

Gln Asp Ile Leu Ile Arg Leu Phe Lys Ser His Pro Glu Thr Leu Glu
            180                 185                 190

Lys Phe Asp Arg Phe Lys His Leu Lys Thr Glu Ala Glu Met Lys Ala
            195                 200                 205

Ser Glu Asp Leu Lys Lys His Gly Val Thr Val Leu Thr Ala Leu Gly
210                 215                 220

Ala Ile Leu Lys Lys Lys Gly His His Glu Ala Glu Leu Lys Pro Leu
225                 230                 235                 240

Ala Gln Ser His Ala Thr Lys His Lys Ile Pro Ile Lys Tyr Leu Glu
            245                 250                 255

Phe Ile Ser Glu Ala Ile Ile His Val Leu His Ser Arg His Pro Gly
            260                 265                 270

Asp Phe Gly Ala Asp Ala Gln Gly Ala Met Asn Lys Ala Leu Glu Leu
            275                 280                 285

Phe Arg Lys Asp Ile Ala Ala Lys Tyr Lys Glu Leu Gly Tyr Gln Gly
            290                 295                 300

<210> SEQ ID NO 7
<211> LENGTH: 4
<212> TYPE: PRT
<213> ORGANISM: Artificial Sequence
<220> FEATURE:
<223> OTHER INFORMATION: Synthetic construct

<400> SEQUENCE: 7

Ser Gly Asn His
1

<210> SEQ ID NO 8
<211> LENGTH: 5
<212> TYPE: PRT
<213> ORGANISM: Artificial Sequence
<220> FEATURE:
<223> OTHER INFORMATION: Synthetic construct

<400> SEQUENCE: 8

Arg Lys His Pro Thr
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic construct

<400> SEQUENCE: 9

Leu Ile Val Met Phe Ala Pro
1               5

<210> SEQ ID NO 10
<211> LENGTH: 177
<212> TYPE: PRT
<213> ORGANISM: Artificial Sequence
<220> FEATURE:
<223> OTHER INFORMATION: Synthetic construct

<400> SEQUENCE: 10

Glu Gly Asp Ile His Met Lys Ser Ser His His His His His Glu
1               5                   10                  15

Asn Leu Tyr Phe Gln Ser Asn Ala Val Leu Ser Glu Gly Glu Trp Gln
            20                  25                  30

Leu Val Leu His Val Trp Ala Lys Val Glu Ala Asp Val Ala Gly His
        35                  40                  45

Gly Gln Asp Ile Leu Ile Arg Leu Phe Lys Ser His Pro Glu Thr Leu
    50                  55                  60

Glu Lys Phe Asp Arg Phe Lys His Leu Lys Thr Glu Ala Glu Met Lys
65                  70                  75                  80

Ala Ser Glu Asp Leu Lys Lys His Gly Val Thr Val Leu Thr Ala Leu
                85                  90                  95

Gly Ala Ile Leu Lys Lys Lys Gly His His Glu Ala Glu Leu Lys Pro
            100                 105                 110

Leu Ala Gln Ser His Ala Thr Lys His Lys Ile Pro Ile Lys Tyr Leu
        115                 120                 125

Glu Phe Ile Ser Glu Ala Ile Ile His Val Leu His Ser Arg His Pro
    130                 135                 140

Gly Asp Phe Gly Ala Asp Ala Gln Gly Ala Met Asn Lys Ala Leu Glu
145                 150                 155                 160

Leu Phe Arg Lys Asp Ile Ala Ala Lys Tyr Lys Glu Leu Gly Tyr Gln
                165                 170                 175

Gly

<210> SEQ ID NO 11
<211> LENGTH: 304
<212> TYPE: PRT
<213> ORGANISM: Artificial Sequence
<220> FEATURE:
<223> OTHER INFORMATION: Synthetic construct

<400> SEQUENCE: 11

Glu Gly Asp Ile His Met Lys Ser Ser His His His His His Glu
1               5                   10                  15

Asn Leu Tyr Phe Gln Ser Asn Met Ser Asn Met Thr Tyr Asn Asn Val
            20                  25                  30

Phe Asp His Ala Tyr Glu Met Leu Lys Glu Asn Ile Arg Tyr Asp Asp
        35                  40                  45

Ile Arg Asp Thr Asp Asp Leu His Asp Ala Ile His Met Ala Ala Asp
    50                  55                  60

Asn Ala Val Pro His Tyr Tyr Ala Asp Ile Arg Ser Val Met Ala Ser
65                  70                  75                  80

Glu Gly Ile Asp Leu Glu Phe Glu Asp Ser Gly Leu Met Pro Asp Thr
                85                  90                  95

```
Lys Asp Asp Ile Arg Ile Leu Gln Ala Arg Ile Tyr Glu Gln Leu Thr
                100                 105                 110

Ile Asp Leu Trp Glu Asp Ala Glu Asp Leu Leu Asn Glu Tyr Leu Glu
            115                 120                 125

Glu Val Glu Glu Tyr Glu Glu Asp Glu Glu Gly Thr Gly Ser Glu Thr
        130                 135                 140

Pro Gly Thr Ser Glu Ser Gly Val Leu Ser Glu Gly Glu Trp Gln Leu
145                 150                 155                 160

Val Leu His Val Trp Ala Lys Val Glu Ala Asp Val Ala Gly His Gly
                165                 170                 175

Gln Asp Ile Leu Ile Arg Leu Phe Lys Ser His Pro Glu Thr Leu Glu
            180                 185                 190

Lys Phe Asp Arg Phe Lys His Leu Lys Thr Glu Ala Glu Met Lys Ala
        195                 200                 205

Ser Glu Asp Leu Lys Lys His Gly Val Thr Val Leu Thr Ala Leu Gly
210                 215                 220

Ala Ile Leu Lys Lys Lys Gly His His Glu Ala Glu Leu Lys Pro Leu
225                 230                 235                 240

Ala Gln Ser His Ala Thr Lys His Lys Ile Pro Ile Lys Tyr Leu Glu
                245                 250                 255

Phe Ile Ser Glu Ala Ile Ile His Val Leu His Ser Arg His Pro Gly
            260                 265                 270

Asp Phe Gly Ala Asp Ala Gln Gly Ala Met Asn Lys Ala Leu Glu Leu
        275                 280                 285

Phe Arg Lys Asp Ile Ala Ala Lys Tyr Lys Glu Leu Gly Tyr Gln Gly
290                 295                 300

<210> SEQ ID NO 12
<211> LENGTH: 470
<212> TYPE: PRT
<213> ORGANISM: Artificial Sequence
<220> FEATURE:
<223> OTHER INFORMATION: Synthetic construct

<400> SEQUENCE: 12

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160
```

-continued

```
Tyr Arg Phe Asn Ser Phe Tyr Arg Asp Gln Pro His Pro Phe Ile Ile
                165                 170                 175
Ser Met Val Arg Ala Leu Asp Glu Val Met Asn Lys Leu Gln Arg Ala
                180                 185                 190
Asn Pro Asp Asp Pro Ala Tyr Asp Glu Asn Lys Arg Gln Phe Gln Glu
                195                 200                 205
Asp Ile Lys Val Met Asn Asp Leu Val Asp Lys Ile Ile Ala Asp Arg
210                 215                 220
Lys Ala Arg Gly Glu Gln Ser Asp Asp Leu Leu Thr Gln Met Leu Asn
225                 230                 235                 240
Gly Lys Asp Pro Glu Thr Gly Glu Pro Leu Asp Asp Gly Asn Ile Arg
                245                 250                 255
Tyr Gln Ile Ile Thr Phe Leu Ile Ala Gly His Glu Ala Thr Ser Gly
                260                 265                 270
Leu Leu Ser Phe Ala Leu Tyr Phe Leu Val Lys Asn Pro His Val Leu
                275                 280                 285
Gln Lys Val Ala Glu Glu Ala Ala Arg Val Leu Val Asp Pro Val Pro
                290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Glu Tyr Pro Leu Glu Lys Gly Asp
                340                 345                 350
Glu Val Met Val Leu Ile Pro Gln Leu His Arg Asp Lys Thr Val Trp
                355                 360                 365
Gly Asp Asp Val Glu Glu Phe Arg Pro Glu Arg Phe Glu Asn Pro Ser
370                 375                 380
Ala Ile Pro Gln His Ala Phe Lys Pro Phe Gly Asn Gly Gln Arg Ala
385                 390                 395                 400
Ser Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
                420                 425                 430
Asp Ile Lys Glu Thr Leu Thr Leu Lys Pro Lys Gly Phe Val Val Lys
                435                 440                 445
Ala Lys Ser Lys Lys Ile Pro Leu Gly Gly Ile Pro Ser Pro Ser Thr
                450                 455                 460
His His His His His His
465                 470
```